(12) United States Patent
Tanaka et al.

(10) Patent No.: US 9,182,407 B2
(45) Date of Patent: Nov. 10, 2015

(54) METHOD OF EVALUATING VISCERAL FAT ACCUMULATION, VISCERAL FAT ACCUMULATION-EVALUATING APPARATUS, VISCERAL FAT ACCUMULATION-EVALUATING METHOD, VISCERAL FAT ACCUMULATION-EVALUATING SYSTEM, VISCERAL FAT ACCUMULATION-EVALUATING PROGRAM, RECORDING MEDIUM, AND METHOD OF SEARCHING FOR PROPHYLACTIC/AMELIORATING SUBSTANCE FOR VISCERAL FAT ACCUMULATION

(75) Inventors: Takayuki Tanaka, Kanagawa (JP); Toshihiko Ando, Kanagawa (JP); Hiroshi Yamamoto, Tokyo (JP); Minoru Yamakado, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 560 days.

(21) Appl. No.: 12/644,798

(22) Filed: Dec. 22, 2009

(65) Prior Publication Data

US 2010/0173348 A1  Jul. 8, 2010

Related U.S. Application Data

(63) Continuation of application No. PCT/JP2008/061561, filed on Jun. 25, 2008.

(30) Foreign Application Priority Data

Jun. 25, 2007 (JP) .................... 2007-166219

(51) Int. Cl.
*G01N 33/68* (2006.01)
*G06F 19/00* (2011.01)

(52) U.S. Cl.
CPC ........ *G01N 33/6806* (2013.01); *G01N 2800/02* (2013.01); *G01N 2800/04* (2013.01); *G01N 2800/50* (2013.01); *G06F 19/3418* (2013.01); *G06F 19/366* (2013.01)

(58) Field of Classification Search
USPC ............................................ 702/19; 514/4.8
See application file for complete search history.

(56) References Cited

U.S. PATENT DOCUMENTS 6,631,330 B1  10/2003  Poynard
7,005,255 B2  2/2006  Kaddurah-Daouk et al.
(Continued)

FOREIGN PATENT DOCUMENTS

CA  2 443 806 A1  10/2002
EP  1 285 092  2/2003
(Continued)

OTHER PUBLICATIONS

Takahashi, M. 2006, vol. 21, No. 2, p. 589, 2-6-33. (On IDS).*
(Continued)

*Primary Examiner* — Sally Merkling
(74) *Attorney, Agent, or Firm* — Foley & Lardner LLP

(57) ABSTRACT

According to the method of evaluating visceral fat accumulation of the present invention, amino acid concentration data on concentration values of amino acids in blood collected from a subject to be evaluated is measured, and a visceral fat accumulation condition in the subject is evaluated based on the measured amino acid concentration data of the subject.

20 Claims, 37 Drawing Sheets

(56) References Cited

U.S. PATENT DOCUMENTS

| | | | |
|---|---|---|---|
| 7,329,489 B2 | 2/2008 | Kaddurah-Daouk et al. | |
| 7,550,258 B2 | 6/2009 | Kaddurah-Daouk et al. | |
| 7,550,260 B2 | 6/2009 | Kaddurah-Daouk et al. | |
| 7,553,616 B2 | 6/2009 | Kaddurah-Daouk et al. | |
| 7,635,556 B2 | 12/2009 | Kaddurah-Daouk et al. | |
| 8,234,075 B2 * | 7/2012 | Kimura et al. | 702/19 |
| 2002/0009740 A1 | 1/2002 | Kaddurah-Daouk et al. | |
| 2004/0022827 A1 | 2/2004 | Satomi et al. | |
| 2004/0039553 A1 | 2/2004 | Poynard | |
| 2004/0146853 A1 | 7/2004 | Kaddurah-Daouk et al. | |
| 2005/0014132 A1 | 1/2005 | Kaddurah-Daouk et al. | |
| 2005/0124865 A1 | 6/2005 | Kawanishi | |
| 2005/0283347 A1 | 12/2005 | Kimura et al. | |
| 2006/0134676 A1 | 6/2006 | Kaddurah-Daouk et al. | |
| 2006/0134677 A1 | 6/2006 | Kaddurah-Daouk et al. | |
| 2006/0134678 A1 | 6/2006 | Kaddurah-Daouk et al. | |
| 2007/0026389 A1 | 2/2007 | Kaddurah-Daouk et al. | |
| 2007/0072203 A1 | 3/2007 | Kaddurah-Daouk et al. | |
| 2007/0172820 A1 | 7/2007 | Kaddurah-Daouk et al. | |
| 2007/0172885 A1 | 7/2007 | Kaddurah-Daouk et al. | |
| 2007/0178599 A1 | 8/2007 | Kaddurah-Daouk et al. | |
| 2007/0218519 A1 | 9/2007 | Urdea et al. | |
| 2008/0147368 A1 | 6/2008 | Sugimoto et al. | |
| 2008/0154515 A1 | 6/2008 | Zhang et al. | |
| 2009/0017464 A1 | 1/2009 | Kaddurah-Daouk et al. | |
| 2009/0155826 A1 | 6/2009 | Hu et al. | |
| 2009/0253116 A1 | 10/2009 | Takahashi et al. | |
| 2009/0280521 A1 | 11/2009 | Kaddurah-Daouk et al. | |
| 2010/0017145 A1 | 1/2010 | Imaizumi et al. | |
| 2010/0173348 A1 | 7/2010 | Tanaka et al. | |
| 2010/0261282 A1 | 10/2010 | Takahashi et al. | |
| 2010/0279956 A1 | 11/2010 | McCreedy, Jr. et al. | |
| 2011/0282585 A9 | 11/2011 | Zhang et al. | |
| 2012/0041684 A1 | 2/2012 | Tanaka et al. | |
| 2012/0122981 A1 | 5/2012 | Hu et al. | |

FOREIGN PATENT DOCUMENTS

| | | | | |
|---|---|---|---|---|
| EP | 1 570 779 A1 | 9/2005 | | |
| EP | 2 172 775 A1 | 4/2010 | | |
| JP | 61-126472 A | 6/1986 | | |
| JP | 2000-298131 A | 10/2000 | | |
| JP | 2001-190299 A | 7/2001 | | |
| JP | EP 1570779 | * | 9/2005 | A61B 5/00 |
| JP | 2010-102579 A | 5/2010 | | |
| WO | WO 01/78652 A2 | 10/2001 | | |
| WO | WO 02/16949 A1 | 2/2002 | | |
| WO | WO 03/083133 A1 | 9/2003 | | |
| WO | WO 2004/052191 A1 | 6/2004 | | |
| WO | WO 2006/098192 A1 | 9/2006 | | |
| WO | WO 2006/129513 A1 | 12/2006 | | |
| WO | WO 2008/015929 A1 | 2/2008 | | |
| WO | WO 2008/075664 A1 | 6/2008 | | |
| WO | WO 2009/001862 A1 | 12/2008 | | |
| WO | WO 2009/054350 A1 | 4/2009 | | |
| WO | WO 2010/095682 A1 | 8/2010 | | |

OTHER PUBLICATIONS

International Search Report in PCT/JP2008/061561, dated Jul. 24, 2008, 3 pages.
Felig et al., "Plasma amino acid levels and insulin secretion in obesity," The New England Journal of Medicine, Oct. 9, 1969, 281(15):811-816.
Felig et al., "Plasma Amino Acid Levels in Diabetic Ketoacidosis," Diabetes, Oct. 1970, 19(10):727-729.
Kono et al., "Seikagakuteki kensa [1] D. Teibunshi Chisso Kagobutsu Kankei Amino acid to Sono Bunkaku," Japanese Journal of Clinical Medicine, 2004, 62(11):567-570, with partial English translation as indicated.
Metabolic Syndrome Diagnostic Criteria Examination Committee, "Metabolic Syndrome Definition and Health Standard," The Journal of Japanese Society of Internal Medicine, Apr. 10, 2005, 94:794-809, with partial English translation as indicated.
Takahashi et al., "Ningen Dock ni Okeru Kessho Amino acid Sokutei no Yuyosei ni Tsuitei: Metabolic Syndrome Kenshin," Ningen dock, 2006, 21(2):589, 2-6-33, with English translation.
Alberti et al., "The metabolic syndrome—a new worldwide definition," The Lancet, Sep. 24, 2005, 366:1059-1062.
Amamiya et al., "Negative correlations between free histidine content in plasma and BMI or area of visceral fat," JPFNI, 2008, 18(2):87-91.
Caballero et al., "Differential Effects of Insulin Resistance on Leucine and Glucose Kinetics in Obesity," Metabolism, Jan. 1991, 40(1):51-58.
Caballero et al., "Plasma amino acid concentrations in healthy elderly men and women," Am. J. Clin. Nutr., 1991, 53(5):1249-1252.
Caballero et al., "Plasma Amino Acid Levels in Obesity: Effects of Insulin Resistance," Amino Acids in Health and Disease: New Perspectives, 1987, 369-382.
Caballero et al., "Plasma Amino Acids and Insulin Levels in Obesity: Response to Carbohydrate Intake and Tryptophan Supplements," Metabolism, Jul. 1988, 37(7):672-676.
Evans et al., "Maternal and fetal amino acid concentrations and fetal outcomes during pre-eclampsia," Reproduction, 2003, 125:785-790.
Fischer et al., "The role of plasma amino acids in hepatic encephalopathy," Surgery, Sep. 1975, 78(3):276-290.
Fortunato et al., "Multivariate Discriminant Function Based on Six Biochemical Markers in Blood Can Predict the Cirrhotic Evolution of Chronic Hepatitis," Clinical Chemistry, 2001, 47(9):1696-1700.
Horie et al., "New Body Mass Index Criteria of Central Obesity for Male Japanese," Tohoku J. Exp. Med., 2006, 208:83-86.
Isomaa et al., "Cardiovascular Morbidity and Mortality Associated with the Metabolic Syndrome," Diabetes Care, Apr. 2001, 24(4):683-689.
Matsuzawa et al. (The Examination Committee of Criteria for 'Obesity disease' in Japan, Japan Society for the Study of Obesity), "New Criteria for 'Obesity Disease' in Japan," Circ. J., 2002, 66(11):987-992.
Minoru et al., "Comparative Studies on Blood Amino Acid Level in Normal, Seemingly Obese, Occult Obese, and Obese," The Journal of the Japanese Society of Internal Medicine, Feb. 20, 2009, 98(special extra issue):233, with English translation.
Noguchi et al., "Network analysis of plasma and tissue amino acids and the generation of an amino index for potential diagnostic use," Am. J. Clin. Nutr., Feb. 2006, 83(2):513S-519S.
Pijl et al., "Insulin-Induced Decline of Plasma Amino Acid Concentrations in Obese Subjects With and Without Non-Insulin-Dependent Diabetes," Metabolism, May 1994, 43(5):640-646.
Proenza et al., "Blood amino acid compartmentation in men and women with different degrees of obesity," J. Nutr. Biochem., 1998, 9:697-704.
Roca et al., "Sex Differences in the Effect of Obesity on Human Plasma Tryptophan/Large Neutral Amino Acid Ratio," Ann. Nutr. Metab., 1999, 43:145-151.
Sakurai et al., "Analysis on Blood Amino Acid Level in Obese Person," Japanese Journal of Cardiovascular Disease Prevention, Apr. 30, 2009, 44(2):109, with English translation.
Zhang et al., "Plasma amino acid profiles applied for diagnosis of advanced liver fibrosis in patients with chronic hepatitis C infection," Hepatology Research, 2006, 34:170-177.
Supplementary European Search Report dated Oct. 28, 2010, in corresponding EP 08765835.7, 7 pages.
Miyake, Makoto, "Clinical Studies on the Metabolism of Plasma Amino Acids in Various Diseases" Journal of the Nagoya City University Medical Association, 1977, 28(2)308-351, with English translation.
The New England Journal of Medicine, Jan. 15, 1970, 166; letter to the editor by Bagdade et al. regarding article NEJM 218:811-816, 1969, and response letter by Felig et al.
Felig et al., "Splanchnic Glucose and Amino Acid Metabolism in Obesity," The Journal of Clinical Investigation, Feb. 1974, 53:582-590.
Marchesini et al., "Effects of hyperglycaemia and hyperinsulinaemia on plasma amino acid levels in obese subjects with normal glucose tolerance," International Journal of Obesity, 2000, 24:552-558.

(56) References Cited

OTHER PUBLICATIONS

Rafecas et al., "Plasma amino acids of lean and obese Zucker rats subjected to a cafeteria diet after weaning," Biochemistry International, Dec. 1991, 25(5):797-806.
Schauder et al., "Sex-specific differences in plasma branched-chain keto acid levels in obesity," Am. J. Clin. Nutr., 1987, 46:58-60.
She et al., "Obesity-related elevations in plasma leucine are associated with alterations in enzymes involved in branched-chain amino acid metabolism," Am. J. Physiol. Endocrinol. Metab., Oct. 9, 2007, 293:E1552-E1563.
Solini et al., "Protein Metabolism in Human Obesity: Relationship with Glucose and Lipid Metabolism and with Visceral Adipose Tissue," Journal of Clinical Endocrinology and Metabosm, 1997, 82(8):2552-2558.
Tremblay et al., "Overactivation of S6 Kinase 1 as a Cause of Human Insulin Resistance During Increased Amino Acid Availability," Diabetes, Sep. 2005, 54:2674-2684.
Wijekoon et al., "Amino acid metabolism in the Zucker diabetic fatty rat: effects of insulin resistance and of type 2 diabetes," Can. J. Physiol. Pharmacol., 2004, 82:506-514.
Despres et al., "Abdominal obesity and metabolic syndrome," Nature, Dec. 14, 2006, 444:881-887.
Newgard et al., "A Branched-Chain Amino Acid-Related Metabolic Signature that Differentiates Obese and Lean Humans and Contributes to Insulin Resistance," Cell Metabolism, Apr. 8, 2009, 9:311-326.
Rosen et al., "Plasma Amino Acid Patterns in Hepatic Encephalopathy of Differing Etiology," Gastroenterology, 1977, 72:483-487.
Pyorala et al., "Hyperinsulinemia Predicts Coronary Heart Disease Risk in Healthy Middle-aged Men, The 22-Year Follow-up Results of the Helsinki Policemen Study," Circulation, 1998, 98:398-404.
Soeters et al., "Insulin, Glucagon, Aminoacid Imbalance, and Hepatic Encephalopathy," The Lancet, Oct. 23, 1976, 880-882.
Van Gaal et al., "Mechanisms linking obesity with cardiovascular disease," Nature, Dec. 14, 2006, 444:875-880.
Abukawa et al., "An undescribed subset of neonatal intrahepatic cholestasis associated with multiple hyperaminoacidemia," Hepatology Research, 2001, 21:8-13.
Dahlhoff et al., "Hepatic Methionine Homeostasis is Conserved in C57BL/6N Mice on High-Fat Diet Despite Major Changes in Hepatic One-Carbon Metabolism," PloS One, Mar. 2013, 8(3):e57387, 1-12.
Enwonwu et al., "Accumulation of histidine, 3-methylhistidine, and homocarnosine in the brains of protein-calorie deficient monkeys," Journal of Neurochemistry, 1973, 21:799-807.
Hamiki et al., "Phosphoenolpyruvate carboxykinase and the critical role of cataplerosis in the control of hepatic metabolism," Nutrition & Metabolism, 2005, 2:33, 1-12.
Levine et al., "Tyrosine Metabolism in Patients with Liver Disease," J. Clin. Invest., 1967, 46(12):2012-2020.
Loguercio et al., "Ethanol Consumption, Amino Acid and Glutathione Blood Levels in Patients With and Without Chronic Liver Disease," Alcoholism: Clinical and Experimental Research, Nov. 1999, 23(11):1780-1784.
Morgan et al.,"Plasma amino-acid patterns in liver disease," Gut, 1982, 23:362-370.
Mukherjee et al., "Role of plasma amino acids and GABA in alcoholic and non-alcoholic fatty liver disease—A pilot study," Indian Journal of Clinical Biochemistry, 2010, 25(1):37-42.
Nakajima et al., "Abnormal Amino Acid Metabolism in Various Diseases and Countermeasures," Nihon Rinsho 50, 1992, 1609-1613, with English translation.
Plauth et al., "Characteristic Pattern of Free Amino Acids in Plasma and Skeletal Muscle in Stable Hepatic Cirrhosis," Hepatogastroenterol., 1990, 37:135-139.
Shaw et al., "Plasma amino acid abnormalities in the alcoholic, Respective role of alcohol, nutrition, and livery injury," Gastroenterology, 1978, 74:677-682.
Stanko et al., "Prevention of Effects of Ethanol on Amino Acid Concentrations in Plasma and Tissues by Hepatic Lipotropic Factors in Rats," Gastroenterology, 1979, 76(1):132-138.
Wu et al., "Changes in Free Amino Acids in the Plasma During Hepatic Coma," J. Clin. Invest., 1955, 34:845-849.
Hirai, Yoshinori, "A Study of Amino Acid Metabolism in Patients with Gastric Cancer," Journal of Japan Surgical Society, Jul. 1, 1965, 66:983-1013, with English translation.
Kwon et al., "Plasma Free Amino Acids and Various Nutritional Indices Analyzed in Relation to Growth of Gastric Cancer," Japanese Journal of Surgical Metabolism and Nutrition, Apr. 1995, 29(2):129-134, with English translation.

* cited by examiner (BASIC PRINCIPLE OF INVENTION)

(BASIC PRINCIPLE OF THE INVENTION)

FIG.7

| USER ID | USER PASSWORD | NAME | ORGANI-ZATION ID | DEPART-MENT ID | DEPART-MENT NAME | E-MAIL ADDRESS | ... |
|---|---|---|---|---|---|---|---|
| : | : | : | : | : | : | : | : |

| INDIVIDUAL (SAMPLE) NO. | AMINO ACID CONCENTRATION DATA | | | | | |
|---|---|---|---|---|---|---|
| | Gly | Leu | Val | Ile | Phe | ... |
| U-1 | 9.5 | 11.2 | 2.7 | 8.5 | 4.9 | ... |
| U-2 | 8.5 | 10.5 | 3.9 | 9.8 | 6.1 | ... |
| : | : | : | : | : | : | : |

| INDIVIDUAL (SAMPLE) NO. | VISCERAL FAT ACCUMULATION CONDITION INDEX DATA (T) | | | | AMINO ACID CONCENTRATION DATA | | | | | |
|---|---|---|---|---|---|---|---|---|---|---|
| | $T_1$ | $T_2$ | $T_3$ | ... | Gly | Leu | Val | Ile | Phe | ... |
| A-1 | 23.4 | 62.5 | 37.1 | ... | 9.5 | 11.2 | 2.7 | 8.5 | 4.9 | ... |
| A-2 | 27.5 | 66.1 | 39.5 | ... | 8.5 | 10.5 | 3.9 | 9.8 | 6.1 | ... |
| ... | ... | ... | ... | ... | ... | ... | ... | ... | ... | ... |

| INDIVIDUAL (SAMPLE) NO. | VISCERAL FAT ACCUMULATION CONDITION INDEX DATA (T) | AMINO ACID CONCENTRATION DATA | | | |
|---|---|---|---|---|---|
| | $T_2$ | Gly | Leu | Phe | ... |
| A-1 | 62.5 | 9.5 | 11.2 | 4.9 | ... |
| A-2 | 66.1 | 8.5 | 10.5 | 6.1 | ... |
| ⋮ | ⋮ | ⋮ | ⋮ | ⋮ | ⋮ |

| RANK | CANDIDATE MULTIVARIATE DISCRIMINANT |
|---|---|
| 1 | $F_1$(Gly, Leu, Phe, ...) |
| 2 | $F_2$(Gly, Leu, Phe, ...) |
| 3 | $F_3$(Gly, Leu, Phe, ...) |
| ⋮ | ⋮ |

| RANK | CANDIDATE MULTIVARIATE DISCRIMINANT | VERIFICATION RESULT |
|---|---|---|
| 1 | $F_k$(Gly, Leu, Phe, ⋯) | 1.22 |
| 2 | $F_m$(Gly, Leu, Phe, ⋯) | 2.28 |
| 3 | $F_l$(Gly, Leu, Phe, ⋯) | 2.95 |
| ⋮ | ⋮ | ⋮ |

| INDIVIDUAL (SAMPLE) NO. | VISCERAL FAT ACCUMULATION CONDITION INDEX DATA (T) | AMINO ACID CONCENTRATION DATA | | |
|---|---|---|---|---|
| | $T_2$ | Leu | Phe | ⋯ |
| A-1 | 62.5 | 11.2 | 4.9 | ⋯ |
| A-2 | 66.1 | 10.5 | 6.1 | ⋯ |
| ⋮ | ⋮ | ⋮ | ⋮ | ⋮ |

| RANK | MULTIVARIATE DISCRIMINANT | THRESHOLD VALUE | VERIFICATION RESULT |
|---|---|---|---|
| 1 | $F_p$(Phe, ⋯) | 0.23 | 0.62 |
| 2 | $F_p$(Gly, Leu, Phe) | -2.12 | 1.02 |
| 3 | $F_k$(Gly, Leu, Phe, ⋯) | 1.23 | 1.22 |
| ⋮ | ⋮ | ⋮ | ⋮ |

FIG.15

| INDIVIDUAL (SAMPLE) NO. | RANK | DISCRIMINANT VALUE |
|---|---|---|
| U-1 | 1 | 1.13 |
| ⋮ | ⋮ | ⋮ |

| INDIVIDUAL (SAMPLE) NO. | AMINO ACID CONCENTRATION DATA | | | | DISCRIMINANT VALUE | EVALUATION RESULT |
|---|---|---|---|---|---|---|
| | Gly | Leu | Phe | ... | | |
| U-1 | 9.5 | 11.2 | 4.9 | ... | | |
| U-2 | 8.5 | 10.5 | 6.1 | ... | | |
| ⋮ | ⋮ | ⋮ | ⋮ | ⋮ | ⋮ | ⋮ |

106g

102h — MULTIVARIATE DISCRIMINANT-PREPARING PART
- 102h1 — CANDIDATE MULTIVARIATE DISCRIMINANT-PREPARING PART
- 102h2 — CANDIDATE MULTIVARIATE DISCRIMINANT-VERIFYING PART
- 102h3 — EXPLANATORY VARIABLE-SELECTING PART

FIG.28

| ROC_AUC | FORMULA |
|---|---|
| 0.832 | (glu+tyr+orn)/(asn+ser) |
| 0.832 | (glu+met+orn)/(asn+ser) |
| 0.831 | (ile+glu+orn)/(asn+ser) |
| 0.828 | (ile+glu+met)/(asn+ser) |
| 0.827 | (leu+glu+orn)/(asn+ser) |
| 0.826 | (leu+glu+met)/(asn+aaba) |
| 0.826 | (ile+glu+orn)/(gly+ser) |
| 0.826 | (ile+glu+arg)/(gly+ser) |
| 0.825 | (ile+leu+glu)/(asn+aaba) |
| 0.825 | (ile+glu+orn)/(aaba+ser) |
| 0.825 | (ile+glu+orn)/(ser) |
| 0.825 | (leu+glu+orn)/(asn+aaba) |
| 0.825 | (glu+tyr+orn)/(ser) |
| 0.824 | (ile+orn+arg)/(gly+ser) |
| 0.824 | (ile+glu+trp)/(asn+ser) |
| 0.823 | (glu+phe+orn)/(asn+ser) |
| 0.822 | (ile+glu+tyr)/(asn+ser) |
| 0.822 | (ile+glu)/(asn+aaba+ser) |
| 0.821 | (ile+glu+phe)/(asn+ser) |
| 0.821 | (leu+glu+sit)/(asn+ser) |
| 0.821 | (leu+glu)/(asn+aaba) |
| 0.820 | (ile+leu+glu)/(asn+ser) |
| 0.820 | (leu+glu+cit)/(asn+aaba) |
| 0.820 | (glu+trp+orn)/(asn+ser) |
| 0.820 | (ile+glu+met)/(ser) |
| 0.820 | (leu+glu)/(asn+ser) |
| 0.819 | (glu+trp+orn)/(aaba+ser) |
| 0.819 | (leu+val+glu)/(asn+aaba) |
| 0.819 | (ile+glu+phe)/(ser) |
| 0.819 | (leu+glu+met)/(asn+ser) |
| 0.819 | (leu+glu+trp)/(asn+ser) |
| 0.819 | (leu+glu)/(asn+aaba+ser) |
| 0.819 | (leu+glu+tyr)/(asn+ser) |
| 0.819 | (val+glu+orn)/(aaba+ser) |
| 0.818 | (glu+orn+arg)/(gly+ser) |
| 0.818 | (leu+glu+orn)/(aaba+ser) |
| 0.818 | (ile+glu+cit)/(asn+ser) |
| 0.818 | (leu+glu+orn)/(gly+ser) |
| 0.818 | (ile+glu+phe)/(gly+ser) |
| 0.818 | (ile+glu)/(asn+ser) |

FIG.29

| CUTTOFF VALUE | SENSITIVITY | SPECIFICITY | POSITIVE PREDICTIVE VALUE | NEGATIVE PREDICTIVE VALUE | DISCRIMINATION RATE |
|---|---|---|---|---|---|
| 0.791 | 1.000 | 0.085 | 0.641 | 1.000 | 0.652 |
| 0.878 | 0.989 | 0.153 | 0.656 | 0.899 | 0.671 |
| 0.931 | 0.989 | 0.220 | 0.674 | 0.928 | 0.697 |
| 0.954 | 0.979 | 0.271 | 0.687 | 0.888 | 0.710 |
| 1.003 | 0.968 | 0.322 | 0.700 | 0.862 | 0.723 |
| 1.015 | 0.947 | 0.356 | 0.706 | 0.806 | 0.723 |
| 1.050 | 0.926 | 0.390 | 0.712 | 0.764 | 0.722 |
| 1.074 | 0.926 | 0.458 | 0.736 | 0.792 | 0.748 |
| 1.094 | 0.916 | 0.508 | 0.752 | 0.787 | 0.761 |
| 1.116 | 0.895 | 0.542 | 0.761 | 0.760 | 0.761 |
| 1.138 | 0.874 | 0.576 | 0.771 | 0.737 | 0.761 |
| 1.156 | 0.832 | 0.576 | 0.762 | 0.677 | 0.735 |
| 1.168 | 0.821 | 0.627 | 0.782 | 0.682 | 0.747 |
| 1.177 | 0.811 | 0.678 | 0.804 | 0.687 | 0.760 |
| 1.188 | 0.789 | 0.712 | 0.817 | 0.675 | 0.760 |
| 1.215 | 0.758 | 0.729 | 0.820 | 0.649 | 0.747 |
| 1.244 | 0.726 | 0.746 | 0.823 | 0.625 | 0.734 |
| 1.265 | 0.705 | 0.780 | 0.839 | 0.619 | 0.734 |
| 1.290 | 0.674 | 0.797 | 0.844 | 0.599 | 0.720 |
| 1.301 | 0.653 | 0.831 | 0.863 | 0.594 | 0.720 |
| 1.319 | 0.632 | 0.864 | 0.884 | 0.590 | 0.720 |
| 1.325 | 0.611 | 0.898 | 0.907 | 0.586 | 0.720 |
| 1.343 | 0.568 | 0.898 | 0.901 | 0.561 | 0.694 |
| 1.362 | 0.526 | 0.898 | 0.894 | 0.538 | 0.668 |
| 1.377 | 0.484 | 0.898 | 0.886 | 0.516 | 0.642 |
| 1.396 | 0.442 | 0.898 | 0.876 | 0.497 | 0.615 |
| 1.405 | 0.421 | 0.932 | 0.910 | 0.497 | 0.615 |
| 1.426 | 0.389 | 0.949 | 0.926 | 0.488 | 0.602 |
| 1.438 | 0.358 | 0.966 | 0.945 | 0.480 | 0.589 |
| 1.460 | 0.316 | 0.966 | 0.938 | 0.464 | 0.563 |
| 1.486 | 0.274 | 0.966 | 0.929 | 0.449 | 0.537 |
| 1.545 | 0.232 | 0.966 | 0.918 | 0.435 | 0.511 |
| 1.619 | 0.189 | 0.966 | 0.901 | 0.422 | 0.485 |
| 1.660 | 0.168 | 1.000 | 1.000 | 0.424 | 0.484 |

FIG.33

| ROC_AUC | FORMULA |
|---|---|
| 0.872 | (Leu+Glu)/(Ser+Tau)+(Pro+Orn)/(Gln) |
| 0.871 | (Leu+Glu)/(Tau+Gly)+(Pro+Orn)/(Gln) |
| 0.871 | (Leu+Glu)/(Ser+Tau)+(Pro+His)/(Gln) |
| 0.871 | (Pro)/(Gln+Ser)+(Leu+Glu)/(Tau+Gly) |
| 0.870 | (Pro)/(Gln)+(Leu+Glu)/(Tau+Gly) |
| 0.870 | (Leu+Glu)/(Ser+Tau)+(Pro+Cys)/(Gln) |
| 0.870 | (Leu+Glu)/(Ser+Tau)+(Pro+Arg)/(Gln) |
| 0.870 | (Leu+Glu)/(Tau+Gly)+(Pro+Cit)/(Gln) |
| 0.870 | (Pro)/(Gln)+(Leu+Glu)/(Ser+Tau+Gly) |
| 0.869 | (Leu+Glu)/(Tau+Gly)+(Ile+Pro)/(Gln) |
| 0.869 | (Pro)/(Gln)+(Leu+Glu+Cit)/(Tau+Gly) |
| 0.869 | (Leu+Glu)/(Ser+Tau)+(Pro+Tyr)/(Gln) |
| 0.868 | (Leu+Glu)/(Tau+Gly)+(Pro+Cys)/(Gln) |
| 0.868 | (Leu+Glu)/(Tau+Gly)+(Pro+Met)/(Gln) |
| 0.867 | (Leu+Glu)/(Ser+Tau)+(Val+Pro)/(Gln) |
| 0.867 | (Pro)/(Gln)+(Leu+Glu+Orn)/(Tau+Gly) |
| 0.867 | (Leu+Glu)/(Tau+Gly)+(Pro+ABA)/(Gln) |
| 0.867 | (Pro)/(Gln)+(Leu+Glu+Cys)/(Tau+Gly) |
| 0.866 | (Leu+Glu)/(Ser+Tau)+(Pro+Orn)/(Gly) |
| 0.866 | (Pro)/(Gly)+(Leu+Glu)/(Ser+Tau) |
| 0.866 | (Glu)/(Tau)+(Leu+Pro+Orn+Cit)/(Gly) |
| 0.866 | (Val)/(Gln)+(Leu+Glu+Pro)/(Tau+Gly) |
| 0.865 | (Leu+Glu)/(Tau+Gly)+(Pro+His)/(Gln) |
| 0.865 | (Leu+Glu)/(Tau+Gly)+(Pro+Asn)/(Gln) |
| 0.865 | (Leu)/(Tau+Gly)+(Glu+Pro)/(Gln+Ser) |
| 0.865 | (Leu+Glu)/(Tau+Gly)+(Pro+Tyr)/(Gln) |
| 0.865 | (Leu)/(Tau+Gly)+(Glu+Pro)/(Gln) |
| 0.864 | (Leu)/(Tau+Gly)+(Glu+Pro+Cit)/(Gln) |
| 0.864 | (Leu+Glu)/(Ser+Tau)+(Pro+Thr)/(Gln) |
| 0.864 | (Leu)/(Ser+Tau+Gly)+(Glu+Pro)/(Gln) |
| 0.864 | (Leu)/(Tau+Gly)+(Glu+Pro+Orn)/(Gln) |
| 0.864 | (Leu+Cit)/(Tau+Gly)+(Glu+Pro)/(Gln) |
| 0.864 | (Leu)/(Tau+Gly)+(Glu+Pro+Cys)/(Gln) |
| 0.864 | (Pro)/(Gln)+(Leu+Glu+Ile)/(Tau+Gly) |
| 0.864 | (Pro)/(Gly)+(Leu+Glu+Orn)/(Ser+Tau) |
| 0.864 | (Leu)/(Ser+Gly)+(Glu+Pro)/(Gln+Tau) |
| 0.864 | (Leu+Glu)/(Ser+Tau)+(Pro+Cys)/(Gly) |
| 0.864 | (Glu)/(Gln)+(Leu+Pro)/(Ser+Tau+Gly) |
| 0.863 | (Leu+Pro)/(Tau+Gly)+(Glu+Val)/(Gln) |
| 0.863 | (Glu)/(Tau)+(Leu+Pro+Orn+Cys)/(Gly) |

FIG.34

| ROC_AUC | FORMULA |
|---|---|
| 0.863 | (Leu+Cys)/(Tau+Gly)+(Glu+Pro)/(Gln) |
| 0.863 | (Leu+Glu)/(Ser+Gly)+(Pro+Orn)/(Gln) |
| 0.863 | (Leu+Pro)/(Gln)+(Glu+Orn)/(Tau+Gly) |
| 0.862 | (Leu+Pro)/(Gln)+(Glu+Ile)/(Tau+Gly) |
| 0.862 | (Leu+Orn)/(Ser+Gly)+(Glu+Pro)/(Gln) |
| 0.862 | (Leu)/(Tau+Gly)+(Glu+Ile+Pro)/(Gln) |
| 0.862 | (Glu)/(Tau)+(Leu+Pro+Orn)/(Gly) |
| 0.862 | (Leu)/(Ser+Tau)+(Glu+Pro+Orn)/(Gln) |
| 0.862 | (Glu)/(Tau)+(Leu+Ile+Pro+Orn)/(Gly) |
| 0.862 | (Leu+Orn)/(Tau+Gly)+(Glu+Pro)/(Gln) |
| 0.861 | (Leu+Glu+Pro+Orn)/(Ser+Tau+Gly) |
| 0.861 | (Leu)/(Ser+Gly)+(Glu+Pro+Orn)/(Gln) |
| 0.861 | (Glu)/(Tau)+(Leu+Pro+Orn+ABA)/(Gly) |
| 0.861 | (Pro)/(Gln)+(Leu+Glu+Met)/(Tau+Gly) |
| 0.861 | (Leu+Glu)/(Tau+Gly)+(Pro+Phe)/(Gln) |
| 0.861 | (Leu)/(Gln)+(Glu+Ile+Pro)/(Tau+Gly) |
| 0.861 | (Leu)/(Ser+Gly)+(Glu+Pro)/(Gln) |
| 0.861 | (Leu+Glu)/(Tau+Gly)+(Pro+Trp)/(Gln) |
| 0.860 | (Glu)/(Tau)+(Leu+Pro+Orn+Arg)/(Gly) |
| 0.860 | (Leu)/(Gln)+(Glu+Pro)/(Ser+Tau+Gly) |
| 0.860 | (Leu+Glu)/(Tau+Gly)+(Pro+Arg)/(Gln) |
| 0.860 | (Glu)/(Tau)+(Leu+Pro+Orn+Asn)/(Gly) |
| 0.860 | (Pro)/(Gln)+(Leu+Glu+Asn)/(Tau+Gly) |
| 0.860 | (Glu)/(Tau)+(Leu+Ile+Pro+Cys)/(Gly) |
| 0.859 | (Orn)/(Gln)+(Leu+Glu+Pro)/(Tau+Gly) |
| 0.859 | (Glu)/(Tau)+(Leu+Pro+Orn+Met)/(Gly) |
| 0.859 | (Leu)/(Tau+Gly)+(Glu+Pro+ABA)/(Gln) |
| 0.859 | (Glu)/(Tau)+(Leu+Pro+Orn+His)/(Gly) |
| 0.859 | (Ile)/(Gln)+(Leu+Glu+Pro)/(Tau+Gly) |
| 0.859 | (Leu)/(Tau+Gly)+(Glu+Pro+Met)/(Gln) |
| 0.859 | (Leu)/(Tau+Gly)+(Glu+Pro+Asn)/(Gln) |
| 0.858 | (Leu)/(Tau+Gly)+(Glu+Pro+His)/(Gln) |
| 0.858 | (Leu+Ile)/(Gln)+(Glu+Pro)/(Tau+Gly) |
| 0.858 | (Leu+Val)/(Gln)+(Glu+Pro)/(Tau+Gly) |
| 0.858 | (Leu+Glu)/(Tau+Gly)+(Pro+Thr)/(Gln) |
| 0.858 | (Leu)/(Ser+Gly)+(Glu+Pro+Cys)/(Gln) |
| 0.858 | (Leu)/(Gln)+(Glu+Pro+Orn)/(Tau+Gly) |
| 0.857 | (Leu+Met)/(Tau+Gly)+(Glu+Pro)/(Gln) |
| 0.857 | (Pro)/(Gln)+(Glu+Ile+Orn)/(Tau+Gly) |
| 0.857 | (Glu)/(Tau)+(Leu+Pro+Tyr+Orn)/(Gly) |

FIG.35

| ROC_AUC | FORMULA |
|---|---|
| 0.856 | (Leu)/(Tau+Gly)+(Pro+Orn)/(Gln+Ser) |
| 0.856 | (Leu+Pro)/(Tau+Gly)+(Glu+Orn)/(Gln) |
| 0.855 | (Pro)/(Gln)+(Leu+Orn)/(Ser+Tau+Gly) |
| 0.855 | (Leu)/(Tau+Gly)+(Glu+Pro+Tyr)/(Gln) |
| 0.855 | (Leu+Orn)/(Gln)+(Glu+Pro)/(Tau+Gly) |
| 0.855 | (Leu+Asn)/(Tau+Gly)+(Glu+Pro)/(Gln) |
| 0.855 | (Lys)/(Gln)+(Leu+Glu+Pro)/(Tau+Gly) |
| 0.854 | (Leu+Glu+Pro+Orn)/(Gln+Ser+Gly) |
| 0.853 | (Pro)/(Ser+Tau+Gly)+(Leu+Glu)/(Gln) |
| 0.853 | (Leu+Cys)/(Tau+Gly)+(Pro+Orn)/(Gln) |
| 0.852 | (Leu+Glu)/(Gln)+(Pro+Orn)/(Tau+Gly) |
| 0.852 | (Glu+Orn)/(Tau+Gly)+(Ile+Pro)/(Gln) |
| 0.851 | (Leu+Glu+Ile+Pro)/(Gln+Tau+Gly) |
| 0.850 | (Leu)/(Tau+Gly)+(Glu+Pro+Arg)/(Gln) |
| 0.850 | (Leu+Glu+Pro+Orn)/(Gln+Tau+Gly) |
| 0.850 | (Glu+Pro)/(Gln)+(Ile+Orn)/(Tau+Gly) |
| 0.850 | (Leu+Glu+Pro)/(Gln+Ser+Tau+Gly) |
| 0.850 | (Leu+Glu+Pro)/(Gln+Tau+Gly) |
| 0.849 | (Leu+Glu+Pro+Cys)/(Gln+Tau+Gly) |
| 0.842 | (Leu+Glu+Pro+Tyr)/(Gln+Tau+Gly) |

FIG.36

| CUTTOFF VALUE | SENSITIVITY | SPECIFICITY | POSITIVE PREDICTIVE VALUE | NEGATIVE PREDICTIVE VALUE | DISCRIMINATION RATE |
|---|---|---|---|---|---|
| 0.823 | 1.000 | 0.014 | 0.643 | 1.000 | 0.645 |
| 0.835 | 0.992 | 0.028 | 0.645 | 0.668 | 0.645 |
| 1.042 | 0.984 | 0.236 | 0.696 | 0.895 | 0.715 |
| 1.070 | 0.977 | 0.292 | 0.710 | 0.876 | 0.730 |
| 1.101 | 0.969 | 0.333 | 0.721 | 0.858 | 0.740 |
| 1.128 | 0.961 | 0.389 | 0.737 | 0.849 | 0.755 |
| 1.143 | 0.953 | 0.444 | 0.753 | 0.843 | 0.770 |
| 1.148 | 0.938 | 0.458 | 0.755 | 0.806 | 0.765 |
| 1.163 | 0.930 | 0.472 | 0.758 | 0.792 | 0.765 |
| 1.178 | 0.922 | 0.500 | 0.766 | 0.784 | 0.770 |
| 1.197 | 0.907 | 0.528 | 0.773 | 0.761 | 0.770 |
| 1.212 | 0.899 | 0.569 | 0.788 | 0.761 | 0.781 |
| 1.245 | 0.891 | 0.639 | 0.814 | 0.768 | 0.801 |
| 1.254 | 0.876 | 0.653 | 0.818 | 0.748 | 0.796 |
| 1.272 | 0.837 | 0.667 | 0.817 | 0.697 | 0.776 |
| 1.279 | 0.829 | 0.708 | 0.835 | 0.700 | 0.786 |
| 1.300 | 0.806 | 0.736 | 0.845 | 0.681 | 0.781 |
| 1.313 | 0.791 | 0.750 | 0.849 | 0.668 | 0.776 |
| 1.330 | 0.783 | 0.778 | 0.862 | 0.668 | 0.781 |
| 1.345 | 0.775 | 0.792 | 0.869 | 0.665 | 0.781 |
| 1.386 | 0.744 | 0.819 | 0.880 | 0.643 | 0.771 |
| 1.400 | 0.705 | 0.833 | 0.883 | 0.614 | 0.751 |
| 1.440 | 0.674 | 0.875 | 0.906 | 0.602 | 0.747 |
| 1.477 | 0.605 | 0.889 | 0.906 | 0.558 | 0.707 |
| 1.492 | 0.589 | 0.917 | 0.926 | 0.557 | 0.707 |
| 1.510 | 0.543 | 0.931 | 0.933 | 0.534 | 0.682 |
| 1.554 | 0.481 | 0.944 | 0.939 | 0.506 | 0.648 |
| 1.569 | 0.465 | 0.958 | 0.952 | 0.502 | 0.643 |
| 1.672 | 0.333 | 0.972 | 0.955 | 0.451 | 0.563 |
| 1.694 | 0.318 | 0.986 | 0.976 | 0.448 | 0.558 |
| 1.804 | 0.256 | 1.000 | 1.000 | 0.430 | 0.524 |

FIG.37

| No | FORMULA | AIC |
|---|---|---|
| 1 | (3.754e+01)+(9.243e-01)Glu-(5.335e-01)Ser+(2.326e-01)Pro+(5.255e-01)Tyr+(8.792e-01)Leu-(1.226e+00)Trp | 2114.58 |
| 2 | (3.977e+01)+(8.181e-01)Glu+(2.705e-01)Pro-(1.251e-01)Gln+(6.407e-01)Tyr+(8.393e-01)Leu-(1.119e+00)Trp | 2115.767 |
| 3 | (9.657e+01)+(9.504e-01)Glu-(4.922e-01)Ser-(9.540e-02)Gln+(6.932e-01)Tyr+(9.462e-01)Leu-(1.176e+00)Trp | 2116.058 |
| 4 | (9.505e+01)+(8.336e-01)Glu-(4.858e-01)Ser+(2.891e-01)Pro-(8.855e-02)Gln+(9.620e-01)Leu-(1.021e+00)Trp | 2116.117 |
| 5 | (7.715e+01)+(8.435e-01)Glu-(3.916e-01)Ser+(2.701e-01)Pro-(1.361e-01)Gly+(8.904e-01)Leu-(1.041e+00)Trp | 2117.417 |
| 6 | (8.863e+01)+(7.466e-01)Glu+(3.030e-01)Pro-(1.753e-01)Gly-(8.456e-02)Gln+(8.567e-01)Leu-(9.346e-01)Trp | 2117.888 |
| 7 | (3.128e+01)+(8.405e-01)Glu+(2.533e-01)Pro-(1.720e-01)Gly+(4.020e-01)Tyr+(7.905e-01)Leu-(1.103e+00)Trp | 2118.818 |
| 8 | (4.364e+01)+(9.257e-01)Glu-(5.283e-01)Ser+(2.076e-01)Pro+(6.855e-01)Ala+(9.198e-01)Leu-(1.136e+00)Trp | 2118.897 |
| 9 | (9.221e+01)+(9.268e-01)Glu-(4.905e-01)Ser-(8.840e-02)Gln+(1.205e-01)Ala+(9.650e-01)Leu-(1.085e+00)Trp | 2118.971 |
| 10 | (4.239e+01)+(1.013e+00)Glu-(5.348e-01)Ser+(7.255e-02)Ala+(4.721e-01)Tyr+(9.087e-01)Leu-(1.248e+00)Trp | 2119.21 |
| 11 | (4.600e+01)+(9.371e-01)Glu-(5.414e-01)Ser+(2.430e-01)Pro+(2.860e-01)Orn+(9.291e-01)Leu-(1.136e+00)Trp | 2119.592 |
| 12 | (4.420e+01)+(1.041e+00)Glu-(5.506e-01)Ser+(5.633e-01)Tyr+(3.148e-01)Orn+(9.178e-01)Leu-(1.270e+00)Trp | 2119.859 |
| 13 | (4.100e+01)+(8.198e-01)Glu+(2.243e-01)Pro-(1.991e-01)Gly+(6.966e-02)Ala+(8.017e-01)Leu-(1.037e+00)Trp | 2120.042 |
| 14 | (6.669e+01)+(8.484e-01)Glu+(3.075e-01)Pro-(1.856e-01)Gly-(2.429e-01)Thr+(8.291e-01)Leu-(9.167e-01)Trp | 2120.17 |
| 15 | (6.913e+01)+(9.371e-01)Glu-(5.224e-01)Ser+(2.522e-01)Pro-(2.986e-01)Tau+(9.406e-01)Leu-(1.063e+00)Trp | 2120.349 |
| 16 | (6.811e+01)+(8.635e-01)Glu+(2.665e-01)Pro-(2.083e-01)Gly-(8.573e-01)ABA+(8.840e-01)Leu-(1.041e+00)Trp | 2120.403 |
| 17 | (6.669e+01)+(9.472e-01)Glu-(5.400e-01)Ser+(2.648e-01)Pro-(3.618e-01)Cit+(9.648e-01)Leu-(1.170e+00)Trp | 2120.442 |
| 18 | (4.445e+01)+(9.612e-01)Glu-(5.479e-01)Ser+(2.606e-01)Pro+(9.802e-02)Lys+(8.959e-01)Leu-(1.135e+00)Trp | 2120.448 |
| 19 | (5.276e+01)+(9.012e-01)Glu-(5.073e-01)Ser+(2.543e-01)Pro+(3.223e-01)Ile+(7.943e-01)Leu-(1.094e+00)Trp | 2120.5 |
| 20 | (7.059e+01)+(1.045e+00)Glu-(5.299e-01)Ser-(3.482e-01)Tau+(5.864e-01)Tyr+(9.259e-01)Leu-(1.194e+00)Trp | 2120.636 |
| 21 | (7.439e+01)+(9.383e-01)Glu-(4.035e-01)Ser-(1.279e-01)Gly+(1.066e-01)Ala+(9.015e-01)Leu-(1.100e+00)Trp | 2120.643 |
| 22 | (5.945e+01)+(9.432e-01)Glu-(4.771e-01)Ser+(2.765e-01)Pro-(1.378e-01)Thr+(9.440e-01)Leu-(1.061e+00)Trp | 2120.684 |
| 23 | (6.978e+01)+(9.965e-01)Glu-(4.519e-01)Ser-(8.137e-02)Gly+(5.364e-01)Tyr+(9.168e-01)Leu-(1.184e+00)Trp | 2120.702 |
| 24 | (5.228e+01)+(7.812e-01)Glu+(2.704e-01)Pro-(1.975e-01)Gly+(4.569e-01)Ile+(6.120e-01)Leu-(9.967e-01)Trp | 2120.797 |
| 25 | (4.339e+01)+(8.291e-01)Glu+(2.510e-01)Pro-(2.033e-01)Gly+(2.827e-01)Orn+(8.092e-01)Leu-(1.033e+00)Trp | 2120.855 |
| 26 | (5.163e+01)+(1.005e+00)Glu-(5.126e-01)Ser+(5.890e-01)Tyr+(3.703e-01)Ile+(7.585e-01)Leu-(1.230e+00)Trp | 2120.879 |
| 27 | (5.732e+01)+(9.492e-01)Glu-(5.099e-01)Ser+(2.542e-01)Pro-(2.974e-01)ABA+(9.717e-01)Leu-(1.110e+00)Trp | 2121.128 |
| 28 | (5.042e+01)+(9.476e-01)Glu-(5.453e-01)Ser+(2.559e-01)Pro+(7.918e-02)Arg+(9.480e-01)Leu-(1.104e+00)Trp | 2121.151 |
| 29 | (5.293e+01)+(9.353e-01)Glu-(5.342e-01)Ser+(2.525e-01)Pro+(1.842e-01)Met+(9.491e-01)Leu-(1.114e+00)Trp | 2121.276 |
| 30 | (5.820e+01)+(1.068e+00)Glu-(5.075e-01)Ser-(5.096e-01)ABA+(5.957e-01)Tyr+(9.697e-01)Leu-(1.260e+00)Trp | 2121.286 |
| 31 | (5.292e+01)+(9.198e-01)Glu-(5.283e-01)Ser+(2.542e-01)Pro+(3.378e-02)Val+(9.147e-01)Leu-(1.104e+00)Trp | 2121.304 |
| 32 | (5.148e+01)+(9.355e-01)Glu-(5.295e-01)Ser+(2.545e-01)Pro+(5.687e-02)His+(9.514e-01)Leu-(1.097e+00)Trp | 2121.315 |
| 33 | (4.115e+01)+(1.014e+00)Glu-(5.495e-01)Ser+(1.024e-01)Ala+(3.557e-01)Orn+(9.232e-01)Leu-(1.201e+00)Trp | 2121.319 |
| 34 | (5.125e+01)+(9.318e-01)Glu-(5.224e-01)Ser+(2.560e-01)Pro+(9.442e-01)Leu+(8.345e-02)Phe-(1.111e+00)Trp | 2121.32 |
| 35 | (5.542e+01)+(9.306e-01)Glu-(5.199e-01)Ser+(2.593e-01)Pro-(1.663e-02)Asn+(9.550e-01)Leu-(1.091e+00)Trp | 2121.381 |
| 36 | (5.425e+01)+(9.330e-01)Glu-(5.246e-01)Ser+(2.575e-01)Pro+(9.554e-01)Leu-(1.093e+00)Trp | 2121.388 |
| 37 | (7.141e+01)+(7.968e-01)Glu+(2.959e-01)Pro-(5.646e-01)Asn-(1.948e-01)Gly+(8.382e-01)Leu-(9.694e-01)Trp | 2121.429 |
| 38 | (8.405e+01)+(8.509e-01)Glu-(1.683e-01)Gly-(8.463e-02)Gln+(1.229e-01)Ala+(8.648e-01)Leu-(1.001e+00)Trp | 2121.467 |
| 39 | (4.110e+01)+(9.279e-01)Glu-(1.178e-01)Gln+(8.753e-02)Ala+(5.653e-01)Tyr+(8.716e-01)Leu-(1.149e+00)Trp | 2121.543 |
| 40 | (4.883e+01)+(1.061e+00)Glu-(5.579e-01)Ser+(9.734e-02)Arg+(5.871e-01)Tyr+(9.353e-01)Leu-(1.242e+00)Trp | 2121.693 |
| 41 | (4.086e+01)+(8.354e-01)Glu+(2.350e-01)Pro-(1.113e-01)Gln+(8.379e-01)Ala+(8.878e-01)Leu-(1.021e+00)Trp | 2121.784 |
| 42 | (4.935e+01)+(1.059e+00)Glu-(5.438e-01)Ser+(5.747e-01)Tyr-(4.910e-02)Lys+(9.178e-01)Leu-(1.247e+00)Trp | 2121.819 |
| 43 | (5.776e+01)+(1.046e+00)Glu-(5.363e-01)Ser+(6.116e-01)Tyr+(9.598e-01)Leu-(1.325e-01)Phe+(1.206e+00)Trp | 2121.893 |
| 44 | (5.889e+01)+(1.051e+00)Glu-(5.380e-01)Ser-(1.361e-01)Cit+(5.787e-01)Tyr+(9.509e-01)Leu-(1.255e+00)Trp | 2121.918 |
| 45 | (6.257e+01)+(8.348e-01)Glu+(2.701e-01)Pro-(1.925e-01)Gly-(2.403e-01)Tau+(8.290e-01)Leu-(9.715e-01)Trp | 2121.934 |
| 46 | (5.437e+01)+(1.043e+00)Glu-(5.245e-01)Ser+(6.099e-01)Tyr-(1.590e-01)Met+(9.483e-01)Leu-(1.216e+00)Trp | 2121.977 |
| 47 | (4.982e+01)+(1.049e+00)Glu-(5.470e-01)Ser+(1.456e-01)Asn+(5.805e-01)Tyr+(9.458e-01)Leu-(1.235e+00)Trp | 2121.978 |
| 48 | (5.114e+01)+(1.045e+00)Glu-(5.369e-01)Ser+(5.305e-02)His+(5.803e-01)Tyr+(9.416e-01)Leu-(1.231e+00)Trp | 2121.988 |
| 49 | (5.300e+01)+(1.036e+00)Glu-(5.344e-01)Ser+(5.814e-01)Tyr+(1.902e-02)Val+(9.225e-01)Leu-(1.233e+00)Trp | 2122.024 |
| 50 | (5.425e+01)+(1.046e+00)Glu-(5.283e-01)Ser-(1.182e-02)Thr+(5.876e-01)Tyr+(9.446e-01)Leu-(1.226e+00)Trp | 2122.045 |

FIG.38

| No | FORMULA | AIC |
|---|---|---|
| 51 | (5.368e+01)+(1.044e+00)Glu-(5.324e-01)Ser+(5.874e-01)Tyr+(9.450e-01)Leu-(1.229e+00)Trp | 2122.05 |
| 52 | (4.632e+01)+(7.808e-01)Glu+(2.840e-01)Pro-(1.222e-01)Gln+(7.232e-01)Tyr+(1.149e+00)Ile-(9.232e-01)Trp | 2122.097 |
| 53 | (7.185e+01)+(1.017e+00)Glu-(5.253e-01)Ser-(4.183e-01)Tau+(1.083e-01)Ala+(9.343e-01)Leu-(1.109e+00)Trp | 2122.102 |
| 54 | (4.360e+01)+(8.478e-01)Glu+(2.773e-01)Pro-(2.001e-01)Gly+(7.060e-02)Lys+(7.937e-01)Leu-(1.023e+00)Trp | 2122.106 |
| 55 | (7.946e+01)+(9.103e-01)Glu-(1.221e-01)Gly-(9.220e-02)Gln+(6.027e-01)Tyr+(8.801e-01)Leu-(1.082e+00)Trp | 2122.143 |
| 56 | (4.889e+01)+(9.671e-01)Glu-(5.042e-01)Ser+(1.092e-01)Ala+(4.617e-01)Ile+(7.245e-01)Leu-(1.153e+00)Trp | 2122.327 |
| 57 | (2.482e+00)+(9.787e-01)Glu+(2.725e-01)Pro-(2.913e-01)Thr+(5.082e-01)Tyr+(8.283e-01)Leu-(1.123e+00)Trp | 2122.405 |
| 58 | (6.829e+01)+(1.012e+00)Glu-(1.155e-01)Gln-(1.019e+00)ABA+(7.200e-01)Tyr+(9.680e-01)Leu-(1.193e+00)Trp | 2122.472 |
| 59 | (4.912e+01)+(8.283e-01)Glu+(2.735e-01)Pro-(1.957e-01)Gly+(8.309e-01)Leu+(6.496e-02)Phe-(1.008e+00)Trp | 2122.557 |
| 60 | (6.599e+01)+(8.745e-01)Glu+(3.268e-01)Pro-(9.568e-02)Gln-(2.621e-01)Thr+(9.143e-01)Leu-(9.262e-01)Trp | 2122.565 |
| 61 | (5.219e+01)+(8.280e-01)Glu+(2.763e-01)Pro-(1.963e-01)Gly-(5.805e-02)Met+(8.415e-01)Leu-(9.880e-01)Trp | 2122.587 |
| 62 | (5.122e+01)+(8.262e-01)Glu+(2.741e-01)Pro-(1.967e-01)Gly+(6.372e-03)Val+(8.314e-01)Leu-(9.961e-01)Trp | 2122.595 |
| 63 | (5.121e+01)+(8.276e-01)Glu+(2.745e-01)Pro-(1.973e-01)Gly+(1.645e-02)Cit+(8.385e-01)Leu-(9.905e-01)Trp | 2122.596 |
| 64 | (5.194e+01)+(8.276e-01)Glu+(2.749e-01)Pro-(1.964e-01)Gly-(6.344e-03)Arg+(8.399e-01)Leu-(9.935e-01)Trp | 2122.596 |
| 65 | (5.167e+01)+(8.286e-01)Glu+(2.749e-01)Pro-(1.966e-01)Gly-(2.534e-03)His+(8.393e-01)Leu-(9.940e-01)Trp | 2122.598 |
| 66 | (5.153e+01)+(8.287e-01)Glu+(2.748e-01)Pro-(1.967e-01)Gly+(8.391e-01)Leu-(9.942e-01)Trp | 2122.598 |
| 67 | (5.072e+01)+(7.486e-01)Glu+(2.177e-01)Pro-(2.190e-01)Gly+(9.935e-02)Ala+(1.146e+00)Ile-(8.716e-01)Trp | 2122.991 |
| 68 | (4.729e+01)+(8.555e-01)Glu-(1.921e-01)Gly+(1.149e-01)Ala+(6.028e-01)Ile+(5.422e-01)Leu-(1.060e+00)Trp | 2123.001 |
| 69 | (4.311e+01)+(7.839e-01)Glu+(2.672e-01)Pro-(1.882e-01)Gly+(4.681e-01)Tyr+(1.103e+00)Ile-(9.215e-01)Trp | 2123.132 |
| 70 | (5.934e+01)+(6.597e-01)Glu-(4.529e-01)Ser+(2.723e-01)Pro-(1.251e-01)Gln+(5.050e-01)Tyr+(6.314e-01)Leu | 2123.237 |
| 71 | (3.702e+01)+(9.169e-01)Glu-(1.992e-01)Gly+(1.062e-01)Ala+(3.557e-01)Orn+(8.070e-01)Leu-(1.101e+00)Trp | 2123.299 |
| 72 | (7.400e+01)+(9.713e-01)Glu-(1.128e-01)Gln-(4.339e-01)Tau+(6.977e-01)Tyr+(8.919e-01)Leu-(1.085e+00)Trp | 2123.408 |
| 73 | (4.115e+01)+(9.692e-01)Glu-(1.118e-01)Gln+(6.742e-01)Tyr+(3.012e-01)Orn+(8.853e-01)Leu-(1.168e+00)Trp | 2123.582 |
| 74 | (4.960e+01)+(9.248e-01)Glu-(1.066e-01)Gln+(6.948e-01)Tyr-(4.739e-01)Ile+(6.781e-01)Leu-(1.136e+00)Trp | 2123.642 |
| 75 | (6.324e+01)+(8.891e-01)Glu+(2.855e-01)Pro-(1.055e-01)Gln-(7.608e-01)ABA+(9.750e-01)Leu-(1.019e+00)Trp | 2123.656 |
| 76 | (3.730e+01)+(8.984e-01)Glu-(4.495e-01)Ser+(2.499e-01)Pro+(6.176e-01)Tyr+(1.155e+00)Ile-(9.977e-01)Trp | 2123.699 |
| 77 | (3.456e+01)+(9.376e-01)Glu-(1.687e-01)Gly+(8.426e-02)Ala+(3.375e-01)Tyr+(8.208e-01)Leu-(1.129e+00)Trp | 2123.706 |
| 78 | (4.731e+01)+(1.038e+00)Glu-(5.426e-01)Ser+(1.007e-01)Ala+(4.036e-02)Lys+(9.271e-01)Leu-(1.172e+00)Trp | 2123.762 |
| 79 | (6.984e+01)+(8.563e-01)Glu+(2.869e-01)Pro-(1.048e-01)Gln-(3.722e-01)Tau+(9.126e-01)Leu-(9.369e-01)Trp | 2123.797 |
| 80 | (4.134e+01)+(8.570e-01)Glu+(2.798e-01)Pro-(1.044e-01)Gln-(2.678e-01)Orn+(9.051e-01)Leu-(1.013e+00)Trp | 2123.828 |
| 81 | (6.730e+00)-(9.199e-01)Glu+(2.588e-01)Pro-(7.525e-01)Asn+(5.411e-01)Tyr+(8.387e-01)Leu-(1.159e+00)Trp | 2123.865 |
| 82 | (4.882e+01)+(8.145e-01)Glu+(2.876e-01)Pro-(9.959e-02)Gln+(4.192e-01)Ile+(7.224e-01)Leu-(9.807e-01)Trp | 2123.88 |
| 83 | (5.561e+01)+(1.032e+00)Glu-(5.152e-01)Ser+(1.012e-01)Ala-(2.661e-01)ABA+(9.764e-01)Leu-(1.161e+00)Trp | 2123.906 |
| 84 | (5.910e+01)+(1.027e+00)Glu-(5.355e-01)Ser-(1.683e-01)Cit+(1.014e-01)Ala+(9.681e-01)Leu-(1.182e+00)Trp | 2123.909 |
| 85 | (9.744e+01)+(9.950e-01)Glu-(5.132e-01)Ser-(7.329e-02)Gln+(3.944e-01)Orn+(1.010e+00)Leu-(1.077e+00)Trp | 2123.953 |
| 86 | (4.984e+01)+(1.029e+00)Glu-(5.447e-01)Ser+(1.019e-01)Ala+(6.231e-02)Arg+(9.561e-01)Leu-(1.155e+00)Trp | 2123.966 |
| 87 | (5.506e+01)+(1.025e+00)Glu-(5.086e-01)Ser-(5.784e-02)Thr+(1.052e-01)Ala+(9.576e-01)Leu-(1.135e+00)Trp | 2123.982 |
| 88 | (5.148e+01)+(1.004e+00)Glu-(5.321e-01)Ser+(1.014e-01)Ala+(3.331e-02)Val+(9.214e-01)Leu-(1.157e+00)Trp | 2124.031 |
| 89 | (6.494e+01)+(9.580e-01)Glu-(2.013e-01)Gly+(1.008e-01)Ala-(8.278e-01)ABA+(8.954e-01)Leu-(1.094e+00)Trp | 2124.061 |
| 90 | (5.221e+01)+(1.019e+00)Glu-(5.330e-01)Ser+(1.014e-01)Ala+(9.030e-02)Met+(9.588e-01)Leu-(1.156e+00)Trp | 2124.085 |
| 91 | (5.401e+01)+(1.016e+00)Glu-(5.256e-01)Ser-(3.433e-02)His+(1.054e-01)Ala+(9.626e-01)Leu-(1.146e+00)Trp | 2124.086 |
| 92 | (5.102e+01)+(1.017e+00)Glu-(5.271e-01)Ser+(1.025e-01)Ala+(9.551e-01)Leu+(4.793e-02)Phe-(1.157e+00)Trp | 2124.088 |
| 93 | (5.103e+01)+(1.020e+00)Glu-(5.350e-01)Ser+(6.505e-02)Asn+(1.022e-01)Ala+(9.619e-01)Leu-(1.150e+00)Trp | 2124.096 |
| 94 | -(1.903e+01)+(9.176e-01)Glu+(2.272e-01)Pro+(5.146e-01)Tyr+(4.590e-01)Ile+(6.170e-01)Leu-(1.188e+00)Trp | 2124.104 |
| 95 | (5.265e+01)+(1.018e+00)Glu-(5.284e-01)Ser+(1.033e-01)Ala+(9.613e-01)Leu-(1.148e+00)Trp | 2124.11 |
| 96 | (8.426e+01)+(9.858e-01)Glu-(4.202e-01)Ser-(1.276e-01)Gly+(3.865e-01)Orn+(9.402e-01)Leu-(1.088e+00)Trp | 2124.124 |
| 97 | -(1.340e+01)+(9.514e-01)Glu+(2.473e-01)Pro+(6.120e-01)Tyr-(7.382e-01)Met+(8.587e-01)Leu-(1.131e+00)Trp | 2124.319 |
| 98 | -(8.774e+00)+(1.000e+00)Glu+(2.233e-01)Pro-(7.128e-01)ABA+(5.256e-01)Tyr+(8.845e-01)Leu-(1.231e+00)Trp | 2124.384 |
| 99 | (6.200e+01)+(1.018e+00)Glu-(1.679e-01)Gly-(1.012e+00)ABA+(4.899e-01)Tyr+(9.155e-01)Leu-(1.173e+00)Trp | 2124.391 |
| 100 | (8.640e+01)+(7.889e-01)Glu+(3.337e-01)Pro-(2.035e-01)Gly-(3.076e-01)Thr+(1.178e+00)Ile-(7.292e-01)Trp | 2124.401 |

FIG.39

| No | FORMULA | SSR-test |
|---|---|---|
| 1 | (Ile)/(Tau+Gly)+(Glu+Pro+Tyr)/(Ser+Gln) | 1744.502 |
| 2 | (Ile)/(Asn+Tau)+(Ala)/(Gln)+(Glu+Pro)/(Gly) | 1746.216 |
| 3 | (Glu+Pro)/(Gln)+(Leu+Tyr)/(Tau+Ser+Gly) | 1757.032 |
| 4 | (Glu+Leu)/(Tau+Ser+Gly)+(Pro+Tyr)/(Gln) | 1759.479 |
| 5 | (Ile)/(Tau+Gly)+(Glu+Pro+Tyr)/(Asn+Gln) | 1759.612 |
| 6 | (Glu+Pro)/(Gln)+(Ile+Tyr)/(Asn+Tau+Gly) | 1760.175 |
| 7 | (Leu)/(Asn+Tau+Gly)+(Glu+Pro+Tyr)/(Gln) | 1760.376 |
| 8 | (Leu)/(Tau+Ser+Gly)+(Glu+Pro+Tyr)/(Gln) | 1760.974 |
| 9 | (Glu+Leu)/(Asn+Tau+Gly)+(Pro+Tyr)/(Gln) | 1763.593 |
| 10 | (Ile)/(Asn+Gly)+(Glu+Pro+Tyr)/(Ser+Gln) | 1765.999 |
| 11 | (Ile)/(Tau+Gly)+(Glu+Pro+Tyr)/(Arg+Gln) | 1766.773 |
| 12 | (Leu)/(Tau+Gly)+(Glu+Pro+Tyr)/(Gln) | 1768.427 |
| 13 | (Glu+Pro)/(Gln)+(Ile+Tyr)/(Tau+Ser+Gly) | 1768.46 |
| 14 | (Ile)/(Asn+Tau)+(Pro)/(Gly)+(Glu+Ala)/(Gln) | 1768.7 |
| 15 | (Ile)/(Asn+Gly)+(Glu+Pro+Tyr)/(Tau+Gln) | 1769.138 |
| 16 | (Leu)/(Tau+Gly)+(Glu+Pro+Tyr)/(Asn+Gln) | 1770.121 |
| 17 | (Ile)/(Gly)+(Glu+Pro+Tyr)/(Asn+Tau+Gln) | 1770.257 |
| 18 | (Ile)/(Asn+Tau)+(Ala)/(Gln)+(Pro+Orn)/(Gly) | 1771.329 |
| 19 | (Leu)/(Ser+Gly)+(Glu+Pro+Tyr)/(Tau+Gln) | 1771.672 |
| 20 | (Glu+Leu+Pro+Tyr)/(Tau+Ser+Gln+Gly) | 1771.885 |
| 21 | (Ile)/(Gly)+(Glu+Pro+Tyr)/(Tau+Gln) | 1772.674 |
| 22 | (Glu+Ile)/(Tau+Gly)+(Pro+Tyr)/(Asn+Gln) | 1773.427 |
| 23 | (Ile)/(Asn+Tau)+(Ala)/(Gln)+(Pro+Tyr)/(Gly) | 1773.715 |
| 24 | (Leu)/(Tau+Gly)+(Glu+Pro+Tyr)/(Ser+Gln) | 1773.822 |
| 25 | (Ile)/(Gly)+(Glu+Pro+Tyr)/(Tau+Ser+Gln) | 1774.286 |
| 26 | (Glu+Ile)/(Tau+Gly)+(Pro+Tyr)/(Ser+Gln) | 1774.421 |
| 27 | (Glu+Ile)/(Asn+Tau+Gly)+(Pro+Tyr)/(Gln) | 1774.56 |
| 28 | (Pro)/(Gln)+(Glu+Ile+Tyr)/(Asn+Tau+Gly) | 1774.565 |
| 29 | (Glu+Ile)/(Tau+Gly)+(Pro+Tyr)/(Gln) | 1775.733 |
| 30 | (Ile)/(Tau+Gly)+(Glu+Pro+Tyr)/(Gln) | 1776.588 |
| 31 | (Glu+Pro)/(Gln)+(Leu+Tyr)/(Asn+Tau+Gly) | 1776.714 |
| 32 | (Glu+Pro)/(Gln)+(Ile+Tyr)/(Tau+Gly) | 1777.155 |
| 33 | (Ile)/(Gly)+(Glu+Pro+Tyr)/(Ser+Gln) | 1778.117 |
| 34 | (Pro)/(Gly)+(Ala)/(Gln)+(Glu+Ile)/(Asn+Tau) | 1778.281 |
| 35 | (Pro)/(Gln)+(Glu+Leu+Tyr)/(Tau+Ser+Gly) | 1778.499 |
| 36 | (Glu+Pro)/(Gln)+(Leu+Cit)/(Asn+Tau+Gly) | 1778.854 |
| 37 | (Ile)/(Tau+Gly)+(Glu+Pro+His)/(Ser+Gln) | 1778.948 |
| 38 | (Ile)/(Gly)+(Glu+Pro+Tyr)/(Asn+Ser+Gln) | 1779.162 |
| 39 | (Ile)/(Gly)+(Glu+Pro+Tyr)/(Asn+Gln) | 1779.74 |
| 40 | (Glu+Tyr)/(Tau+Ser+Gly)+(Leu+Pro)/(Gln) | 1780.102 |
| 41 | (Glu+Pro)/(Gln)+(Leu+Ile)/(Tau+Ser+Gly) | 1780.421 |
| 42 | (Glu+Tyr)/(Asn+Tau+Gly)+(Leu+Pro)/(Gln) | 1780.719 |
| 43 | (Glu+Pro)/(Asn+Gln)+(Ile+Tyr)/(Tau+Gly) | 1781.37 |
| 44 | (Pro)/(Gln)+(Glu+Ile+Tyr)/(Tau+Ser+Gly) | 1781.462 |
| 45 | (Leu)/(Ser+Gly)+(Glu+Pro+Tyr)/(Asn+Gln) | 1781.511 |
| 46 | (Leu)/(Asn+Ser+Gly)+(Glu+Pro+Tyr)/(Gln) | 1781.567 |
| 47 | (Ile)/(Asn+Tau)+(Pro)/(Gly)+(Leu+Ala)/(Gln) | 1781.716 |
| 48 | (Ile)/(Gly)+(Glu+Pro+Tyr)/(Arg+Tau+Gln) | 1781.73 |
| 49 | (Ile)/(Tau+Gly)+(Glu+Pro+Orn)/(Ser+Gln) | 1781.767 |
| 50 | (Glu+Leu)/(Tau+Gly)+(Pro+Tyr)/(Gln) | 1781.791 |

FIG.40

| No | FORMULA | SSR-test |
|---|---|---|
| 51 | (Leu)/(Asn+Tau+Gly)+(Glu+Pro+Cit)/(Gln) | 1782.853 |
| 52 | (Ile)/(Asn+Tau)+(Pro)/(Gly)+(Ala+Tyr)/(Gln) | 1783.647 |
| 53 | (Glu+Pro)/(Gln)+(Leu+Cit)/(Tau+Ser+Gly) | 1783.69 |
| 54 | (Ile)/(Asn+Tau)+(Ala)/(Gln)+(Pro+Cit)/(Gly) | 1783.87 |
| 55 | (Ile)/(Tau+Gly)+(Glu+Leu+Pro)/(Ser+Gln) | 1783.982 |
| 56 | (Leu)/(Ser+Gly)+(Glu+Pro+Tyr)/(Gln) | 1784.088 |
| 57 | (Leu)/(Tau+Gly)+(Glu+Pro+Tyr)/(Arg+Gln) | 1784.287 |
| 58 | (Glu+Ile)/(Tau+Gly)+(Leu+Pro)/(Ser+Gln) | 1784.703 |
| 59 | (Glu+Pro)/(Gln)+(Leu+Tyr)/(Asn+Ser+Gly) | 1785.211 |
| 60 | (Glu+Tyr)/(Ser+Gly)+(Leu+Pro)/(Tau+Gln) | 1785.406 |
| 61 | (Ile)/(Asn+Gly)+(Glu+Pro+Tyr)/(Arg+Gln) | 1785.433 |
| 62 | (Glu+Leu)/(Asn+Ser+Gly)+(Pro+Tyr)/(Gln) | 1785.47 |
| 63 | (Glu+Leu)/(Tau+Ser+Gly)+(Ile+Pro)/(Gln) | 1785.57 |
| 64 | (Glu+Leu)/(Tau+Gly)+(Pro+Ala)/(Ser+Gln) | 1785.574 |
| 65 | (Glu+Pro)/(Gln)+(Ile+Tyr)/(Asn+Ser+Gly) | 1785.627 |
| 66 | (Glu+Leu+Pro+Tyr)/(Asn+Ser+Gln+Gly) | 1785.635 |
| 67 | (Glu+Leu)/(Asn+Tau+Gly)+(Pro+Orn)/(Gln) | 1785.702 |
| 68 | (Ile)/(Asn+Tau)+(Pro)/(Gly)+(Ala+Orn)/(Gln) | 1785.927 |
| 69 | (Glu+Ile)/(Tau+Gly)+(Pro+Tyr)/(Arg+Gln) | 1786.067 |
| 70 | (Ile)/(Asn+Tau)+(Ala)/(Gln)+(Glu+Orn)/(Gly) | 1786.087 |
| 71 | (Ile)/(Asn+Tau)+(Ala)/(Gln)+(Leu+Pro)/(Gly) | 1786.571 |
| 72 | (Glu+Leu)/(Tau+Gly)+(Pro+Tyr)/(Asn+Gln) | 1786.722 |
| 73 | (Ile)/(Tau+Gly)+(Glu+Pro)/(Ser+Gln) | 1786.993 |
| 74 | (Glu+Leu)/(Asn+Tau+Gly)+(Ile+Pro)/(Gln) | 1787.103 |
| 75 | (Ile)/(Ser+Gly)+(Glu+Pro+Tyr)/(Tau+Gln) | 1787.208 |
| 76 | (Ile)/(Gly)+(Glu+Pro+Tyr)/(Arg+Asn+Gln) | 1787.26 |
| 77 | (Glu+Tyr)/(Tau+Gly)+(Leu+Pro)/(Gln) | 1787.367 |
| 78 | (Glu+Tyr)/(Tau+Gly)+(Leu+Pro)/(Asn+Gln) | 1787.389 |
| 79 | (Leu)/(Tau+Gly)+(Glu+Pro+Cit)/(Gln) | 1787.448 |
| 80 | (Glu+Leu+Pro+Tyr)/(Asn+Tau+Gln+Gly) | 1787.791 |
| 81 | (Ile)/(Gly)+(Glu+Pro+Tyr)/(Gln) | 1788.154 |
| 82 | (Tyr)/(Tau+Gly)+(Glu+Leu+Pro)/(Ser+Gln) | 1788.167 |
| 83 | (Tyr)/(Ser+Gly)+(Glu+Leu+Pro)/(Tau+Gln) | 1788.765 |
| 84 | (Glu+Ile)/(Tau+Gly)+(Leu+Pro)/(Asn+Gln) | 1789.526 |
| 85 | (Ile)/(Gly)+(Glu+Pro+Tyr)/(Arg+Gln) | 1789.593 |
| 86 | (Glu+Leu)/(Asn+Tau+Gly)+(Pro+Cit)/(Gln) | 1789.72 |
| 87 | (Glu+Pro)/(Gln)+(Leu+Cit)/(Tau+Gly) | 1790.012 |
| 88 | (Leu+Cit)/(Asn+Tau+Gly)+(Pro+Tyr)/(Gln) | 1790.047 |
| 89 | (Leu)/(Tau+Gly)+(Glu+Pro+Cit)/(Asn+Gln) | 1790.236 |
| 90 | (Leu+Pro)/(Gln)+(Ile+Tyr)/(Asn+Tau+Gly) | 1790.268 |
| 91 | (Leu)/(Asn+Tau+Gly)+(Glu+Pro)/(Gln) | 1790.272 |
| 92 | (Leu)/(Asn+Tau+Gly)+(Glu+Pro+Orn)/(Gln) | 1790.355 |
| 93 | (Ile)/(Asn+Tau)+(Ala)/(Gln)+(Glu+Tyr)/(Gly) | 1790.526 |
| 94 | (Leu)/(Tau+Gly)+(Glu+Pro+Orn)/(Ser+Gln) | 1790.889 |
| 95 | (Leu)/(Asn+Tau)+(Ala)/(Gln)+(Glu+Pro)/(Gly) | 1790.958 |
| 96 | (Leu)/(Tau+Gly)+(Glu+Pro+Orn)/(Gln) | 1791.252 |
| 97 | (Glu+Pro)/(Tau+Gln)+(Ile+Tyr)/(Ser+Gly) | 1791.299 |
| 98 | (Pro)/(Gln)+(Glu+Leu+Tyr)/(Asn+Tau+Gly) | 1791.303 |
| 99 | (Leu)/(Tau+Gly)+(Glu+Pro+Orn)/(Asn+Gln) | 1791.305 |
| 100 | (Glu+Pro)/(Gln)+(Leu+Ile)/(Asn+Tau+Gly) | 1791.382 |

FIG.41

| No | FORMULA | ROC_AUC |
|---|---|---|
| 1 | 1.195(Glu)/(Gly)-0.4278(Ser)/(Pro)-0.006055(Gln)/(Asn)-1.325(Trp)/(Leu)+2.523 | 0.867033 |
| 2 | 0.2384(Glu)/(Asn)-0.1904(Gly)/(Pro)+0.006456(Gln)/(Ser)+0.2799(Leu)/(Trp)+1.122 | 0.870909 |
| 3 | 2.443(Glu)/(Gln)+0.5025(Pro)/(Gly)+0.2425(Orn)/(Ser)+0.1113(Leu)/(Asn)+0.6254 | 0.862403 |
| 4 | 3.02(Glu)/(Gln)-0.05033(Ser)/(Asn)+0.7249(Leu)/(Gly)-0.6614(Trp)/(Pro)+1.425 | 0.860896 |
| 5 | 2.631(Glu)/(Gln)-0.4981(Ser)/(Leu)+0.4017(Pro)/(Gly)-0.1856(Asn)/(Orn)+1.749 | 0.854651 |
| 6 | 2.444(Glu)/(Gln)+0.08673(Pro)/(Asn)+0.2366(Orn)/(Ser)+0.6049(Leu)/(Gly)+0.6479 | 0.865633 |
| 7 | 0.1729(Glu)/(Asn)-0.5065(Ser)/(Leu)-0.1342(Gly)/(Pro)-0.02004(Gln)/(Orn)+2.338 | 0.855513 |
| 8 | 0.4438(Glu)/(Trp)+0.07691(Pro)/(Asn)+0.04293(Gln)/(Gly)+0.3733(Leu)/(Ser)+0.5154 | 0.856805 |
| 9 | 0.3602(Glu)/(Ser)-0.2151(Asn)/(Orn)-0.1753(Gly)/(Pro)+1.929(Leu)/(Gln)+1.51 | 0.86068 |
| 10 | 3.207(Glu)/(Gln)-0.6632(Ser)/(Leu)+0.1447(Pro)/(Trp)-0.02084(Gly)/(Asn)+1.777 | 0.86531 |
| 11 | 3.205(Glu)/(Gln)-0.6714(Ser)/(Leu)+0.1458(Pro)/(Trp)+0.5776(Asn)/(Gly)+1.557 | 0.864233 |
| 12 | 0.4186(Glu)/(Trp)-0.6507(Ser)/(Leu)+1.105(Pro)/(Gln)-0.01975(Gly)/(Asn)+1.779 | 0.864126 |
| 13 | 0.4184(Glu)/(Trp)-0.6584(Ser)/(Leu)+1.117(Pro)/(Gln)+0.5261(Asn)/(Gly)+1.573 | 0.863695 |
| 14 | 3.643(Glu)/(Gln)-0.06752(Ser)/(Asn)-0.1581(Gly)/(Pro)-1.344(Trp)/(Leu)+2.515 | 0.873923 |
| 15 | 0.4346(Glu)/(Trp)-0.6376(Ser)/(Leu)-0.01987(Gly)/(Asn)-0.0556(Gln)/(Pro)+2.276 | 0.862188 |
| 16 | 0.4339(Glu)/(Trp)-0.6444(Ser)/(Leu)+0.5385(Asn)/(Gly)-0.05651(Gln)/(Pro)+2.074 | 0.862834 |
| 17 | 0.405(Glu)/(Trp)+1.185(Pro)/(Gln)+0.7936(Asn)/(Gly)+0.3952(Leu)/(Ser)+0.4437 | 0.862295 |
| 18 | 3.593(Glu)/(Gln)+0.325(Asn)/(Ser)-0.1651(Gly)/(Pro)-1.327(Trp)/(Leu)+2.215 | 0.87317 |
| 19 | 3.664(Glu)/(Gln)-0.4178(Ser)/(Pro)+0.7522(Asn)/(Gly)-1.362(Trp)/(Leu)+2.269 | 0.871124 |
| 20 | 3.708(Glu)/(Gln)+0.218(Pro)/(Ser)-0.03352(Gly)/(Asn)-1.342(Trp)/(Leu)+1.948 | 0.870693 |
| 21 | 2.968(Glu)/(Gln)-0.536(Ser)/(Leu)+0.6534(Asn)/(Gly)-0.8194(Tau)/(Pro)+2.072 | 0.855082 |
| 22 | 2.525(Glu)/(Gln)-0.3943(Ser)/(Ala)+0.4938(Pro)/(Gly)-1.134(Asn)/(Leu)+1.625 | 0.854651 |
| 23 | 2.709(Glu)/(Gln)-0.4964(Ser)/(Leu)+0.07135(Pro)/(Asn)+0.6497(Orn)/(Gly)+1.441 | 0.857343 |
| 24 | 3.735(Glu)/(Gln)+0.2216(Pro)/(Ser)+0.8901(Asn)/(Gly)-1.347(Trp)/(Leu)+1.588 | 0.870047 |
| 25 | 0.3791(Glu)/(Trp)+0.2158(Pro)/(Ser)+0.8457(Asn)/(Gly)+2.403(Leu)/(Gln)+0.394 | 0.865418 |
| 26 | 0.4254(Glu)/(Trp)-0.6299(Ser)/(Leu)+0.3277(Pro)/(Gly)-0.0108(Gln)/(Asn)+1.86 | 0.861326 |
| 27 | 3.658(Glu)/(Gln)-0.4072(Ser)/(Pro)-0.02783(Gly)/(Asn)-1.359(Trp)/(Leu)+2.557 | 0.871985 |
| 28 | 3.601(Glu)/(Gln)-0.07383(Ser)/(Asn)+0.4359(Pro)/(Gly)-1.291(Trp)/(Leu)+1.945 | 0.871447 |
| 29 | 2.913(Glu)/(Gln)-0.5194(Ser)/(Leu)+0.07689(Pro)/(Asn)+0.471(Arg)/(Gly)+1.417 | 0.855836 |
| 30 | 0.3788(Glu)/(Trp)+0.2939(Asn)/(Ser)-0.1542(Gly)/(Pro)+2.262(Leu)/(Gln)+1.03 | 0.867356 |
| 31 | 0.3836(Glu)/(Trp)-0.05649(Ser)/(Asn)-0.1492(Gly)/(Pro)+2.274(Leu)/(Gln)+1.28 | 0.867571 |
| 32 | 2.646(Glu)/(Gln)+0.08869(Pro)/(Asn)-0.2082(Gly)/(Leu)+0.1691(Arg)/(Ser)+1.375 | 0.857666 |
| 33 | 0.446(Glu)/(Trp)-0.6394(Ser)/(Leu)-0.1009(Gly)/(Pro)-0.0103(Gln)/(Asn)+2.24 | 0.861757 |
| 34 | 2.381(Glu)/(Gln)+0.5311(Pro)/(Gly)+0.07463(Ile)/(Ser)+0.1617(Leu)/(Asn)+0.7065 | 0.855728 |
| 35 | 0.4476(Glu)/(Trp)-0.6407(Ser)/(Leu)+1.67(Asn)/(Gln)-0.1016(Gly)/(Pro)+1.974 | 0.861542 |
| 36 | 0.4606(Glu)/(Trp)-0.6552(Ser)/(Leu)+0.06436(Pro)/(Asn)+0.01351(Gln)/(Gly)+1.667 | 0.856266 |
| 37 | 0.458(Glu)/(Trp)-0.6485(Ser)/(Leu)+0.06471(Pro)/(Asn)-0.1226(Gly)/(Gln)+1.745 | 0.857235 |
| 38 | 1.015(Glu)/(Gly)-0.5776(Ser)/(Leu)+0.1461(Pro)/(Trp)+1.529(Asn)/(Gln)+1.598 | 0.861649 |
| 39 | 0.2522(Glu)/(Asn)-0.4171(Ser)/(Pro)-0.3776(Gly)/(Gln)-1.352(Trp)/(Leu)+2.573 | 0.863157 |
| 40 | 0.2504(Glu)/(Tau)-0.5763(Ser)/(Leu)+1.101(Pro)/(Gln)+0.6224(Asn)/(Gly)+1.534 | 0.857128 |
| 41 | 0.2589(Glu)/(Tau)-0.06523(Ser)/(His)-1.168(Asn)/(Leu)-0.1617(Gly)/(Pro)+2.177 | 0.855728 |
| 42 | 1.006(Glu)/(Gly)-0.677(Ser)/(Leu)+0.146(Pro)/(Trp)-0.00954(Gln)/(Asn)+1.845 | 0.861434 |
| 43 | 2.981(Glu)/(Gln)-0.5303(Ser)/(Leu)-0.02206(Gly)/(Asn)-0.8114(Tau)/(Pro)+2.31 | 0.854759 |
| 44 | 0.2509(Glu)/(Tau)-0.5698(Ser)/(Leu)+1.09(Pro)/(Gln)-0.0216(Gly)/(Asn)+1.769 | 0.857235 |
| 45 | 0.1743(Glu)/(Asn)-0.5008(Ser)/(Leu)-0.1377(Gly)/(Pro)+1.665(Orn)/(Gln)+1.958 | 0.855297 |
| 46 | 0.3253(Glu)/(Ser)+0.09309(Pro)/(Asn)+1.479(Orn)/(Gln)+0.6642(Leu)/(Gly)+0.622 | 0.857989 |
| 47 | 0.2425(Glu)/(Asn)-0.4635(Ser)/(Gln)-0.1859(Gly)/(Pro)-1.296(Trp)/(Leu)+2.47 | 0.874785 |
| 48 | 0.3798(Glu)/(Trp)+0.2131(Pro)/(Ser)-0.03075(Gly)/(Asn)+2.371(Leu)/(Gln)+0.7367 | 0.86531 |
| 49 | 0.4279(Glu)/(Phe)-0.6105(Ser)/(Leu)-0.1081(Gly)/(Pro)-0.01115(Gln)/(Asn)+2.26 | 0.854759 |
| 50 | 0.2626(Glu)/(Tau)-0.5579(Ser)/(Leu)+0.6331(Asn)/(Gly)-0.05542(Gln)/(Pro)+2.022 | 0.854328 |

FIG.42

| No | FORMULA | ROC_AUC |
|---|---|---|
| 51 | 2.807(Glu)/(Gln)-0.514(Ser)/(Leu)-0.6464(Asn)/(Pro)+0.6458(Orn)/(Gly)+1.901 | 0.854759 |
| 52 | 3.236(Glu)/(Gln)-0.6503(Ser)/(Leu)-0.02272(Gly)/(Asn)-0.6921(Trp)/(Pro)+2.434 | 0.860035 |
| 53 | 0.2114(Glu)/(Asn)+0.2158(Pro)/(Ser)-0.5648(Gly)/(Gln)+0.336(Leu)/(Phe)+0.7116 | 0.860358 |
| 54 | 0.6039(Glu)/(Ser)+0.6044(Asn)/(Gln)-0.173(Gly)/(Pro)-1.33(Trp)/(Leu)+2.342 | 0.870478 |
| 55 | 0.219(Glu)/(Asn)-0.6742(Ser)/(Leu)+0.1512(Pro)/(Trp)-0.1926(Gly)/(Gln)+1.75 | 0.85702 |
| 56 | 0.2199(Glu)/(Asn)-0.6831(Ser)/(Leu)+0.1514(Pro)/(Trp)+0.02229(Gln)/(Gly)+1.621 | 0.85562 |
| 57 | 0.258(Glu)/(Asn)+0.2154(Pro)/(Ser)-0.4351(Gly)/(Gln)-1.34(Trp)/(Leu)+1.952 | 0.865095 |
| 58 | 0.2204(Glu)/(Asn)+0.2185(Pro)/(Ser)+0.08194(Gln)/(Gly)-1.188(Phe)/(Leu)+1.545 | 0.861111 |
| 59 | 0.6037(Glu)/(Ser)-0.1723(Gly)/(Pro)-0.004589(Gln)/(Asn)-1.327(Trp)/(Leu)+2.449 | 0.870478 |
| 60 | 1.231(Glu)/(Gly)+0.222(Pro)/(Ser)+1.261(Asn)/(Gln)-1.323(Trp)/(Leu)+1.687 | 0.867033 |
| 61 | 0.2546(Glu)/(Asn)-0.4245(Ser)/(Pro)+0.05101(Gln)/(Gly)-1.352(Trp)/(Leu)+2.292 | 0.861111 |
| 62 | 0.2615(Glu)/(Asn)+0.2185(Pro)/(Ser)+0.0576(Gln)/(Gly)-1.341(Trp)/(Leu)+1.619 | 0.862403 |
| 63 | 0.3683(Glu)/(Trp)-0.05906(Ser)/(Asn)+0.4427(Pro)/(Gly)+2.226(Leu)/(Gln)+0.757 | 0.867356 |
| 64 | 3.628(Glu)/(Gln)+0.2209(Pro)/(Ser)-0.03317(Gly)/(Asn)+0.2871(Leu)/(Trp)+0.6742 | 0.865202 |
| 65 | 3.239(Glu)/(Gln)-0.66(Ser)/(Leu)+0.6075(Asn)/(Gly)-0.6951(Trp)/(Pro)+2.202 | 0.85885 |
| 66 | 0.8831(Glu)/(Gly)-0.528(Ser)/(Leu)+0.07445(Pro)/(Asn)-0.02047(Gln)/(Orn)+1.873 | 0.855836 |
| 67 | 1.278(Glu)/(Gly)-0.437(Ser)/(Gln)+0.09296(Pro)/(Asn)-1.265(Trp)/(Leu)+1.8 | 0.870263 |
| 68 | 0.4268(Glu)/(Trp)-0.6319(Ser)/(Leu)+0.3298(Pro)/(Gly)+1.803(Asn)/(Gln)+1.575 | 0.861111 |
| 69 | 2.499(Glu)/(Gln)-0.08784(Ser)/(Thr)-0.1726(Gly)/(Pro)+0.1309(Leu)/(Asn)+1.432 | 0.861111 |
| 70 | 0.3985(Glu)/(Phe)-0.623(Ser)/(Leu)+1.106(Pro)/(Gln)-0.02512(Gly)/(Asn)+1.806 | 0.858097 |
| 71 | 1.223(Glu)/(Gly)+0.223(Pro)/(Ser)-0.007913(Gln)/(Asn)-1.317(Trp)/(Leu)+1.888 | 0.86671 |
| 72 | 3.652(Glu)/(Gln)+0.2244(Pro)/(Ser)+0.8822(Asn)/(Gly)+0.2889(Leu)/(Trp)+0.3112 | 0.865095 |
| 73 | 0.2153(Glu)/(Asn)+0.2174(Pro)/(Ser)+0.08355(Gln)/(Gly)+0.3346(Leu)/(Phe)+0.2625 | 0.859927 |
| 74 | 3.585(Glu)/(Gln)-0.4079(Ser)/(Pro)-0.0276(Gly)/(Asn)+0.29(Leu)/(Trp)+1.273 | 0.864879 |
| 75 | 0.2169(Glu)/(Asn)+0.2171(Pro)/(Ser)-0.5517(Gly)/(Gln)-1.19(Phe)/(Leu)+1.988 | 0.86208 |
| 76 | 2.874(Glu)/(Gln)-0.512(Ser)/(Leu)+0.07612(Pro)/(Asn)-0.08628(Gly)/(Arg)+1.834 | 0.85562 |
| 77 | 0.4747(Glu)/(Trp)-0.6752(Ser)/(Leu)-0.5836(Asn)/(Pro)+0.01055(Gln)/(Gly)+2.09 | 0.854544 |
| 78 | 0.2419(Glu)/(Tau)+0.1992(Pro)/(Ser)+0.8828(Asn)/(Gly)+2.119(Leu)/(Gln)+0.5048 | 0.85842 |
| 79 | 1.206(Glu)/(Gly)-0.6301(Ser)/(Gln)+0.06438(Pro)/(Asn)-1.131(Phe)/(Leu)+1.838 | 0.866387 |
| 80 | 3.52(Glu)/(Gln)-0.05649(Ser)/(Asn)-0.1652(Gly)/(Pro)+0.2856(Leu)/(Trp)+1.234 | 0.868109 |
| 81 | 0.4151(Glu)/(Phe)-0.6101(Ser)/(Leu)-0.02553(Gly)/(Asn)-0.05463(Gln)/(Pro)+2.302 | 0.855405 |
| 82 | 0.2694(Glu)/(Tau)-0.5257(Ser)/(Leu)+0.06487(Pro)/(Asn)+0.3974(His)/(Gly)+1.502 | 0.855297 |
| 83 | 0.8936(Glu)/(Gly)-0.5259(Ser)/(Leu)+0.07547(Pro)/(Asn)+1.627(Orn)/(Gln)+1.487 | 0.855405 |
| 84 | 0.2694(Glu)/(Tau)-0.5239(Ser)/(Leu)+0.06506(Pro)/(Asn)-0.04279(Gly)/(His)+1.771 | 0.855082 |
| 85 | 0.3971(Glu)/(Phe)-0.6289(Ser)/(Leu)+1.117(Pro)/(Gln)+0.757(Asn)/(Gly)+1.525 | 0.857343 |
| 86 | 0.5549(Glu)/(Ser)+0.08117(Pro)/(Asn)-0.5969(Gly)/(Gln)-1.174(Phe)/(Leu)+2.011 | 0.866064 |
| 87 | 3.476(Glu)/(Gln)+0.2568(Asn)/(Ser)-0.1716(Gly)/(Pro)+0.2822(Leu)/(Trp)+1.005 | 0.867248 |
| 88 | 3.273(Glu)/(Gln)+0.1379(Pro)/(Trp)+0.862(Asn)/(Gly)+0.3948(Leu)/(Ser)+0.4348 | 0.864233 |
| 89 | 2.628(Glu)/(Gln)-0.1118(Ser)/(Arg)+0.09032(Pro)/(Asn)-0.2098(Gly)/(Leu)+1.656 | 0.858635 |
| 90 | 1.202(Glu)/(Gly)-0.4263(Ser)/(Pro)+0.828(Asn)/(Gln)-1.329(Trp)/(Leu)+2.376 | 0.86714 |
| 91 | 0.3728(Glu)/(Trp)-0.04161(Ser)/(Asn)-0.06735(Gln)/(Pro)+0.7013(Leu)/(Gly)+1.374 | 0.865202 |
| 92 | 0.239(Glu)/(Asn)-0.4593(Ser)/(Gln)-0.1876(Gly)/(Pro)+0.2824(Leu)/(Trp)+1.235 | 0.86994 |
| 93 | 0.273(Glu)/(Tau)-0.5468(Ser)/(Leu)-0.1043(Gly)/(Pro)-0.01041(Gln)/(Asn)+2.211 | 0.854328 |
| 94 | 2.753(Glu)/(Gln)-0.5125(Ser)/(Leu)+0.07052(Pro)/(Asn)-0.04228(Gly)/(Orn)+1.807 | 0.856266 |
| 95 | 2.797(Glu)/(Gln)-0.4975(Ser)/(Leu)-0.1943(Asn)/(Orn)-0.1289(Gly)/(Pro)+2.231 | 0.857774 |
| 96 | 0.1548(Glu)/(Asn)-0.532(Ser)/(Leu)+1.266(Pro)/(Gln)+0.6515(Orn)/(Gly)+1.445 | 0.856159 |
| 97 | 3.262(Glu)/(Gln)+0.1365(Pro)/(Trp)-0.03163(Gly)/(Asn)+0.3894(Leu)/(Ser)+0.7857 | 0.862941 |
| 98 | 3.543(Glu)/(Gln)+0.4577(Pro)/(Gly)+0.3343(Asn)/(Ser)-1.268(Trp)/(Leu)+1.597 | 0.869509 |
| 99 | 3.59(Glu)/(Gln)-0.4183(Ser)/(Pro)+0.749(Asn)/(Gly)+0.2911(Leu)/(Trp)+0.9827 | 0.862941 |
| 100 | 0.3631(Glu)/(Trp)+0.458(Pro)/(Gly)+0.2791(Asn)/(Ser)+2.21(Leu)/(Gln)+0.4882 | 0.867033 |

FIG.43

| No | FORMULA | ROC_AUC |
|---|---|---|
| 1 | [-2.2101]+[0.0607]Glu+[-0.0264]Ser+[-0.0267]Tau+[0.0221]Orn+[0.0538]Leu+[-0.0471]Phe | 0.876184 |
| 2 | [-2.3580]+[0.0661]Glu+[-0.0268]Ser+[0.0222]Orn+[0.0705]Leu+[-0.0407]Phe+[-0.0587]Trp | 0.881783 |
| 3 | [-1.9087]+[0.0668]Glu+[-0.0256]Ser+[0.0201]Tyr+[0.0707]Leu+[-0.0523]Phe+[-0.0583]Trp | 0.881568 |
| 4 | [-3.5034]+[0.0649]Glu+[-0.0264]Ser+[0.0201]Orn+[-0.0279]Ile+[0.0692]Leu+[-0.0489]Phe | 0.875754 |
| 5 | [-3.5162]+[0.0606]Glu+[-0.0251]Ser+[0.0187]Orn+[0.0555]Leu+[-0.0495]Phe | 0.872201 |
| 6 | [-4.0313]+[0.0622]Glu+[-0.0287]Ser+[0.0110]Arg+[0.0193]Orn+[0.0551]Leu+[-0.0518]Phe | 0.875108 |
| 7 | [-1.8280]+[0.0618]Glu+[-0.0250]Ser+[-0.0216]Tau+[0.0134]Tyr+[0.0550]Leu+[-0.0561]Phe | 0.873708 |
| 8 | [-2.6302]+[0.0578]Glu+[-0.0214]Ser+[-0.0045]Gly+[0.0204]Orn+[0.0536]Leu+[-0.0497]Phe | 0.877692 |
| 9 | [-3.6979]+[0.0601]Glu+[-0.0253]Ser+[0.0126]Tyr+[0.0180]Orn+[0.0538]Leu+[-0.0564]Phe | 0.874462 |
| 10 | [-1.4617]+[0.0697]Glu+[-0.0225]Ser+[-0.0446]ABA+[0.0744]Leu+[-0.0383]Phe+[-0.0569]Trp | 0.877799 |
| 11 | [-2.9967]+[0.0612]Glu+[-0.0240]Ser+[0.0135]Tyr+[0.0560]Leu+[-0.0578]Phe | 0.872308 |
| 12 | [-1.6889]+[0.0671]Glu+[-0.0251]Ser+[0.0727]Leu+[-0.0422]Phe+[-0.0537]Trp | 0.876077 |
| 13 | [-3.3272]+[0.0663]Glu+[-0.0211]Ser+[-0.0511]ABA+[0.0213]Orn+[0.0641]Leu+[-0.0675]Trp | 0.879414 |
| 14 | [-2.2203]+[0.0694]Glu+[-0.0295]Ser+[0.0133]Arg+[0.0726]Leu+[-0.0436]Phe+[-0.0568]Trp | 0.878445 |
| 15 | [-2.8521]+[0.0648]Glu+[-0.0082]Gly+[-0.0833]ABA+[0.0229]Orn+[0.0623]Leu+[-0.0690]Trp | 0.882321 |
| 16 | [-2.0432]+[0.0636]Glu+[-0.0282]Ser+[-0.0219]Tau+[0.0103]Arg+[0.0568]Leu+[-0.0509]Phe | 0.872093 |
| 17 | [-3.7569]+[0.0668]Glu+[-0.0257]Ser+[0.0246]Orn+[-0.0296]Ile+[0.0752]Leu+[-0.0632]Trp | 0.879522 |
| 18 | [-4.3969]+[0.0650]Glu+[-0.0281]Ser+[0.0135]Arg+[0.0239]Orn+[0.0603]Leu+[-0.0685]Trp | 0.881245 |
| 19 | [-2.2848]+[0.0601]Glu+[-0.0253]Ser+[0.0094]Pro+[0.0686]Leu+[-0.0427]Phe+[-0.0523]Trp | 0.882429 |
| 20 | [-2.9305]+[0.0650]Glu+[-0.0251]Ser+[0.0135]Tyr+[-0.0243]Ile+[0.0681]Leu+[-0.0577]Phe | 0.872201 |
| 21 | [-3.1959]+[0.0674]Glu+[-0.0284]Ser+[0.0111]Arg+[-0.0262]Ile+[0.0706]Leu+[-0.0524]Phe | 0.87317 |
| 22 | [-2.9811]+[0.0605]Glu+[-0.0205]Ser+[-0.0044]Gly+[0.0251]Orn+[0.0595]Leu+[-0.0651]Trp | 0.879953 |
| 23 | [-3.2974]+[0.0700]Glu+[-0.0233]Ser+[0.0143]Arg+[-0.0610]ABA+[0.0661]Leu+[-0.0668]Trp | 0.877476 |
| 24 | [-3.5520]+[0.0605]Glu+[-0.0252]Ser+[0.0007]Thr+[0.0186]Orn+[0.0555]Leu+[-0.0496]Phe | 0.872524 |
| 25 | [-2.7320]+[0.0657]Glu+[-0.0247]Ser+[-0.0243]Ile+[0.0702]Leu+[-0.0502]Phe | 0.870263 |
| 26 | [-0.6193]+[0.0673]Glu+[-0.0261]Ser+[-0.0204]Tau+[0.0716]Leu+[-0.0401]Phe+[-0.0531]Trp | 0.877692 |
| 27 | [-2.7886]+[0.0618]Glu+[-0.0237]Ser+[0.0581]Leu+[-0.0505]Phe | 0.868217 |
| 28 | [-3.6470]+[0.0547]Glu+[-0.0241]Ser+[0.0099]Pro+[0.0137]Tyr+[0.0518]Leu+[-0.0579]Phe | 0.876184 |
| 29 | [-3.4455]+[0.0624]Glu+[-0.0272]Ser+[0.0101]Arg+[0.0133]Tyr+[0.0556]Leu+[-0.0596]Phe | 0.871447 |
| 30 | [-1.6114]+[0.0624]Glu+[-0.0247]Ser+[-0.0218]Tau+[0.0571]Leu+[-0.0487]Phe | 0.869832 |
| 31 | [-3.2345]+[0.0631]Glu+[-0.0270]Ser+[0.0102]Arg+[0.0578]Leu+[-0.0527]Phe | 0.869617 |
| 32 | [-4.0849]+[0.0621]Glu+[-0.0237]Ser+[0.0098]Tyr+[0.0227]Orn+[0.0591]Leu+[-0.0678]Trp | 0.879737 |
| 33 | [-1.6395]+[0.0705]Glu+[-0.0264]Ser+[-0.0236]Ile+[0.0842]Leu+[-0.0419]Phe+[-0.0525]Trp | 0.8764 |
| 34 | [-3.0899]+[0.0648]Glu+[-0.0259]Ser+[0.0115]Arg+[-0.0343]ABA+[0.0585]Leu+[-0.0506]Phe | 0.872524 |
| 35 | [-3.0663]+[0.0608]Glu+[-0.0243]Ser+[0.0013]Thr+[0.0134]Tyr+[0.0559]Leu+[-0.0578]Phe | 0.87177 |
| 36 | [-3.9066]+[0.0607]Glu+[-0.0245]Ser+[0.0123]Cit+[0.0180]Orn+[0.0566]Leu+[-0.0502]Phe | 0.873708 |
| 37 | [-2.7677]+[0.0674]Glu+[-0.0189]Ser+[-0.0553]ABA+[0.0664]Leu+[-0.0626]Trp | 0.873062 |
| 38 | [-3.3324]+[0.0617]Glu+[-0.0238]Ser+[-0.0252]ABA+[0.0177]Orn+[0.0562]Leu+[-0.0477]Phe | 0.872416 |
| 39 | [-1.6171]+[0.0660]Glu+[-0.0256]Ser+[-0.0207]Tau+[-0.0225]Ile+[0.0684]Leu+[-0.0487]Phe | 0.870586 |
| 40 | [-3.1053]+[0.0669]Glu+[-0.0186]Ser+[-0.0599]ABA+[0.0125]Tyr+[0.0644]Leu+[-0.0672]Trp | 0.8764 |
| 41 | [-1.8833]+[0.0633]Glu+[-0.0214]Ser+[-0.0040]Gly+[-0.0246]Ile+[0.0690]Leu+[-0.0507]Phe | 0.87037 |
| 42 | [-1.5712]+[0.0655]Glu+[-0.0138]Ser+[-0.0054]Gly+[-0.0691]ABA+[0.0655]Leu+[-0.0635]Trp | 0.877907 |
| 43 | [-3.5127]+[0.0631]Glu+[-0.0242]Ser+[-0.0080]Cit+[0.0234]Orn+[0.0608]Leu+[-0.0659]Trp | 0.876938 |
| 44 | [-1.8064]+[0.0680]Glu+[-0.0285]Ser+[0.0505]Met+[0.0717]Leu+[-0.0514]Phe+[-0.0568]Trp | 0.879737 |
| 45 | [-2.0084]+[0.0682]Glu+[-0.0257]Ser+[0.0034]Lys+[0.0705]Leu+[-0.0415]Phe+[-0.0561]Trp | 0.877261 |
| 46 | [-2.7274]+[0.0707]Glu+[-0.0203]Ser+[-0.0547]ABA+[-0.0236]Ile+[0.0783]Leu+[-0.0618]Trp | 0.874354 |
| 47 | [-4.1001]+[0.0613]Glu+[-0.0257]Ser+[0.0096]His+[0.0202]Orn+[0.0546]Leu+[-0.0508]Phe | 0.874677 |
| 48 | [-2.0429]+[0.0669]Glu+[-0.0252]Ser+[0.0021]Ala+[0.0713]Leu+[-0.0450]Phe+[-0.0546]Trp | 0.877369 |
| 49 | [-2.2973]+[0.0628]Glu+[-0.0255]Ser+[-0.0286]Tau+[0.0257]Orn+[0.0598]Leu+[-0.0638]Trp | 0.878876 |
| 50 | [-3.4184]+[0.0550]Glu+[-0.0239]Ser+[0.0099]Pro+[0.0542]Leu+[-0.0505]Phe | 0.872416 |

FIG.44

| No | FORMULA | ROC_AUC |
|---|---|---|
| 51 | [-2.8354]+[0.0624]Glu+[-0.0225]Ser+[-0.0312]ABA+[0.0141]Tyr+[0.0566]Leu+[-0.0559]Phe | 0.871016 |
| 52 | [-2.2662]+[0.0558]Glu+[-0.0250]Ser+[0.0096]Pro+[-0.0206]Tau+[0.0533]Leu+[-0.0490]Phe | 0.874031 |
| 53 | [-3.7936]+[0.0628]Glu+[-0.0238]Ser+[0.0229]Orn+[0.0608]Leu+[-0.0645]Trp | 0.877584 |
| 54 | [-2.8786]+[0.0649]Glu+[-0.0254]Ser+[0.0026]Thr+[-0.0248]Ile+[0.0703]Leu+[-0.0503]Phe | 0.870801 |
| 55 | [-3.7143]+[0.0602]Glu+[-0.0251]Ser+[0.0013]Ala+[0.0182]Orn+[0.0547]Leu+[-0.0513]Phe | 0.87177 |
| 56 | [-2.3047]+[0.0659]Glu+[-0.0072]Gly+[-0.0833]ABA+[0.0645]Leu+[-0.0634]Trp | 0.874785 |
| 57 | [-4.0746]+[0.0541]Glu+[-0.0250]Ser+[0.0095]Pro+[0.0169]Orn+[0.0521]Leu+[-0.0496]Phe | 0.874031 |
| 58 | [-1.4339]+[0.0637]Glu+[-0.0233]Ser+[-0.0219]Tau+[-0.0296]ABA+[0.0576]Leu+[-0.0467]Phe | 0.870909 |
| 59 | [-1.5039]+[0.0678]Glu+[-0.0204]Ser+[-0.0226]Tau+[-0.0530]ABA+[0.0655]Leu+[-0.0615]Trp | 0.875969 |
| 60 | [-1.7345]+[0.0616]Glu+[-0.0252]Ser+[-0.0220]Tau+[0.0023]Thr+[0.0570]Leu+[-0.0488]Phe | 0.86994 |
| 61 | [-2.2841]+[0.0593]Glu+[-0.0212]Ser+[-0.0033]Gly+[0.0116]Tyr+[0.0551]Leu+[-0.0571]Phe | 0.871016 |
| 62 | [-3.6011]+[0.0612]Glu+[-0.0274]Ser+[0.0185]Orn+[0.0348]Met+[0.0548]Leu+[-0.0577]Phe | 0.874892 |
| 63 | [-3.1769]+[0.0635]Glu+[-0.0220]Ser+[0.0630]Leu+[-0.0591]Trp | 0.870155 |
| 64 | [-0.9498]+[0.0650]Glu+[-0.0223]Ser+[-0.0036]Gly+[0.0716]Leu+[-0.0425]Phe+[-0.0536]Trp | 0.877799 |
| 65 | [-2.8176]+[0.0618]Glu+[-0.0237]Ser+[0.0003]Lys+[0.0579]Leu+[-0.0505]Phe | 0.868325 |
| 66 | [-1.8839]+[0.0619]Glu+[-0.0248]Ser+[-0.0232]Tau+[0.0020]Ala+[0.0555]Leu+[-0.0513]Phe | 0.872524 |
| 67 | [-3.9022]+[0.0605]Glu+[-0.0267]Ser+[0.0175]Asn+[0.0185]Orn+[0.0551]Leu+[-0.0512]Phe | 0.872308 |
| 68 | [-3.4727]+[0.0627]Glu+[-0.0219]Ser+[0.0103]Tyr+[0.0610]Leu+[-0.0624]Trp | 0.873277 |
| 69 | [-2.1434]+[0.0672]Glu+[-0.0268]Ser+[0.0199]Asn+[0.0721]Leu+[-0.0440]Phe+[-0.0539]Trp | 0.876507 |
| 70 | [-3.2740]+[0.0598]Glu+[-0.0247]Ser+[0.0212]Orn+[-0.0032]Lys+[0.0578]Leu+[-0.0493]Phe | 0.871662 |
| 71 | [-3.0550]+[0.0614]Glu+[-0.0237]Ser+[0.0016]Ala+[0.0569]Leu+[-0.0526]Phe | 0.870263 |
| 72 | [-1.9165]+[0.0658]Glu+[-0.0265]Ser+[0.0051]Thr+[0.0728]Leu+[-0.0424]Phe+[-0.0552]Trp | 0.875538 |
| 73 | [-3.2781]+[0.0635]Glu+[-0.0289]Ser+[0.0090]Arg+[0.0328]Met+[0.0568]Leu+[-0.0593]Phe | 0.870801 |
| 74 | [-3.2296]+[0.0632]Glu+[-0.0270]Ser+[-0.0001]Thr+[0.0103]Arg+[0.0578]Leu+[-0.0527]Phe | 0.869617 |
| 75 | [-3.3864]+[0.0608]Glu+[-0.0190]Ser+[0.0090]Pro+[-0.0549]ABA+[0.0623]Leu+[-0.0613]Trp | 0.880491 |
| 76 | [-2.6337]+[0.0630]Glu+[-0.0222]Ser+[-0.0295]ABA+[0.0587]Leu+[-0.0483]Phe | 0.868971 |
| 77 | [-2.8903]+[0.0612]Glu+[-0.0241]Ser+[0.0018]Thr+[0.0581]Leu+[-0.0506]Phe | 0.868648 |
| 78 | [-3.3850]+[0.0589]Glu+[-0.0252]Ser+[0.0101]Pro+[-0.0266]Ile+[0.0675]Leu+[-0.0502]Phe | 0.874462 |
| 79 | [-1.7528]+[0.0671]Glu+[-0.0251]Ser+[0.0019]Cit+[0.0728]Leu+[-0.0423]Phe+[-0.0534]Trp | 0.875538 |
| 80 | [-2.6718]+[0.0594]Glu+[-0.0250]Ser+[-0.0018]Gln+[0.0195]Orn+[0.0556]Leu+[-0.0468]Phe | 0.87317 |
| 81 | [-3.8016]+[0.0569]Glu+[-0.0220]Ser+[0.0091]Pro+[0.0587]Leu+[-0.0576]Trp | 0.877261 |
| 82 | [-2.9928]+[0.0542]Glu+[-0.0187]Ser+[0.0097]Pro+[-0.0042]Gly+[0.0571]Leu+[-0.0576]Trp | 0.878768 |
| 83 | [-2.9300]+[0.0610]Glu+[-0.0239]Ser+[0.0137]Tyr+[-0.0007]Lys+[0.0565]Leu+[-0.0580]Phe | 0.872201 |
| 84 | [-1.9563]+[0.0594]Glu+[-0.0204]Ser+[-0.0039]Gly+[0.0567]Leu+[-0.0509]Phe | 0.869617 |
| 85 | [-2.7834]+[0.0583]Glu+[0.0098]Pro+[-0.0080]Gly+[-0.0828]ABA+[0.0600]Leu+[-0.0620]Trp | 0.882967 |
| 86 | [-2.5036]+[0.0648]Glu+[-0.0072]Gly+[-0.0836]ABA+[0.0034]Val+[0.0603]Leu+[-0.0645]Trp | 0.877261 |
| 87 | [-3.2637]+[0.0616]Glu+[-0.0243]Ser+[0.0052]His+[0.0127]Tyr+[0.0557]Leu+[-0.0581]Phe | 0.871447 |
| 88 | [-2.6061]+[0.0666]Glu+[-0.0233]Ser+[-0.0270]ABA+[-0.0231]Ile+[0.0702]Leu+[-0.0482]Phe | 0.871016 |
| 89 | [-2.0415]+[0.0623]Glu+[-0.0266]Ser+[0.0197]Asn+[-0.0219]Tau+[0.0566]Leu+[-0.0507]Phe | 0.870155 |
| 90 | [-3.1740]+[0.0623]Glu+[-0.0240]Ser+[0.0071]His+[0.0576]Leu+[-0.0515]Phe | 0.869724 |
| 91 | [-3.9607]+[0.0620]Glu+[-0.0248]Ser+[0.0039]Thr+[0.0227]Orn+[0.0608]Leu+[-0.0656]Trp | 0.877153 |
| 92 | [-3.0069]+[0.0618]Glu+[-0.0258]Ser+[0.0104]Tyr+[0.0262]Met+[0.0559]Leu+[-0.0625]Phe | 0.872093 |
| 93 | [-2.8872]+[0.0624]Glu+[-0.0262]Ser+[0.0363]Met+[0.0572]Leu+[-0.0586]Phe | 0.869136 |
| 94 | [-3.1903]+[0.0560]Glu+[-0.0227]Ser+[0.0108]Pro+[-0.0051]Thr+[0.0540]Leu+[-0.0502]Phe | 0.872631 |
| 95 | [-3.3328]+[0.0612]Glu+[-0.0255]Ser+[0.0158]Asn+[0.0129]Tyr+[0.0555]Leu+[-0.0590]Phe | 0.870693 |
| 96 | [-2.1452]+[0.0620]Glu+[-0.0241]Ser+[-0.0228]Tau+[0.0168]Cit+[0.0585]Leu+[-0.0492]Phe | 0.870478 |
| 97 | [-3.8434]+[0.0564]Glu+[-0.0276]Ser+[0.0100]Pro+[0.0104]Arg+[0.0538]Leu+[-0.0528]Phe | 0.872739 |
| 98 | [-3.2123]+[0.0618]Glu+[-0.0254]Ser+[0.0189]Asn+[0.0576]Leu+[-0.0523]Phe | 0.868002 |
| 99 | [-1.3552]+[0.0673]Glu+[-0.0075]Gly+[-0.0761]ABA+[0.0703]Leu+[-0.0319]Phe+[-0.0578]Trp | 0.878768 |
| 100 | [-4.0821]+[0.0564]Glu+[-0.0218]Ser+[0.0090]Pro+[0.0095]Tyr+[0.0568]Leu+[-0.0605]Trp | 0.877369 |

FIG.45

| No | FORMULA | ROC_AUC |
|---|---|---|
| 1 | -(4.538e-01)Glu+(7.542e-02)Gly+(6.121e-01)ABA-(2.274e-01)Orn-(4.280e-01)Leu+(4.229e-01)Trp+(3.081e+01) | 0.882752 |
| 2 | -(5.596e-01)Glu+(2.305e-01)Ser-(2.802e-01)Orn-(5.481e-01)Leu+(1.921e-01)Phe+(4.667e-01)Trp+(4.185e+01) | 0.882429 |
| 3 | -(4.219e-01)Glu-(1.417e-01)Pro+(8.297e-02)Gly+(6.391e-01)ABA-(4.477e-01)Leu+(4.314e-01)Trp+(3.552e+01) | 0.882106 |
| 4 | -(5.571e-01)Glu+(1.854e-01)Ser+(5.744e-02)Gly-(3.156e-01)Orn-(5.287e-01)Leu+(5.224e-01)Trp+(4.277e+01) | 0.881998 |
| 5 | (5.272e-01)Glu+(1.825e-01)Pro-(1.057e-01)Gly+(2.917e-01)Orn+(5.203e-01)Leu-(5.673e-01)Trp-(7.210e+01) | 0.881783 |
| 6 | (5.282e-01)Glu-(2.382e-01)Ser+(1.748e-01)Pro+(5.874e-01)Leu-(2.736e-01)Phe-(4.624e-01)Trp-(4.731e+01) | 0.881029 |
| 7 | -(5.694e-01)Glu+(7.946e-02)Gly-(1.462e-01)Tyr-(2.988e-01)Orn-(5.040e-01)Leu+(5.521e-01)Trp+(6.351e+01) | 0.880922 |
| 8 | -(5.214e-01)Glu+(2.436e-01)Ser-(1.546e-01)Pro-(2.612e-01)Orn-(5.197e-01)Leu+(5.536e-01)Trp+(6.398e+01) | 0.880491 |
| 9 | (5.583e-01)Glu-(2.268e-01)Ser-(1.028e-02)Gln+(2.967e-01)Orn-(5.343e-01)Leu-(5.130e-01)Trp-(4.547e+01) | 0.879737 |
| 10 | -(5.401e-01)Glu+(2.159e-01)Ser-(2.560e-01)Tyr-(5.402e-01)Leu+(3.207e-01)Phe+(4.489e-01)Trp+(3.584e+01) | 0.879414 |
| 11 | -(5.618e-01)Glu+(8.506e-02)Gly-(3.095e-01)Orn+(1.257e-01)Ile-(5.655e-01)Leu+(4.957e-01)Trp+(5.442e+01) | 0.879199 |
| 12 | -(5.374e-01)Glu+(2.212e-01)Ser-(2.780e-01)Orn+(1.707e-01)Ile-(5.723e-01)Leu+(4.778e-01)Trp+(4.550e+01) | 0.879199 |
| 13 | -(5.674e-01)Glu+(2.564e-01)Ser-(1.326e-01)Arg-(2.815e-01)Orn-(4.973e-01)Leu+(5.179e-01)Trp+(5.493e+01) | 0.878984 |
| 14 | -(5.926e-01)Glu+(2.511e-01)Ser-(1.317e-01)Arg-(5.733e-01)Leu+(2.039e-01)Phe+(4.451e-01)Trp+(3.924e+01) | 0.878984 |
| 15 | -(5.286e-01)Glu+(2.216e-01)Ser-(3.632e-01)Met-(5.389e-01)Leu+(2.727e-01)Phe+(4.180e-01)Trp+(3.048e+01) | 0.878984 |
| 16 | (5.456e-01)Glu-(2.273e-01)Ser+(1.818e-01)Tyr-(2.692e-01)Orn+(4.912e-01)Leu-(5.512e-01)Trp-(5.497e+01) | 0.878768 |
| 17 | (4.598e-01)Glu-(7.178e-02)Gly-(6.344e-01)ABA+(4.768e-01)Orn+(4.746e-01)Phe-(3.508e-01)Trp-(1.613e+01) | 0.878445 |
| 18 | -(5.493e-01)Glu+(2.563e-01)Ser-(1.673e-01)Pro-(1.340e-01)Arg-(5.385e-01)Leu+(5.399e-01)Trp+(6.366e+01) | 0.878445 |
| 19 | -(5.108e-01)Glu+(1.767e-01)Ser+(4.412e-01)ABA-(2.398e-01)Orn-(4.828e-01)Leu+(4.718e-01)Trp+(3.881e+01) | 0.87823 |
| 20 | -(5.428e-01)Glu+(2.451e-01)Ser-(1.766e-01)Pro-(2.055e-02)Val-(5.538e-01)Leu+(5.541e-01)Trp+(6.086e+01) | 0.878122 |
| 21 | (5.349e-01)Glu-(1.876e-01)Ser+(1.949e-01)Pro-(7.007e-02)Gly+(5.768e-01)Leu-(5.506e-01)Trp-(5.155e+01) | 0.878122 |
| 22 | -(5.317e-01)Glu-(2.038e-01)Pro+(1.041e-01)Gly-(5.943e-01)Leu+(3.156e-01)Phe+(4.604e-01)Trp+(5.234e+01) | 0.878122 |
| 23 | -(4.867e-01)Glu+(1.807e-01)Ser-(1.446e-01)Pro+(4.629e-01)ABA-(5.102e-01)Leu+(4.848e-01)Trp+(4.555e+01) | 0.878015 |
| 24 | -(5.262e-01)Glu+(2.364e-01)Ser-(1.630e-01)Pro-(1.819e-01)Tyr-(5.295e-01)Leu+(5.720e-01)Trp+(6.348e+01) | 0.877907 |
| 25 | (5.633e-01)Glu-(2.292e-01)Ser+(2.898e-01)Orn+(5.285e-01)Leu-(5.166e-01)Trp-(4.993e+01) | 0.877799 |
| 26 | -(5.742e-01)Glu+(8.798e-02)Gly+(8.902e-03)Gln-(3.243e-01)Orn-(5.362e-01)Leu+(5.194e-01)Trp+(5.334e+01) | 0.877799 |
| 27 | (5.436e-01)Glu-(2.434e-01)Ser+(1.725e-01)Pro+(5.646e-02)His+(5.644e-01)Leu-(5.419e-01)Trp-(6.174e+01) | 0.877692 |
| 28 | -(5.764e-01)Glu+(8.965e-02)Gly-(3.227e-01)Orn+(4.760e-03)Lys-(5.332e-01)Leu+(5.209e-01)Trp+(5.659e+01) | 0.877692 |
| 29 | -(5.785e-01)Glu+(8.986e-02)Gly-(3.191e-01)Orn-(5.312e-01)Leu+(5.228e-01)Trp+(5.704e+01) | 0.877584 |
| 30 | -(5.384e-01)Glu+(2.468e-01)Ser-(1.717e-01)Pro-(2.514e-02)Thr-(5.695e-01)Leu+(5.429e-01)Trp+(5.984e+01) | 0.877476 |
| 31 | -(5.758e-01)Glu+(9.087e-02)Gly-(1.981e-02)Thr-(3.158e-01)Orn-(5.318e-01)Leu+(5.266e-01)Trp+(5.837e+01) | 0.877476 |
| 32 | -(5.739e-01)Glu+(8.985e-02)Gly-(3.152e-01)Orn-(1.004e-01)Met-(5.224e-01)Leu+(5.294e-01)Trp+(5.787e+01) | 0.877476 |
| 33 | -(5.431e-01)Glu+(2.394e-01)Ser-(1.761e-01)Pro-(5.704e-01)Leu+(5.398e-01)Trp+(5.920e+01) | 0.877476 |
| 34 | -(5.871e-01)Glu+(9.326e-02)Gly+(1.017e-01)Arg-(3.144e-01)Orn-(5.102e-01)Leu+(5.264e-01)Trp+(6.292e+01) | 0.877476 |
| 35 | -(5.678e-01)Glu+(8.196e-02)Gly+(1.301e-01)Cit-(3.189e-01)Orn-(5.166e-01)Leu+(5.342e-01)Trp+(5.268e+01) | 0.877369 |
| 36 | -(5.784e-01)Glu+(8.979e-02)Gly+(9.250e-04)Val-(3.193e-01)Orn-(5.319e-01)Leu+(5.221e-01)Trp+(5.696e+01) | 0.877369 |
| 37 | -(5.484e-01)Glu+(2.329e-01)Ser-(2.802e-01)Orn-(1.866e-01)Met-(5.070e-01)Leu+(5.240e-01)Trp+(5.032e+01) | 0.877369 |
| 38 | (5.728e-01)Glu-(9.125e-02)Gly+(3.082e-01)Orn+(5.522e-01)Leu-(2.170e-01)Phe-(4.654e-01)Trp-(4.760e+01) | 0.877261 |
| 39 | (5.417e-01)Glu-(2.409e-01)Ser+(1.742e-01)Pro+(4.485e-02)Met-(5.669e-01)Leu+(5.429e-01)Trp-(5.932e+01) | 0.877261 |
| 40 | -(4.521e-01)Glu+(6.076e-02)Gly+(6.399e-01)ABA-(1.365e-01)Tyr-(4.299e-01)Leu+(4.230e-01)Trp+(2.969e+01) | 0.877261 |
| 41 | (5.636e-01)Glu-(2.321e-01)Ser+(1.034e-02)Val+(2.880e-01)Orn-(5.207e-01)Leu-(5.238e-01)Trp-(5.071e+01) | 0.877261 |
| 42 | (5.432e-01)Glu-(2.390e-01)Ser+(1.790e-01)Pro-(4.128e-03)Ala+(5.722e-01)Leu-(5.369e-01)Trp-(5.853e+01) | 0.877153 |
| 43 | -(5.563e-01)Glu+(2.321e-01)Ser-(2.248e-02)Ala-(2.904e-01)Orn-(5.153e-01)Leu+(5.350e-01)Trp+(5.501e+01) | 0.877153 |
| 44 | (5.274e-01)Glu-(2.220e-01)Ser-(2.598e-01)Cit+(2.911e-01)Orn+(4.885e-01)Leu-(5.307e-01)Trp-(3.715e+01) | 0.877153 |
| 45 | -(5.579e-01)Glu+(2.544e-01)Ser-(1.762e-01)Pro-(7.633e-02)Lys-(5.166e-01)Leu+(5.660e-01)Trp+(6.605e+01) | 0.877046 |
| 46 | -(5.671e-01)Glu+(2.313e-01)Ser-(2.821e-01)Orn-(9.997e-03)Lys-(5.240e-01)Leu+(5.203e-01)Trp+(5.070e+01) | 0.877046 |
| 47 | -(4.608e-01)Glu+(7.170e-02)Gly+(6.499e-01)ABA-(2.268e-01)Val-(4.390e-01)Leu+(4.084e-01)Trp+(2.489e+01) | 0.876938 |
| 48 | -(5.771e-01)Glu+(2.267e-01)Ser-(2.763e-02)Ala-(5.910e-01)Leu+(2.459e-01)Phe+(4.527e-01)Trp+(3.836e+01) | 0.87683 |
| 49 | -(5.316e-01)Glu+(2.355e-01)Ser-(1.871e-01)Pro+(2.038e-02)Gln-(5.839e-01)Leu+(5.345e-01)Trp+(5.105e+01) | 0.87683 |
| 50 | -(5.393e-01)Glu+(2.189e-01)Ser+(3.347e-01)Tau-(3.148e-01)Orn-(4.824e-01)Leu+(4.663e-01)Trp+(3.275e+01) | 0.876615 |

FIG.46

| No | FORMULA | ROC_AUC |
|---|---|---|
| 51 | -(5.180e-01)Glu+(1.644e-01)Ser+(4.796e-01)ABA-(5.338e-01)Leu+(1.771e-01)Phe+(3.978e-01)Trp+(2.383e+01) | 0.876615 |
| 52 | -(5.948e-01)Glu+(2.544e-02)Ala-(2.676e-01)Orn-(5.440e-01)Leu+(2.028e-01)Phe+(4.867e-01)Trp+(7.468e+01) | 0.8764 |
| 53 | (4.824e-01)Glu+(1.261e-01)Pro-(5.237e-01)ABA+(1.894e-01)Orn+(4.590e-01)Leu-(4.802e-01)Trp-(6.700e+01) | 0.8764 |
| 54 | -(5.873e-01)Glu+(2.381e-01)Ser-(5.246e-02)Val-(5.652e-01)Leu+(2.328e-01)Phe+(4.712e-01)Trp+(3.690e+01) | 0.876292 |
| 55 | (5.522e-01)Glu+(1.527e-01)Pro+(1.614e-01)Tyr+(2.306e-01)Orn+(4.979e-01)Leu-(5.870e-01)Trp-(9.690e+01) | 0.876292 |
| 56 | -(4.677e-01)Glu+(7.139e-02)Gly+(6.580e-01)ABA-(5.098e-02)Lys-(4.179e-01)Leu+(4.074e-01)Trp+(2.762e+01) | 0.876292 |
| 57 | -(6.022e-01)Glu+(2.363e-01)Ser-(6.105e-02)Lys-(5.646e-01)Leu+(2.108e-01)Phe+(4.632e-01)Trp+(3.932e+01) | 0.876184 |
| 58 | (4.555e-01)Glu-(7.015e-02)Gly-(6.411e-01)ABA+(1.246e-01)Met+(4.465e-01)Leu-(4.021e-01)Trp-(2.423e+01) | 0.876184 |
| 59 | (5.655e-01)Glu-(2.169e-01)Ser-(1.331e-01)Ile+(6.358e-01)Leu-(2.058e-01)Phe-(4.109e-01)Trp-(3.057e+01) | 0.876184 |
| 60 | -(5.188e-01)Glu+(2.303e-01)Ser-(1.645e-01)Pro+(1.677e-01)Ile-(6.114e-01)Leu+(4.988e-01)Trp+(5.397e+01) | 0.876077 |
| 61 | -(5.689e-01)Glu-(2.284e-01)Tyr-(2.335e-01)Orn-(5.111e-01)Leu+(2.743e-01)Phe+(4.829e-01)Trp+(7.048e+01) | 0.876077 |
| 62 | (4.807e-01)Glu+(9.750e-02)Ser-(5.683e-02)Gly-(5.888e-01)ABA+(4.855e-01)Leu-(4.169e-01)Trp-(1.917e+01) | 0.876077 |
| 63 | (5.723e-01)Glu+(1.806e-01)Asn-(8.871e-02)Gly+(3.072e-01)Orn+(5.181e-01)Leu-(5.188e-01)Trp-(6.244e+01) | 0.876077 |
| 64 | -(5.700e-01)Glu+(9.265e-02)Gly-(2.662e-02)Ala-(3.209e-01)Orn-(5.157e-01)Leu+(5.448e-01)Trp+(6.285e+01) | 0.876077 |
| 65 | (5.556e-01)Glu-(2.377e-01)Ser+(1.331e-01)His+(3.011e-01)Orn+(5.060e-01)Leu-(5.200e-01)Trp-(5.663e+01) | 0.875969 |
| 66 | -(5.330e-01)Glu-(1.610e-01)Pro-(2.323e-01)Tyr-(5.363e-01)Leu+(3.464e-01)Phe+(4.781e-01)Trp+(7.671e+01) | 0.875969 |
| 67 | -(4.781e-01)Glu+(5.557e-01)ABA-(2.096e-01)Tyr-(4.558e-01)Leu+(2.384e-01)Phe+(3.925e-01)Trp+(4.090e+01) | 0.875861 |
| 68 | -(5.379e-01)Glu+(2.335e-01)Ser-(1.684e-01)Pro+(2.726e-01)Tau-(5.476e-01)Leu+(5.037e-01)Trp+(4.465e+01) | 0.875861 |
| 69 | (4.918e-01)Glu-(1.637e-02)Gln-(5.561e-01)ABA+(2.168e-01)Orn+(4.630e-01)Leu-(4.328e-01)Trp-(4.415e+01) | 0.875861 |
| 70 | (4.631e-01)Glu-(7.257e-02)Gly+(1.600e-02)Ala-(6.350e-01)ABA+(4.553e-01)Leu-(4.117e-01)Trp-(2.717e+01) | 0.875861 |
| 71 | (4.567e-01)Glu-(7.197e-02)Gly+(1.018e-01)Arg-(6.678e-01)ABA+(4.240e-01)Leu-(3.875e-01)Trp-(2.745e+01) | 0.875754 |
| 72 | -(5.695e-01)Glu+(2.446e-02)Gln-(2.139e-01)Tyr-(2.689e-01)Orn-(5.059e-01)Leu+(5.487e-01)Trp+(7.103e+01) | 0.875754 |
| 73 | -(5.860e-01)Glu+(2.225e-01)Ser+(3.385e-03)Gln-(6.077e-01)Leu+(2.158e-01)Phe+(4.374e-01)Trp+(3.192e+01) | 0.875646 |
| 74 | -(5.588e-01)Glu-(1.643e-01)Pro-(2.339e-01)Orn-(5.523e-01)Leu+(2.334e-01)Phe+(4.965e-01)Trp+(8.388e+01) | 0.875646 |
| 75 | -(4.956e-01)Glu+(1.576e-01)Ser+(5.013e-01)ABA-(1.824e-01)Tyr-(4.693e-01)Leu+(4.741e-01)Trp+(3.589e+01) | 0.875538 |
| 76 | -(4.889e-01)Glu+(5.448e-01)ABA-(1.571e-01)Tyr-(1.902e-01)Orn-(4.251e-01)Leu+(4.718e-01)Trp+(5.663e+01) | 0.875538 |
| 77 | -(5.200e-01)Glu+(2.444e-01)Ser-(3.777e-01)Asn-(2.546e-01)Orn-(4.764e-01)Leu+(4.853e-01)Trp+(5.547e+01) | 0.875538 |
| 78 | (5.452e-01)Glu+(1.947e-01)Pro-(9.308e-02)Gly+(1.385e-01)Tyr-(5.494e-01)Leu-(5.790e-01)Trp-(7.241e+01) | 0.875538 |
| 79 | -(5.460e-01)Glu-(1.539e-01)Pro-(2.396e-01)Orn+(1.457e-01)Ile-(5.695e-01)Leu+(5.246e-01)Trp+(8.835e+01) | 0.875431 |
| 80 | -(5.832e-01)Glu+(1.807e-01)Ser+(5.531e-02)Gly-(6.129e-01)Leu+(2.430e-01)Phe+(4.354e-01)Trp+(2.478e+01) | 0.875431 |
| 81 | -(5.530e-01)Glu-(2.092e-01)Pro+(1.036e-01)Gly+(4.020e-03)Ala-(5.802e-01)Leu+(5.504e-01)Trp+(6.620e+01) | 0.875431 |
| 82 | -(5.870e-01)Glu+(2.232e-01)Ser-(6.052e-01)Leu+(2.181e-01)Phe+(4.379e-01)Trp+(3.333e+01) | 0.875431 |
| 83 | (5.695e-01)Glu+(2.080e-01)Pro-(1.067e-01)Gly+(7.206e-02)Lys+(5.292e-01)Leu-(5.795e-01)Trp-(7.461e+01) | 0.875323 |
| 84 | (4.564e-01)Glu-(6.834e-02)Gly-(6.784e-03)Gln-(6.508e-01)ABA+(4.606e-01)Leu-(3.889e-01)Trp-(1.974e+01) | 0.875323 |
| 85 | (5.172e-01)Glu-(1.839e-01)Ser+(1.261e-01)Arg-(5.115e-01)ABA+(4.782e-01)Leu-(4.386e-01)Trp-(3.501e+01) | 0.875323 |
| 86 | -(5.418e-01)Glu-(2.163e-01)Pro+(1.003e-01)Gly+(2.002e-02)Gln-(5.913e-01)Leu+(5.474e-01)Trp+(5.907e+01) | 0.875323 |
| 87 | -(5.800e-01)Glu+(2.179e-01)Ser+(2.719e-01)Tau-(5.796e-01)Leu+(1.973e-01)Phe+(4.090e-01)Trp+(2.039e+01) | 0.875215 |
| 88 | -(5.532e-01)Glu-(2.070e-01)Pro+(1.045e-01)Gly-(8.783e-03)Val-(5.717e-01)Leu+(5.597e-01)Trp+(6.774e+01) | 0.875 |
| 89 | -(5.116e-01)Glu+(2.320e-01)Ser-(1.678e-01)Pro+(2.569e-01)Cit-(5.335e-01)Leu+(5.529e-01)Trp+(4.584e+01) | 0.875 |
| 90 | -(5.475e-01)Glu+(2.511e-01)Ser-(7.157e-02)Thr-(2.759e-01)Orn-(5.273e-01)Leu+(5.272e-01)Trp+(5.257e+01) | 0.875 |
| 91 | -(5.376e-01)Glu-(1.972e-01)Pro+(9.828e-02)Gly+(1.229e-01)Ile-(6.101e-01)Leu+(5.245e-01)Trp+(6.366e+01) | 0.874892 |
| 92 | (5.527e-01)Glu+(2.069e-01)Pro-(8.436e-03)Asn-(1.038e-01)Gly+(5.787e-01)Leu-(5.531e-01)Trp-(6.659e+01) | 0.874892 |
| 93 | -(5.631e-01)Glu-(2.018e-01)Pro+(1.070e-01)Gly-(1.047e-01)Arg-(5.568e-01)Leu+(5.565e-01)Trp+(7.266e+01) | 0.874892 |
| 94 | -(5.596e-01)Glu-(2.828e-01)Ser-(1.905e-01)Pro-(2.450e-01)Orn-(5.524e-01)Leu+(4.532e-01)Phe+(7.511e+01) | 0.874785 |
| 95 | (5.530e-01)Glu+(2.065e-01)Pro-(1.038e-01)Gly+(5.785e-01)Leu-(5.533e-01)Trp-(6.686e+01) | 0.874785 |
| 96 | (5.687e-01)Glu-(2.207e-01)Ser-(1.877e-01)Cit+(5.832e-01)Leu-(2.117e-01)Phe-(4.558e-01)Trp-(2.485e+01) | 0.874785 |
| 97 | (5.521e-01)Glu+(2.084e-01)Pro-(1.034e-01)Gly-(7.083e-02)Met+(5.814e-01)Leu-(5.459e-01)Trp-(6.607e+01) | 0.874785 |
| 98 | -(5.566e-01)Glu-(2.115e-01)Pro+(1.024e-01)Gly+(3.459e-02)Thr-(5.730e-01)Leu+(5.474e-01)Trp+(6.481e+01) | 0.874677 |
| 99 | -(5.629e-01)Glu+(2.528e-01)Ser-(9.664e-02)Thr-(5.985e-01)Leu+(2.131e-01)Phe+(4.542e-01)Trp+(3.752e+01) | 0.874677 |
| 100 | -(4.551e-01)Glu+(7.223e-02)Gly-(5.875e-02)Cit+(6.588e-01)ABA-(4.541e-01)Leu+(3.795e-01)Trp+(2.375e+01) | 0.874677 |

FIG.47

| No | FORMULA | R |
|---|---|---|
| 1 | 0.871(Leu)+0.796(Glu)-1.163(Trp)-0.486(Ser)+0.267(Pro)+0.641(Tyr)-0.112(Gln)+85.759 | 0.71 |
| 2 | 0.348(BCAA)-0.140(Gln)+0.149(Ala)-1.016(Trp)+0.586(Glu)-0.140(Gly)+64.815 | 0.72 |
| 3 | (Glu/Gly)-0.218(Ser/Tyr)-0.149(His/Trp) | 0.5 |

METHOD OF EVALUATING VISCERAL FAT ACCUMULATION, VISCERAL FAT ACCUMULATION-EVALUATING APPARATUS, VISCERAL FAT ACCUMULATION-EVALUATING METHOD, VISCERAL FAT ACCUMULATION-EVALUATING SYSTEM, VISCERAL FAT ACCUMULATION-EVALUATING PROGRAM, RECORDING MEDIUM, AND METHOD OF SEARCHING FOR PROPHYLACTIC/AMELIORATING SUBSTANCE FOR VISCERAL FAT ACCUMULATION

This application is a Continuation of PCT/JP2008/061561, filed Jun. 25, 2008, which claims priority from Japanese patent application JP 2007-166219 filed Jun. 25, 2007. The contents of each of the aforementioned application are incorporated herein by reference in their entirety.

BACKGROUND OF THE INVENTION

1. Field of the Invention

The present invention relates to a method of evaluating visceral fat accumulation, a visceral fat accumulation-evaluating apparatus, a visceral fat accumulation-evaluating method, a visceral fat accumulation-evaluating system, a visceral fat accumulation-evaluating program, and a recording medium, which utilize concentrations of amino acids in blood (plasma).

The present invention also relates to a method of searching for prophylactic/ameliorating substance for visceral fat accumulation, wherein a substance for preventing a visceral fat accumulation or ameliorating a visceral fat accumulation condition is searched.

2. Description of the Related Art

In recent years, along with an increase in the opportunities to take high-fat diet or a decrease in the opportunities for exercise, the problem of a visceral fat accumulation, which is one of the diagnostic criteria for metabolic syndrome, is rising as an issue. If the visceral fat level is high, even though the degree of hypertension, diabetes, hyperlipidemia or the like may be low, the risk of myocardial infarction or cerebral infarction drastically increases. Thus, it is thought that the visceral fat accumulation is causative of many lifestyle diseases. Therefore, the problem of how to reduce the risk of the visceral fat accumulation and to prevent the visceral fat accumulation is attracting attention as an urgent issue for healthcare insurance.

Since the visceral fat accumulation due to obesity causes hypertension, diabetes and hyperlipidemia, which in turn develop into arteriosclerosis, it is considered that the visceral fat accumulation constitutes a particularly important criterion among the diagnostic criteria for metabolic syndrome. It is also known that concomitantly with the visceral fat accumulation, hyperinsulinemia occurs, or the balance in the adipocytokine secreted from adipose tissues is disrupted.

At the 102nd annual meeting of the Japanese Society of Internal Medicine in April, 2005, the diagnostic criteria for metabolic syndrome in the Japanese population (see "Metabolic Syndrome Diagnostic Criteria Review Committee, Journal of the Japanese Society of Internal medicine, 94, 794, 2005.") were established by eight related academic societies, including the Japanese Society of Internal Medicine (eight academic societies including Japan Society for the Study of Obesity, Japan Atherosclerosis Society, Japan Diabetes Society, the Japanese Society of Hypertension, the Japanese Circulation Society, Japanese Society of Nephrology, the Japanese Society on Thrombosis and Hemostasis, and the Japanese Society of Internal Medicine). At the annual meeting, the diagnostic criterion for visceral fat accumulation was determined to be a visceral fat area of 100 $cm^2$ or more, and the waist circumference (abdominal circumference) corresponding to this area was determined to be 85 cm or more for men and 90 cm or more for women. If the criterion for visceral fat accumulation is satisfied, and two or more items among the three items listed below are met, the condition is determined as metabolic syndrome. Furthermore, if only one item among the following three items is met, the condition is regarded as premetabolic syndrome.

1. The systolic blood pressure is 130 mmHg or higher, or the diastolic blood pressure is 85 mmHg or higher.
2. The fasting blood glucose level is 110 mg/dL or higher.
3. The triglyceride level is 150 mg/mL or higher, or the HDL-cholesterol level is lower than 40 mg/dL.

According to the "National Health and Nutrition Examination Survey, 2004" reported by the Ministry of Health, Labour and Welfare in May, 2006, the population of patients at age 40 to 74 with visceral fat syndrome or pre-visceral fat syndrome reached about 20 million, which corresponds to one-third of the entire population of this generation. The proportion of those who were strongly suspected was 25.7% for male and 10.0% for female, and the proportion of those who were considered to have pre-visceral fat syndrome was 26.0% for male and 9.6% for female.

Since the visceral fat accumulation is causative of lifestyle diseases, and also the proportion of those patients with visceral fat syndrome is high, it may be said to be an important task to measure the visceral fat accumulation inexpensively, conveniently and quickly, and to suggest guidelines for amelioration from the findings on the level of metabolism. The diagnosis of the visceral fat accumulation involves the use of the abdominal visceral fat area or the abdominal circumference. However, each of these indicators has problems, such as that the measurement of visceral fat area frequently requires computer tomography (CT) and demand cost, time and labor, while the measurement of the abdominal circumference is subject to change in the value depending on the measurer and is associated with a possibility that subcutaneous fat accumulation is confused with the visceral fat accumulation, bringing about an overlook of hidden obesity.

Meanwhile, amino acid metabolism is affected in peripheral tissues, by the insulin resistance derived from the visceral fat accumulation. Prior technology literatures report the results of the researches on the amino acid metabolism in obesity patients or diabetic rats, in which changes are seen in the blood plasma levels of amino acids related to obesity or insulin resistance attributed thereto (see "Felig, P., Marliss, E., et al., New Engl. J. Med., 281, 881 (1969)." or "Felig, P., Marliss, E., et al., Diabetes, 19, 727 (1970).").

If amino acids that specifically vary in the peripheral blood level or the like in the group of patients with the visceral fat accumulation, were discovered, and index formulae using the concentration parameters of the varying amino acids could be established, the index formulae would be able to be widely applied as a convenient and sensitive detection method that reflects the background metabolic changes in the visceral fat accumulation. In regard to the method of diagnosing a disease state using blood amino acids, the indices described in WO 2004/052191 and WO 2006/098192 are known. However, in WO 2004/052191, the object of clinical diagnosis is an index intended to discriminate between hepatitis C patients and hepatitis-free subjects, while in WO 2006/098192, the object of clinical diagnosis is an index intended to discriminate between Crohn's disease patients and healthy subjects, and to discriminate between ulcerative colitis patients and healthy subjects.

However, there is a problem that there are reports on changes of amino acids in obesity or diabetes, and there is no report on a metabolic pattern of amino acids in peripheral blood in a visceral fat accumulation condition. Specifically, there is also a problem that there is no report on application to a diagnostic method for a discrimination between 2 groups of a visceral fat accumulation group and a visceral fat accumulation-free group or for an evaluation of a visceral fat area state.

There is a problem that technology of diagnosing the visceral fat accumulation condition with a plurality of amino acids as explanatory variables is not developed and not practically used.

SUMMARY OF THE INVENTION

It is an object of the present invention to at least partially solve the problems in the conventional technology. The present invention is made in view of the problem described above. An object of the present invention is to provide a method of evaluating visceral fat accumulation, a visceral fat accumulation-evaluating apparatus, a visceral fat accumulation-evaluating method, a visceral fat accumulation-evaluating system, a visceral fat accumulation-evaluating program, and a recording medium, which are capable of evaluating a visceral fat accumulation condition accurately by utilizing concentrations of amino acids in blood. An object of the present invention is to provide a method of searching for prophylactic/ameliorating substance for visceral fat accumulation which is capable of searching for prophylactic/ameliorating substance for visceral fat accumulation efficiently.

The present inventors have made extensive study for solving the problems described above, and as a result they have identified amino acids which are useful in the discrimination between the 2 groups of the visceral fat accumulation group and the visceral fat accumulation-free group, or in the evaluation of the visceral fat area state (specifically, the amino acids varying with a statistically significant difference between the 2 groups of the visceral fat accumulation group and the visceral fat accumulation-free group, the amino acids with a statistically significant correlation with the visceral fat area state), and have found that multivariate discriminants (correlation equations, index formulae) including concentrations of the identified amino acids as explanatory variables correlate significantly with a progress of the visceral fat accumulation condition, and the present invention was thereby completed.

To solve the problems and achieve the objects described above, a method of evaluating visceral fat accumulation according to one aspect of the present invention includes a measuring step of measuring amino acid concentration data on a concentration value of an amino acid in blood collected from a subject to be evaluated, and a concentration value criterion evaluating step of evaluating a visceral fat accumulation condition in the subject based on the amino acid concentration data of the subject measured at the measuring step.

Another aspect of the present invention is the method of evaluating visceral fat accumulation, wherein at the concentration value criterion evaluating step, the visceral fat accumulation condition in the subject is evaluated based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured at the measuring step.

Still another aspect of the present invention is the method of evaluating visceral fat accumulation, wherein the concentration value criterion evaluating step further includes a concentration value criterion discriminating step of discriminating between a visceral fat accumulation group and a visceral fat accumulation-free group in the subject based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured at the measuring step.

Still another aspect of the present invention is the method of evaluating visceral fat accumulation, wherein at the concentration value criterion evaluating step, a visceral fat area stete in the subject is evaluated based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured at the measuring step.

Still another aspect of the present invention is the method of evaluating visceral fat accumulation, wherein the concentration value criterion evaluating step further includes a discriminant value calculating step of calculating a discriminant value that is a value of a multivariate discriminant with a concentration of the amino acid as an explanatory variable, based on both the amino acid concentration data of the subject measured at the measuring step and the previously established multivariate discriminant, and a discriminant value criterion evaluating step of evaluating the visceral fat accumulation condition in the subject based on the discriminant value calculated at the discriminant value calculating step.

Still another aspect of the present invention is the method of evaluating visceral fat accumulation, wherein the multivariate discriminant contains at least one of Val, Leu, Ile, Tyr, Phe, Trp, Glu, Ala, Pro, Orn, Lys, Gly, Ser, Met, Arg, Cys, and Gln as the explanatory variable, and wherein at the discriminant value calculating step, the discriminant value is calculated based on both the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured at the measuring step and the multivariate discriminant.

Still another aspect of the present invention is the method of evaluating visceral fat accumulation, wherein the discriminant value criterion evaluating step further includes a discriminant value criterion discriminating step of discriminating between a visceral fat accumulation group and a visceral fat accumulation-free group in the subject based on the discriminant value calculated at the discriminant value calculating step.

Still another aspect of the present invention is the method of evaluating visceral fat accumulation, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of evaluating visceral fat accumulation, wherein the multivariate discriminant is formula 1, formula 2, the logistic regression equation with Ser, Glu, Ile, Tyr, and Arg as the explanatory variables, or the logistic regression equation with Ser, Glu, Leu, and Trp as the explanatory variables.

(Glu+Tyr+Orn)/(Asn+Ser)   (formula 1)

(Glu+Leu)/(Ser+Tau)+(Pro+Orn)/(Gln)   (formula 2)

Still another aspect of the present invention is the method of evaluating visceral fat accumulation, wherein at the discriminant value criterion evaluating step, a visceral fat area stete in the subject is evaluated based on the discriminant value calculated at the discriminant value calculating step.

Still another aspect of the present invention is the method of evaluating visceral fat accumulation, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of evaluating visceral fat accumulation, wherein the multivariate discriminant is formula 3 or formula 4.

(Glu+Gly)+(−0.2)×(Ser/Tyr)+(−0.1)×(His/Trp)   (formula 3)

(Glu/Gly)+(−0.54)×(Ser/Leu)+(0.15)×(Pro/Trp)+(−0.05)×(Gln/Tyr)   (formula 4)

The present invention also relates to a visceral fat accumulation-evaluating apparatus, the visceral fat accumulation-evaluating apparatus according to one aspect of the present invention includes a control unit and a memory unit to evaluate a visceral fat accumulation condition in a subject to be evaluated. The control unit includes a discriminant value-calculating unit that calculates a discriminant value that is a value of a multivariate discriminant with a concentration of an amino acid as an explanatory variable, based on both previously obtained amino acid concentration data of the subject on a concentration value of the amino acid and the multivariate discriminant stored in the memory unit, and a discriminant value criterion-evaluating unit that evaluates the visceral fat accumulation condition in the subject based on the discriminant value calculated by the discriminant value-calculating unit.

Another aspect of the present invention is the visceral fat accumulation-evaluating apparatus, wherein the multivariate discriminant contains at least one of Val, Leu, Ile, Tyr, Phe, Trp, Glu, Ala, Pro, Orn, Lys, Gly, Ser, Met, Arg, Cys, and Gln as the explanatory variable, and wherein the discriminant value-calculating unit calculates the discriminant value based on both the concentration value of at least one of Val, Leu, Ile, Tyr, Phe, Trp, Glu, Ala, Pro, Orn, Lys, Gly, Ser, Met, Arg, Cys, and Gln contained in the previously obtained amino acid concentration data of the subject and the multivariate discriminant.

Still another aspect of the present invention is the visceral fat accumulation-evaluating apparatus, wherein the discriminant value criterion-evaluating unit further includes a discriminant value criterion-discriminating unit that discriminates between a visceral fat accumulation group and a visceral fat accumulation-free group in the subject based on the discriminant value calculated by the discriminant value-calculating unit.

Still another aspect of the present invention is the visceral fat accumulation-evaluating apparatus, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the visceral fat accumulation-evaluating apparatus, wherein the multivariate discriminant is formula 1, formula 2, the logistic regression equation with Ser, Glu, Ile, Tyr, and Arg as the explanatory variables, or the logistic regression equation with Ser, Glu, Leu, and Trp as the explanatory variables.

(Glu+Tyr+Orn)/(Asn+Ser)   (formula 1)

(Glu+Leu)/(Ser+Tau)+(Pro+Orn)/(Gln)   (formula 2)

Still another aspect of the present invention is the visceral fat accumulation-evaluating apparatus, wherein the discriminant value criterion-evaluating unit evaluates a visceral fat area stete in the subject based on the discriminant value calculated by the discriminant value-calculating unit.

Still another aspect of the present invention is the visceral fat accumulation-evaluating apparatus, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the visceral fat accumulation-evaluating apparatus, wherein the multivariate discriminant is formula 3 or formula 4.

(Glu+Gly)+(−0.2)×(Ser/Tyr)+(−0.1)×(His/Trp)   (formula 3)

(Glu/Gly)+(−0.54)×(Ser/Leu)+(0.15)×(Pro/Trp)+(−0.05)×(Gln/Tyr)   (formula 4)

Still another aspect of the present invention is the visceral fat accumulation-evaluating apparatus, wherein the control unit further includes a multivariate discriminant-preparing unit that prepares the multivariate discriminant stored in the memory unit, based on visceral fat accumulation condition information stored in the memory unit containing the amino acid concentration data and visceral fat accumulation condition index data on an index for indicating the visceral fat accumulation condition. The multivariate discriminant-preparing unit further includes a candidate multivariate discriminant-preparing unit that prepares a candidate multivariate discriminant that is a candidate of the multivariate discriminant, based on a predetermined discriminant-preparing method from the visceral fat accumulation condition information, a candidate multivariate discriminant-verifying unit that verifies the candidate multivariate discriminant prepared by the candidate multivariate discriminant-preparing unit, based on a predetermined verifying method, and an explanatory variable-selecting unit that selects the explanatory variable of the candidate multivariate discriminant based on a predetermined explanatory variable-selecting method from a verification result obtained by the candidate multivariate discriminant-verifying unit, thereby selecting a combination of the amino acid concentration data contained in the visceral fat accumulation condition information used in preparing the candidate multivariate discriminant. The multivariate discriminant-preparing unit prepares the multivariate discriminant by selecting the candidate multivariate discriminant used as the multivariate discriminant, from a plurality of the candidate multivariate discriminants, based on the verification results accumulated by repeatedly executing the candidate multivariate discriminant-preparing unit, the candidate multivariate discriminant-verifying unit, and the explanatory variable-selecting unit.

The present invention also relates to a visceral fat accumulation-evaluating method, one aspect of the present invention is the visceral fat accumulation-evaluating method of evaluating a visceral fat accumulation condition in a subject to be evaluated. The method is carried out with an information processing apparatus including a control unit and a memory unit. The method includes (i) a discriminant value calculating step of calculating a discriminant value that is a value of a multivariate discriminant with a concentration of an amino acid as an explanatory variable, based on both previously obtained amino acid concentration data of the subject on a concentration value of the amino acid and the multivariate discriminant stored in the memory unit, and (ii) a discriminant value criterion evaluating step of evaluating the visceral fat accumulation condition in the subject based on the discriminant value calculated at the discriminant value calculating step. The steps (i) and (ii) are executed by the control unit.

Another aspect of the present invention is the visceral fat accumulation-evaluating method, wherein the multivariate discriminant contains at least one of Val, Leu, Ile, Tyr, Phe, Trp, Glu, Ala, Pro, Orn, Lys, Gly, Ser, Met, Arg, Cys, and Gln as the explanatory variable, and wherein at the discriminant value calculating step, the discriminant value is calculated based on both the concentration value of at least one of Val, Leu, Ile, Tyr, Phe, Trp, Glu, Ala, Pro, Orn, Lys, Gly, Ser, Met, Arg, Cys, and Gln contained in the previously obtained amino acid concentration data of the subject and the multivariate discriminant.

Still another aspect of the present invention is the visceral fat accumulation-evaluating method, wherein the discriminant value criterion evaluating step further includes a discriminant value criterion discriminating step of discriminating between a visceral fat accumulation group and a visceral fat accumulation-free group in the subject based on the discriminant value calculated at the discriminant value calculating step.

Still another aspect of the present invention is the visceral fat accumulation-evaluating method, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the visceral fat accumulation-evaluating method, wherein the multivariate discriminant is formula 1, formula 2, the logistic regression equation with Ser, Glu, Ile, Tyr, and Arg as the explanatory variables, or the logistic regression equation with Ser, Glu, Leu, and Trp as the explanatory variables.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

Still another aspect of the present invention is the visceral fat accumulation-evaluating method, wherein at the discriminant value criterion evaluating step, a visceral fat area stete in the subject is evaluated based on the discriminant value calculated at the discriminant value calculating step.

Still another aspect of the present invention is the visceral fat accumulation-evaluating method, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the visceral fat accumulation-evaluating method, wherein the multivariate discriminant is formula 3 or formula 4.

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

Still another aspect of the present invention is the visceral fat accumulation-evaluating method, wherein the method further includes a multivariate discriminant preparing step of preparing the multivariate discriminant stored in the memory unit, based on visceral fat accumulation condition information stored in the memory unit containing the amino acid concentration data and visceral fat accumulation condition index data on an index for indicating the visceral fat accumulation condition. The multivariate discriminant preparing step is executed by the control unit. The multivariate discriminant preparing step further includes a candidate multivariate discriminant preparing step of preparing a candidate multivariate discriminant that is a candidate of the multivariate discriminant, based on a predetermined discriminant-preparing method from the visceral fat accumulation condition information, a candidate multivariate discriminant verifying step of verifying the candidate multivariate discriminant prepared at the candidate multivariate discriminant preparing step, based on a predetermined verifying method, and an explanatory variable selecting step of selecting the explanatory variable of the candidate multivariate discriminant based on a predetermined explanatory variable-selecting method from a verification result obtained at the candidate multivariate discriminant verifying step, thereby selecting a combination of the amino acid concentration data contained in the visceral fat accumulation condition information used in preparing the candidate multivariate discriminant. At the multivariate discriminant preparing step, the multivariate discriminant is prepared by selecting the candidate multivariate discriminant used as the multivariate discriminant from a plurality of the candidate multivariate discriminants, based on the verification results accumulated by repeatedly executing the candidate multivariate discriminant preparing step, the candidate multivariate discriminant verifying step, and the explanatory variable selecting step.

The present invention also relates to a visceral fat accumulation-evaluating system, the visceral fat accumulation-evaluating system according to one aspect of the present invention includes a visceral fat accumulation-evaluating apparatus including a control unit and a memory unit to evaluate a visceral fat accumulation condition in a subject to be evaluated and an information communication terminal apparatus that provides amino acid concentration data of the subject on a concentration value of an amino acid connected to each other communicatively via a network. The information communication terminal apparatus includes an amino acid concentration data-sending unit that transmits the amino acid concentration data of the subject to the visceral fat accumulation-evaluating apparatus, and an evaluation result-receiving unit that receives an evaluation result on the visceral fat accumulation condition of the subject transmitted from the visceral fat accumulation-evaluating apparatus. The control unit of the visceral fat accumulation-evaluating apparatus includes an amino acid concentration data-receiving unit that receives the amino acid concentration data of the subject transmitted from the information communication terminal apparatus, a discriminant value-calculating unit that calculates a discriminant value that is a value of a multivariate discriminant with a concentration of the amino acid as an explanatory variable, based on both the amino acid concentration data of the subject received by the amino acid concentration data-receiving unit and the multivariate discriminant stored in the memory unit, a discriminant value criterion-evaluating unit that evaluates the visceral fat accumulation condition in the subject based on the discriminant value calculated by the discriminant value-calculating unit, and an evaluation result-sending unit that transmits the evaluation result of the subject obtained by the discriminant value criterion-evaluating unit to the information communication terminal apparatus.

Another aspect of the present invention is the visceral fat accumulation-evaluating system, wherein the multivariate discriminant contains at least one of Val, Leu, Ile, Tyr, Phe, Trp, Glu, Ala, Pro, Orn, Lys, Gly, Ser, Met, Arg, Cys, and Gln as the explanatory variable, and wherein the discriminant value-calculating unit calculates the discriminant value based on both the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject received by the amino acid concentration data-receiving unit and the multivariate discriminant.

Still another aspect of the present invention is the visceral fat accumulation-evaluating system, wherein the discriminant value criterion-evaluating unit further includes a discriminant value criterion-discriminating unit that discriminates between a visceral fat accumulation group and a visceral fat accumulation-free group in the subject based on the discriminant value calculated by the discriminant value-calculating unit.

Still another aspect of the present invention is the visceral fat accumulation-evaluating system, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the visceral fat accumulation-evaluating system, wherein the multivariate discriminant is formula 1, formula 2, the logistic regression equation with Ser, Glu, Ile, Tyr, and Arg as the explanatory variables, or the logistic regression equation with Ser, Glu, Leu, and Trp as the explanatory variables.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

Still another aspect of the present invention is the visceral fat accumulation-evaluating system, wherein the discriminant value criterion-evaluating unit evaluates a visceral fat area stete in the subject based on the discriminant value calculated by the discriminant value-calculating unit.

Still another aspect of the present invention is the visceral fat accumulation-evaluating system, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the visceral fat accumulation-evaluating system, wherein the multivariate discriminant is formula 3 or formula 4.

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

Still another aspect of the present invention is the visceral fat accumulation-evaluating system, wherein the control unit of the visceral fat accumulation-evaluating apparatus further includes a multivariate discriminant-preparing unit that prepares the multivariate discriminant stored in the memory unit, based on visceral fat accumulation condition information stored in the memory unit containing the amino acid concentration data and visceral fat accumulation condition index data on an index for indicating the visceral fat accumulation condition. The multivariate discriminant-preparing unit further includes a candidate multivariate discriminant-preparing unit that prepares a candidate multivariate discriminant that is a candidate of the multivariate discriminant, based on a predetermined discriminant-preparing method from the visceral fat accumulation condition information, a candidate multivariate discriminant-verifying unit that verifies the candidate multivariate discriminant prepared by the candidate multivariate discriminant-preparing unit, based on a predetermined verifying method, and an explanatory variable-selecting unit that selects the explanatory variable of the candidate multivariate discriminant based on a predetermined explanatory variable-selecting method from a verification result obtained by the candidate multivariate discriminant-verifying unit, thereby selecting a combination of the amino acid concentration data contained in the visceral fat accumulation condition information used in preparing the candidate multivariate discriminant. The multivariate discriminant-preparing unit prepares the multivariate discriminant by selecting the candidate multivariate discriminant used as the multivariate discriminant, from a plurality of the candidate multivariate discriminants, based on the verification results accumulated by repeatedly executing the candidate multivariate discriminant-preparing unit, the candidate multivariate discriminant-verifying unit, and the explanatory variable-selecting unit.

The present invention also relates to a visceral fat accumulation-evaluating program product, one aspect of the present invention is the visceral fat accumulation-evaluating program product that makes an information processing apparatus including a control unit and a memory unit execute a method of evaluating a visceral fat accumulation condition in a subject to be evaluated. The method includes (i) a discriminant value calculating step of calculating a discriminant value that is a value of a multivariate discriminant with a concentration of an amino acid as an explanatory variable, based on both previously obtained amino acid concentration data of the subject on a concentration value of the amino acid and the multivariate discriminant stored in the memory unit, and (ii) a discriminant value criterion evaluating step of evaluating the visceral fat accumulation condition in the subject based on the discriminant value calculated at the discriminant value calculating step. The steps (i) and (ii) are executed by the control unit.

Another aspect of the present invention is the visceral fat accumulation-evaluating program product, wherein the multivariate discriminant contains at least one of Val, Leu, Ile, Tyr, Phe, Trp, Glu, Ala, Pro, Orn, Lys, Gly, Ser, Met, Arg, Cys, and Gln as the explanatory variable, and wherein at the discriminant value calculating step, the discriminant value is calculated based on both the concentration value of at least one of Val, Leu, Ile, Tyr, Phe, Trp, Glu, Ala, Pro, Orn, Lys, Gly, Ser, Met, Arg, Cys, and Gln contained in the previously obtained amino acid concentration data of the subject and the multivariate discriminant.

Still another aspect of the present invention is the visceral fat accumulation-evaluating program product, wherein the discriminant value criterion evaluating step further includes a discriminant value criterion discriminating step of discriminating between a visceral fat accumulation group and a visceral fat accumulation-free group in the subject based on the discriminant value calculated at the discriminant value calculating step.

Still another aspect of the present invention is the visceral fat accumulation-evaluating program product, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the visceral fat accumulation-evaluating program product, wherein the multivariate discriminant is formula 1, formula 2, the logistic regression equation with Ser, Glu, Ile, Tyr, and Arg as the explanatory variables, or the logistic regression equation with Ser, Glu, Leu, and Trp as the explanatory variables.

$$(Glu+Tyr+Orn)/(Asn+Ser) \qquad \text{(formula 1)}$$

$$(Glu+Leu)/(Ser+Tau)+(Pro+Orn)/(Gln) \qquad \text{(formula 2)}$$

Still another aspect of the present invention is the visceral fat accumulation-evaluating program product, wherein at the discriminant value criterion evaluating step, a visceral fat area stete in the subject is evaluated based on the discriminant value calculated at the discriminant value calculating step.

Still another aspect of the present invention is the visceral fat accumulation-evaluating program product, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the visceral fat accumulation-evaluating program product, wherein the multivariate discriminant is formula 3 or formula 4.

$$(Glu+Gly)+(-0.2)\times(Ser/Tyr)+(-0.1)\times(His/Trp) \qquad \text{(formula 3)}$$

$$(Glu/Gly)+(-0.54)\times(Ser/Leu)+(0.15)\times(Pro/Trp)+(-0.05)\times(Gln/Tyr) \qquad \text{(formula 4)}$$

Still another aspect of the present invention is the visceral fat accumulation-evaluating program product, wherein the method further includes a multivariate discriminant preparing step of preparing the multivariate discriminant stored in the memory unit, based on visceral fat accumulation condition information stored in the memory unit containing the amino acid concentration data and visceral fat accumulation condition index data on an index for indicating the visceral fat accumulation condition. The multivariate discriminant preparing step is executed by the control unit. The multivariate discriminant preparing step further includes a candidate multivariate discriminant preparing step of preparing a candidate multivariate discriminant that is a candidate of the multivariate discriminant, based on a predetermined discriminant-preparing method from the visceral fat accumulation condition information, a candidate multivariate discriminant verifying step of verifying the candidate multivariate discriminant prepared at the candidate multivariate discriminant preparing step, based on a predetermined verifying method, and an explanatory variable selecting step of selecting the explanatory variable of the candidate multivariate discriminant based on a predetermined explanatory variable-selecting method from a verification result obtained at the candidate multivariate discriminant verifying step, thereby selecting a combination of the amino acid concentration data contained in the visceral fat accumulation condition information used in preparing the candidate multivariate discriminant. At the multivariate discriminant preparing step, the multivariate discriminant is prepared by selecting the candidate multivariate discriminant used as the multivariate discriminant from a plurality of the candidate multivariate discriminants, based on the verification results accumulated by repeatedly executing the candidate multivariate discriminant preparing step, the candidate multivariate discriminant verifying step, and the explanatory variable selecting step.

The present invention also relates to a recording medium, the recording medium according to one aspect of the present invention includes the visceral fat accumulation-evaluating program product described above.

The present invention also relates to a method of searching for prophylactic/ameliorating substance for visceral fat accumulation. One aspect of the present invention is the method of searching for prophylactic/ameliorating substance for visceral fat accumulation, wherein the method includes a measuring step of measuring amino acid concentration data on a concentration value of an amino acid in blood collected from a subject to be evaluated to which a desired substance group consisting of one or more substances that prevent a visceral fat accumulation or ameliorate a visceral fat accumulation condition has been administered, a concentration value criterion evaluating step of evaluating a visceral fat accumulation condition in the subject based on the amino acid concentration data measured at the measuring step, and a judging step of judging whether or not the desired substance group prevents the visceral fat accumulation or ameliorates the visceral fat accumulation condition, based on an evaluation result obtained at the concentration value criterion evaluating step.

Another aspect of the present invention is the method of searching for prophylactic/ameliorating substance for visceral fat accumulation, wherein at the concentration value criterion evaluating step, the visceral fat accumulation condition in the subject is evaluated based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured at the measuring step.

Still another aspect of the present invention is the method of searching for prophylactic/ameliorating substance for visceral fat accumulation, wherein the concentration value criterion evaluating step further includes a concentration value criterion discriminating step of discriminating between a visceral fat accumulation group and a visceral fat accumulation-free group in the subject based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured at the measuring step.

Still another aspect of the present invention is the method of searching for prophylactic/ameliorating substance for visceral fat accumulation, wherein at the concentration value criterion evaluating step, a visceral fat area stete in the subject is evaluated based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured at the measuring step.

Still another aspect of the present invention is the method of searching for prophylactic/ameliorating substance for visceral fat accumulation, wherein the concentration value criterion evaluating step further includes a discriminant value calculating step of calculating a discriminant value that is a value of a multivariate discriminant with a concentration of the amino acid as an explanatory variable, based on both the amino acid concentration data of the subject measured at the measuring step and the previously established multivariate discriminant, and a discriminant value criterion evaluating step of evaluating the visceral fat accumulation condition in the subject based on the discriminant value calculated at the discriminant value calculating step.

Still another aspect of the present invention is the method of searching for prophylactic/ameliorating substance for visceral fat accumulation, wherein the multivariate discriminant contains at least one of Val, Leu, Ile, Tyr, Phe, Trp, Glu, Ala, Pro, Orn, Lys, Gly, Ser, Met, Arg, Cys, and Gln as the explanatory variable, and wherein at the discriminant value calculating step, the discriminant value is calculated based on both the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured at the measuring step and the multivariate discriminant.

Still another aspect of the present invention is the method of searching for prophylactic/ameliorating substance for visceral fat accumulation, wherein the discriminant value criterion evaluating step further includes a discriminant value criterion discriminating step of discriminating between a visceral fat accumulation group and a visceral fat accumulation-free group in the subject based on the discriminant value calculated at the discriminant value calculating step.

Still another aspect of the present invention is the method of searching for prophylactic/ameliorating substance for visceral fat accumulation, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of searching for prophylactic/ameliorating substance for visceral fat accumulation, wherein the multivariate discriminant is formula 1, formula 2, the logistic regression equation with Ser, Glu, Ile, Tyr, and Arg as the explanatory variables, or the logistic regression equation with Ser, Glu, Leu, and Trp as the explanatory variables.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

Still another aspect of the present invention is the method of searching for prophylactic/ameliorating substance for visceral fat accumulation, wherein at the discriminant value criterion evaluating step, a visceral fat area stete in the subject is evaluated based on the discriminant value calculated at the discriminant value calculating step.

Still another aspect of the present invention is the method of searching for prophylactic/ameliorating substance for visceral fat accumulation, wherein the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of searching for prophylactic/ameliorating substance for visceral fat accumulation, wherein the multivariate discriminant is formula 3 or formula 4.

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

According to the method of evaluating visceral fat accumulation of the present invention, amino acid concentration data on a concentration value of an amino acid in blood collected from a subject to be evaluated is measured, and a visceral fat accumulation condition in the subject is evaluated based on the measured amino acid concentration data of the subject. Thus, concentrations of amino acids in blood can be utilized to bring about an effect of enabling an accurate evaluation of a visceral fat accumulation condition.

According to the method of evaluating visceral fat accumulation of the present invention, the visceral fat accumulation condition in the subject is evaluated based on the concentration value of at least one of Val, Leu, Ile, Tyr, Phe, Trp, Glu, Ala, Pro, Orn, Lys, Gly, Ser, Met, Arg, Cys, and Gln contained in the measured amino acid concentration data of the subject. Thus, concentrations of amino acids which among amino acids in blood, are associated with a visceral fat accumulation condition can be utilized to bring about an effect of enabling an accurate evaluation of the visceral fat accumulation condition.

According to the method of evaluating visceral fat accumulation of the present invention, a discrimination between a visceral fat accumulation group and a visceral fat accumulation-free group in the subject is conducted based on the concentration value of at least one of Val, Leu, Ile, Tyr, Phe, Trp, Glu, Ala, Pro, Orn, Lys, Gly, Ser, Met, Arg, Cys, and Gln contained in the measured amino acid concentration data of the subject. Thus, concentrations of amino acids which among amino acids in blood, are useful for discriminating between 2 groups of a visceral fat accumulation group and a visceral fat accumulation-free group can be utilized to bring about an effect of enabling an accurate discrimination between the 2 groups of the visceral fat accumulation group and the visceral fat accumulation-free group.

According to the method of evaluating visceral fat accumulation of the present invention, a visceral fat area stete in the subject is evaluated based on the concentration value of at least one of Val, Leu, Ile, Tyr, Phe, Trp, Glu, Ala, Pro, Orn, Lys, Gly, Ser, Met, Arg, Cys, and Gln contained in the measured amino acid concentration data of the subject. Thus, concentrations of amino acids which among amino acids in blood, are useful for evaluating a visceral fat area state can be utilized to bring about an effect of enabling an accurate evaluation of the visceral fat area state.

According to the method of evaluating visceral fat accumulation of the present invention, a discriminant value that is a value of a multivariate discriminant with a concentration of the amino acid as an explanatory variable is calculated based on both the measured amino acid concentration data of the subject and the previously established multivariate discriminant, and the visceral fat accumulation condition in the subject is evaluated based on the calculated discriminant value. Thus, discriminant values obtained in multivariate discriminants with concentrations of amino acids as explanatory variables can be utilized to bring about an effect of enabling an accurate evaluation of a visceral fat accumulation condition.

According to the method of evaluating visceral fat accumulation of the present invention, the discriminant value is calculated based on both the concentration value of at least one of Val, Leu, Ile, Tyr, Phe, Trp, Glu, Ala, Pro, Orn, Lys, Gly, Ser, Met, Arg, Cys, and Gln contained in the measured amino acid concentration data of the subject and the multivariate discriminant containing at least one of Val, Leu, Ile, Tyr, Phe, Trp, Glu, Ala, Pro, Orn, Lys, Gly, Ser, Met, Arg, Cys, and Gln as the explanatory variable. Thus, discriminant values obtained in multivariate discriminants which are correlated with a visceral fat accumulation condition significantly can be utilized to bring about an effect of enabling an accurate evaluation of the visceral fat accumulation condition.

According to the method of evaluating visceral fat accumulation of the present invention, a discrimination between a visceral fat accumulation group and a visceral fat accumulation-free group in the subject is conducted based on the calculated discriminant value. Thus, discriminant values obtained in multivariate discriminants useful for discriminating between 2 groups of a visceral fat accumulation group and a visceral fat accumulation-free group can be utilized to bring about an effect of enabling an accurate discrimination between the 2 groups of the visceral fat accumulation group and the visceral fat accumulation-free group.

According to the method of evaluating visceral fat accumulation of the present invention, the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, discriminant values obtained in multivariate discriminants useful particularly for discriminating between 2 groups of a visceral fat accumulation group and a visceral fat accumulation-free group can be utilized to bring about an effect of enabling a more accurate discrimination between the 2 groups of the visceral fat accumulation group and the visceral fat accumulation-free group.

According to the method of evaluating visceral fat accumulation of the present invention, the multivariate discriminant is formula 1, formula 2, the logistic regression equation with Ser, Glu, Ile, Tyr, and Arg as the explanatory variables, or the logistic regression equation with Ser, Glu, Leu, and Trp as the explanatory variables. Thus, discriminant values obtained in multivariate discriminants useful particularly for discriminating between 2 groups of a visceral fat accumulation group and a visceral fat accumulation-free group can be utilized to bring about an effect of enabling a more accurate discrimination between the 2 groups of the visceral fat accumulation group and the visceral fat accumulation-free group.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

According to the method of evaluating visceral fat accumulation of the present invention, a visceral fat area stete in the subject is evaluated based on the calculated discriminant value. Thus, discriminant values obtained in multivariate discriminants useful for evaluating a visceral fat area state can be utilized to bring about an effect of enabling an accurate evaluation of the visceral fat area state.

According to the method of evaluating visceral fat accumulation of the present invention, the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, discriminant values obtained in multivariate discriminants useful particularly for evaluating a visceral fat area state can be utilized to bring about an effect of enabling a more accurate evaluation of the visceral fat area state.

According to the method of evaluating visceral fat accumulation of the present invention, the multivariate discriminant is formula 3 or formula 4. Thus, discriminant values obtained in multivariate discriminants useful particularly for evaluating a visceral fat area state can be utilized to bring about an effect of enabling a more accurate evaluation of the visceral fat area state.

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

According to the visceral fat accumulation-evaluating apparatus, the visceral fat accumulation-evaluating method, and the visceral fat accumulation-evaluating program of the present invention, a discriminant value that is a value of a multivariate discriminant with a concentration of an amino acid as an explanatory variable is calculated based on both previously obtained amino acid concentration data of the subject on a concentration value of the amino acid and the multivariate discriminant stored in a memory unit, and a visceral fat accumulation condition in the subject is evaluated based on the calculated discriminant value. Thus, discriminant values obtained in multivariate discriminants with concentrations of amino acids as explanatory variables can be utilized to bring about an effect of enabling an accurate evaluation of a visceral fat accumulation condition.

According to the visceral fat accumulation-evaluating apparatus, the visceral fat accumulation-evaluating method, and the visceral fat accumulation-evaluating program of the present invention, the discriminant value is calculated based on both the concentration value of at least one of Val, Leu, Ile, Tyr, Phe, Trp, Glu, Ala, Pro, Orn, Lys, Gly, Ser, Met, Arg, Cys, and Gln contained in the previously obtained amino acid concentration data of the subject and the multivariate discriminant containing at least one of Val, Leu, Ile, Tyr, Phe, Trp, Glu, Ala, Pro, Orn, Lys, Gly, Ser, Met, Arg, Cys, and Gln as the explanatory variable. Thus, discriminant values obtained in multivariate discriminants which are correlated with a visceral fat accumulation condition significantly can be utilized to bring about an effect of enabling an accurate evaluation of the visceral fat accumulation condition.

According to the visceral fat accumulation-evaluating apparatus, the visceral fat accumulation-evaluating method, and the visceral fat accumulation-evaluating program of the present invention, a discrimination between a visceral fat accumulation group and a visceral fat accumulation-free group in the subject is conducted based on the calculated discriminant value. Thus, discriminant values obtained in multivariate discriminants useful for discriminating between 2 groups of a visceral fat accumulation group and a visceral fat accumulation-free group can be utilized to bring about an effect of enabling an accurate discrimination between the 2 groups of the visceral fat accumulation group and the visceral fat accumulation-free group.

According to the visceral fat accumulation-evaluating apparatus, the visceral fat accumulation-evaluating method, and the visceral fat accumulation-evaluating program of the present invention, the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, discriminant values obtained in multivariate discriminants useful particularly for discriminating between 2 groups of a visceral fat accumulation group and a visceral fat accumulation-free group can be utilized to bring about an effect of enabling a more accurate discrimination between the 2 groups of the visceral fat accumulation group and the visceral fat accumulation-free group.

According to the visceral fat accumulation-evaluating apparatus, the visceral fat accumulation-evaluating method, and the visceral fat accumulation-evaluating program of the present invention, the multivariate discriminant is formula 1, formula 2, the logistic regression equation with Ser, Glu, Ile, Tyr, and Arg as the explanatory variables, or the logistic regression equation with Ser, Glu, Leu, and Trp as the explanatory variables. Thus, discriminant values obtained in multivariate discriminants useful particularly for discriminating between 2 groups of a visceral fat accumulation group and a visceral fat accumulation-free group can be utilized to bring about an effect of enabling a more accurate discrimination between the 2 groups of the visceral fat accumulation group and the visceral fat accumulation-free group.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

According to the visceral fat accumulation-evaluating apparatus, the visceral fat accumulation-evaluating method, and the visceral fat accumulation-evaluating program of the present invention, a visceral fat area stete in the subject is evaluated based on the calculated discriminant value. Thus, discriminant values obtained in multivariate discriminants useful for evaluating a visceral fat area state can be utilized to bring about an effect of enabling an accurate evaluation of the visceral fat area state.

According to the visceral fat accumulation-evaluating apparatus, the visceral fat accumulation-evaluating method, and the visceral fat accumulation-evaluating program of the present invention, the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, discriminant values obtained in multivariate discriminants useful particularly for evaluating a visceral fat area state can be utilized to bring about an effect of enabling a more accurate evaluation of the visceral fat area state.

According to the visceral fat accumulation-evaluating apparatus, the visceral fat accumulation-evaluating method, and the visceral fat accumulation-evaluating program of the present invention, the multivariate discriminant is formula 3 or formula 4. Thus, discriminant values obtained in multivariate discriminants useful particularly for evaluating a visceral fat area state can be utilized to bring about an effect of enabling a more accurate evaluation of the visceral fat area state.

$$(Glu+Gly)+(-0.2) \times (Ser/Tyr)+(-0.1) \times (His/Trp) \quad \text{(formula 3)}$$

$$(Glu/Gly)+(-0.54) \times (Ser/Leu)+(0.15) \times (Pro/Trp)+(-0.05) \times (Gln/Tyr) \quad \text{(formula 4)}$$

According to the visceral fat accumulation-evaluating apparatus, the visceral fat accumulation-evaluating method, and the visceral fat accumulation-evaluating program of the present invention, the multivariate discriminant stored in the memory unit is prepared based on visceral fat accumulation condition information stored in the memory unit containing the amino acid concentration data and visceral fat accumulation condition index data on an index for indicating the visceral fat accumulation condition. Specifically, (1) a candidate multivariate discriminant that is a candidate of the multivariate discriminant is prepared based on a predetermined discriminant-preparing method from the visceral fat accumulation condition information, (2) the prepared candidate multivariate discriminant is verified based on a predetermined verifying method, (3) the explanatory variable of the candidate multivariate discriminant is selected based on a predetermined explanatory variable-selecting method from a verification result obtained by executing (2), thereby selecting a combination of the amino acid concentration data contained in the visceral fat accumulation condition information used in preparing the candidate multivariate discriminant, and (4) the candidate multivariate discriminant used as the multivariate discriminant is selected from a plurality of the candidate multivariate discriminants based on the verification results accumulated by repeatedly executing (1), (2) and (3), thereby preparing the multivariate discriminant. Thus, there can be brought about an effect of enabling a preparation of multivariate discriminants most appropriate for evaluating a visceral fat accumulation condition (specifically, multivariate discriminants correlating significantly with the visceral fat accumulation condition (more specifically, multivariate discriminants useful for discriminating between 2 groups of a visceral fat accumulation group and a visceral fat accumulation-free group, and for evaluating a visceral fat area state)).

According to the visceral fat accumulation-evaluating system of the present invention, an information communication terminal apparatus first transmits amino acid concentration data of a subject to be evaluated to a visceral fat accumulation-evaluating apparatus. The visceral fat accumulation-evaluating apparatus receives the amino acid concentration data of the subject transmitted from the information communication terminal apparatus, calculates a discriminant value that is a value of a multivariate discriminant with a concentration of an amino acid as an explanatory variable, based on both the received amino acid concentration data of the subject and the multivariate discriminant stored in a memory unit, and evaluates a visceral fat accumulation condition in the subject based on the calculated discriminant value, and transmits an evaluation result on the visceral fat accumulation condition of the subject to the information communication terminal apparatus. Then, the information communication terminal apparatus receives the evaluation result of the subject transmitted from the visceral fat accumulation-evaluating apparatus. Thus, discriminant values obtained in multivariate discriminants with concentrations of amino acids as explanatory variables can be utilized to bring about an effect of enabling an accurate evaluation of a visceral fat accumulation condition.

According to the visceral fat accumulation-evaluating system of the present invention, the discriminant value is calculated based on both the concentration value of at least one of Val, Leu, Ile, Tyr, Phe, Trp, Glu, Ala, Pro, Orn, Lys, Gly, Ser, Met, Arg, Cys, and Gln contained in the received amino acid concentration data of the subject and the multivariate discriminant containing at least one of Val, Leu, Ile, Tyr, Phe, Trp, Glu, Ala, Pro, Orn, Lys, Gly, Ser, Met, Arg, Cys, and Gln as the explanatory variable. Thus, discriminant values obtained in multivariate discriminants which are correlated with a visceral fat accumulation condition significantly can be utilized to bring about an effect of enabling an accurate evaluation of the visceral fat accumulation condition.

According to the visceral fat accumulation-evaluating system of the present invention, a discrimination between a visceral fat accumulation group and a visceral fat accumulation-free group in the subject is conducted based on the calculated discriminant value. Thus, discriminant values obtained in multivariate discriminants useful for discriminating between 2 groups of a visceral fat accumulation group and a visceral fat accumulation-free group can be utilized to bring about an effect of enabling an accurate discrimination between the 2 groups of the visceral fat accumulation group and the visceral fat accumulation-free group.

According to the visceral fat accumulation-evaluating system of the present invention, the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, discriminant values obtained in multivariate discriminants useful particularly for discriminating between 2 groups of a visceral fat accumulation group and a visceral fat accumulation-free group can be utilized to bring about an effect of enabling a more accurate discrimination between the 2 groups of the visceral fat accumulation group and the visceral fat accumulation-free group.

According to the visceral fat accumulation-evaluating system of the present invention, the multivariate discriminant is formula 1, formula 2, the logistic regression equation with Ser, Glu, Ile, Tyr, and Arg as the explanatory variables, or the logistic regression equation with Ser, Glu, Leu, and Trp as the explanatory variables. Thus, discriminant values obtained in multivariate discriminants useful particularly for discriminating between 2 groups of a visceral fat accumulation group and a visceral fat accumulation-free group can be utilized to bring about an effect of enabling a more accurate discrimination between the 2 groups of the visceral fat accumulation group and the visceral fat accumulation-free group.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

According to the visceral fat accumulation-evaluating system of the present invention, a visceral fat area stete in the subject is evaluated based on the calculated, discriminant value. Thus, discriminant values obtained in multivariate discriminants useful for evaluating a visceral fat area state can be utilized to bring about an effect of enabling an accurate evaluation of the visceral fat area state.

According to the visceral fat accumulation-evaluating system of the present invention, the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, discriminant values obtained in multivariate discriminants useful particularly for evaluating a visceral fat area state can be utilized to bring about an effect of enabling a more accurate evaluation of the visceral fat area state.

According to the visceral fat accumulation-evaluating system of the present invention, the multivariate discriminant is formula 3 or formula 4. Thus, discriminant values obtained in multivariate discriminants useful particularly for evaluating a visceral fat area state can be utilized to bring about an effect of enabling a more accurate evaluation of the visceral fat area state.

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

According to the visceral fat accumulation-evaluating system of the present invention, the multivariate discriminant stored in the memory unit is prepared based on visceral fat accumulation condition information stored in the memory unit containing the amino acid concentration data and visceral fat accumulation condition index data on an index for indicating the visceral fat accumulation condition. Specifically, (1) a candidate multivariate discriminant that is a candidate of the multivariate discriminant is prepared based on a predetermined discriminant-preparing method from the visceral fat accumulation condition information, (2) the prepared candidate multivariate discriminant is verified based on a predetermined verifying method, (3) the explanatory variable of the candidate multivariate discriminant is selected based on a predetermined explanatory variable-selecting method from a verification result obtained by executing (2), thereby selecting a combination of the amino acid concentration data contained in the visceral fat accumulation condition information used in preparing the candidate multivariate discriminant, and (4) the candidate multivariate discriminant used as the multivariate discriminant is selected from a plurality of the candidate multivariate discriminants based on the verification results accumulated by repeatedly executing (1), (2) and (3), thereby preparing the multivariate discriminant. Thus, there can be brought about an effect of enabling a preparation of multivariate discriminants most appropriate for evaluating a visceral fat accumulation condition (specifically, multivariate discriminants correlating significantly with the visceral fat accumulation condition (more specifically, multivariate discriminants useful for discriminating between 2 groups of a visceral fat accumulation group and a visceral fat accumulation-free group, and for evaluating a visceral fat area state)).

According to the recording medium of the present invention, the visceral fat accumulation-evaluating program recorded on the recording medium is read and executed by the computer, thereby allowing the computer to execute the visceral fat accumulation-evaluating program, thus bringing about an effect of obtaining the same effect as in the visceral fat accumulation-evaluating program.

According to the method of searching for prophylactic/ameliorating substance for visceral fat accumulation of the present invention, amino acid concentration data on a concentration value of an amino acid is measured in blood collected from a subject to be evaluated to which a desired substance group has been administered, a visceral fat accumulation condition in the subject is evaluated based on the measured amino acid concentration data, and whether or not the desired substance group prevents the visceral fat accumulation or ameliorates the visceral fat accumulation condition is judged based on an evaluation result. Thus, the method of evaluating visceral fat accumulation capable of accurately evaluating a visceral fat accumulation condition by utilizing concentrations of amino acids in blood can be used to bring about an effect of enabling an accurate search for a substance for preventing a visceral fat accumulation or ameliorating a visceral fat accumulation condition. According to the method of searching for prophylactic/ameliorating substance for visceral fat accumulation of the present invention, information on amino acid concentration variation pattern typical of a visceral fat accumulation or a multivariate discriminant corresponding to a visceral fat accumulation can be used for selecting a clinically effective chemical at an early stage or an existing animal model partially reflecting a visceral fat accumulation condition.

According to the method of searching for prophylactic/ameliorating substance for visceral fat accumulation of the present invention, the visceral fat accumulation condition in the subject is evaluated based on the concentration value of at least one of Val, Leu, Ile, Tyr, Phe, Trp, Glu, Ala, Pro, Orn, Lys, Gly, Ser, Met, Arg, Cys, and Gln contained in the measured amino acid concentration data of the subject. Thus, concentrations of amino acids which among amino acids in blood, are associated with a visceral fat accumulation condition can be utilized to bring about an effect of enabling an accurate evaluation of the visceral fat accumulation condition.

According to the method of searching for prophylactic/ameliorating substance for visceral fat accumulation of the present invention, a discrimination between a visceral fat accumulation group and a visceral fat accumulation-free group in the subject is conducted based on the concentration value of at least one of Val, Leu, Ile, Tyr, Phe, Trp, Glu, Ala, Pro, Orn, Lys, Gly, Ser, Met, Arg, Cys, and Gln contained in the measured amino acid concentration data of the subject. Thus, concentrations of amino acids which among amino acids in blood, are useful for discriminating between 2 groups of a visceral fat accumulation group and a visceral fat accumulation-free group can be utilized to bring about an effect of enabling an accurate discrimination between the 2 groups of the visceral fat accumulation group and the visceral fat accumulation-free group.

According to the method of searching for prophylactic/ameliorating substance for visceral fat accumulation of the present invention, a visceral fat area stete in the subject is evaluated based on the concentration value of at least one of Val, Leu, Ile, Tyr, Phe, Trp, Glu, Ala, Pro, Orn, Lys, Gly, Ser, Met, Arg, Cys, and Gln contained in the measured amino acid concentration data of the subject. Thus, concentrations of amino acids which among amino acids in blood, are useful for evaluating a visceral fat area state can be utilized to bring about an effect of enabling an accurate evaluation of the visceral fat area state.

According to the method of searching for prophylactic/ameliorating substance for visceral fat accumulation of the present invention, a discriminant value that is a value of a multivariate discriminant with a concentration of the amino acid as an explanatory variable is calculated based on both the measured amino acid concentration data of the subject and the previously established multivariate discriminant, and the visceral fat accumulation condition in the subject is evaluated based on the calculated discriminant value. Thus, discriminant values obtained in multivariate discriminants with concentrations of amino acids as explanatory variables can be utilized to bring about an effect of enabling an accurate evaluation of a visceral fat accumulation condition.

According to the method of searching for prophylactic/ameliorating substance for visceral fat accumulation of the present invention, the discriminant value is calculated based on both the concentration value of at least one of Val, Leu, Ile, Tyr, Phe, Trp, Glu, Ala, Pro, Orn, Lys, Gly, Ser, Met, Arg, Cys, and Gln contained in the measured amino acid concentration data of the subject and the multivariate discriminant containing at least one of Val, Leu, Ile, Tyr, Phe, Trp, Glu, Ala, Pro, Orn, Lys, Gly, Ser, Met, Arg, Cys, and Gln as the explanatory variable. Thus, discriminant values obtained in multivariate discriminants which are correlated with a visceral fat accumulation condition significantly can be utilized to bring about an effect of enabling an accurate evaluation of the visceral fat accumulation condition.

According to the method of searching for prophylactic/ameliorating substance for visceral fat accumulation of the present invention, a discrimination between a visceral fat accumulation group and a visceral fat accumulation-free group in the subject is conducted based on the calculated discriminant value. Thus, discriminant values obtained in multivariate discriminants useful for discriminating between 2 groups of a visceral fat accumulation group and a visceral fat accumulation-free group can be utilized to bring about an effect of enabling an accurate discrimination between the 2 groups of the visceral fat accumulation group and the visceral fat accumulation-free group.

According to the method of searching for prophylactic/ameliorating substance for visceral fat accumulation of the present invention, the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, discriminant values obtained in multivariate discriminants useful particularly for discriminating between 2 groups of a visceral fat accumulation group and a visceral fat accumulation-free group can be utilized to bring about an effect of enabling a more accurate discrimination between the 2 groups of the visceral fat accumulation group and the visceral fat accumulation-free group.

According to the method of searching for prophylactic/ameliorating substance for visceral fat accumulation of the present invention, the multivariate discriminant is formula 1, formula 2, the logistic regression equation with Ser, Glu, Ile, Tyr, and Arg as the explanatory variables, or the logistic regression equation with Ser, Glu, Leu, and Trp as the explanatory variables. Thus, discriminant values obtained in multivariate discriminants useful particularly for discriminating between 2 groups of a visceral fat accumulation group and a visceral fat accumulation-free group can be utilized to bring about an effect of enabling a more accurate discrimination between the 2 groups of the visceral fat accumulation group and the visceral fat accumulation-free group.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

According to the method of searching for prophylactic/ameliorating substance for visceral fat accumulation of the present invention, a visceral fat area stete in the subject is evaluated based on the calculated discriminant value. Thus, discriminant values obtained in multivariate discriminants useful for evaluating a visceral fat area state can be utilized to bring about an effect of enabling an accurate evaluation of the visceral fat area state.

According to the method of searching for prophylactic/ameliorating substance for visceral fat accumulation of the present invention, the multivariate discriminant is expressed by one fractional expression or the sum of a plurality of the fractional expressions and contains at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, discriminant values obtained in multivariate discriminants useful particularly for evaluating a visceral fat area state can be utilized to bring about an effect of enabling a more accurate evaluation of the visceral fat area state.

According to the method of searching for prophylactic/ameliorating substance for visceral fat accumulation of the present invention, the multivariate discriminant is formula 3 or formula 4. Thus, discriminant values obtained in multivariate discriminants useful particularly for evaluating a visceral fat area state can be utilized to bring about an effect of enabling a more accurate evaluation of the visceral fat area state.

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

When the visceral fat accumulation condition is evaluated (specifically, the discrimination between the visceral fat accumulation group and the visceral fat accumulation-free group is conducted, the visceral fat area is evaluated) in the present invention, concentrations of other metabolites (biological metabolites), protein expression level, age and sex of the subject, biological indices or the like may be used in addition to the concentrations of the amino acids. When the visceral fat accumulation condition is evaluated (specifically, the discrimination between the visceral fat accumulation group and the visceral fat accumulation-free group is conducted, the visceral fat area is evaluated) in the present invention, concentrations of other metabolites (biological metabolites), protein expression level, age and sex of the subject, biological indices or the like may be used as the explanatory variables in the multivariate discriminants in addition to the concentrations of the amino acids.

The visceral fat accumulation includes symptoms of hyperglycemia, hypertension and hyperlipidemia based on insulin resistance, and thus the present invention is also effective in evaluation or discrimination thereof.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a chart showing an example of information stored in a user information file 106a;

FIG. 8 is a chart showing an example of information stored in an amino acid concentration data file 106b;

FIG. 9 is a chart showing an example of information stored in a visceral fat accumulation condition information file 106c;

FIG. 10 is a chart showing an example of information stored in a designated visceral fat accumulation condition information file 106d;

FIG. 11 is a chart showing an example of information stored in a candidate multivariate discriminant file 106e1;

FIG. 12 is a chart showing an example of information stored in a verification result file 106e2;

FIG. 13 is a chart showing an example of information stored in a selected visceral fat accumulation condition information file 106e3;

FIG. 14 is a chart showing an example of information stored in a multivariate discriminant file 106e4;

FIG. 15 is a chart showing an example of information stored in a discriminant value file 106f;

FIG. 28 is a chart showing a list of an AUC of an ROC curve for an evaluation of a discriminatory performance between 2 groups;

FIG. 29 is a chart showing a sensitivity, specificity, positive predictive value, negative predictive value and discrimination rate for cutoff value in a discrimination between 2 groups;

FIG. 33 is a chart showing a list of an AUC of an ROC curve for an evaluation of a discriminatory performance between 2 groups;

FIG. 34 is a chart showing a list of an AUC of an ROC curve for an evaluation of a discriminatory performance between 2 groups;

FIG. 35 is a chart showing a list of an AUC of an ROC curve for an evaluation of a discriminatory performance between 2 groups;

FIG. 36 is a chart showing a sensitivity, specificity, positive predictive value, negative predictive value and discrimination rate for cutoff value in a discrimination between 2 groups;

FIG. 37 is a chart showing a list of index formulae having a same diagnostic performance as that of an index formula 5;

FIG. 38 is a chart showing a list of index formulae having a same diagnostic performance as that of the index formula 5;

FIG. 39 is a chart showing a list of index formulae having a same diagnostic performance as that of the index formula 5;

FIG. 40 is a chart showing a list of index formulae having a same diagnostic performance as that of the index formula 5;

FIG. 41 is a chart showing a list of index formulae having a same discriminatory performance as that of an index formula 4;

FIG. 42 is a chart showing a list of index formulae having a same discriminatory performance as that of the index formula 4;

FIG. 43 is a chart showing a list of index formulae having a same discriminatory performance as that of an index formula 6;

FIG. 44 is a chart showing a list of index formulae having a same discriminatory performance as that of the index formula 6;

FIG. 45 is a chart showing a list of index formulae having a same discriminatory performance as that of the index formula 6;

FIG. 46 is a chart showing a list of index formulae having a same discriminatory performance as that of the index formula 6; and FIG. 47 is a chart showing a list of index formulae having a same diagnostic performance as that of the index formula 5.

DETAILED DESCRIPTION OF THE PREFERRED EMBODIMENTS

Hereinafter, an embodiment (first embodiment) of the method of evaluating visceral fat accumulation of the present invention, an embodiment (second embodiment) of the visceral fat accumulation-evaluating apparatus, the visceral fat accumulation-evaluating method, the visceral fat accumulation-evaluating system, the visceral fat accumulation-evaluating program and the recording medium of the present invention, and an embodiment (third embodiment) of the method of searching for prophylactic/ameliorating substance for visceral fat accumulation of the present invention are described in detail with reference to the drawings. The present invention is not limited to these embodiments.

First Embodiment 1-1. Outline of the Invention

Figure 1:
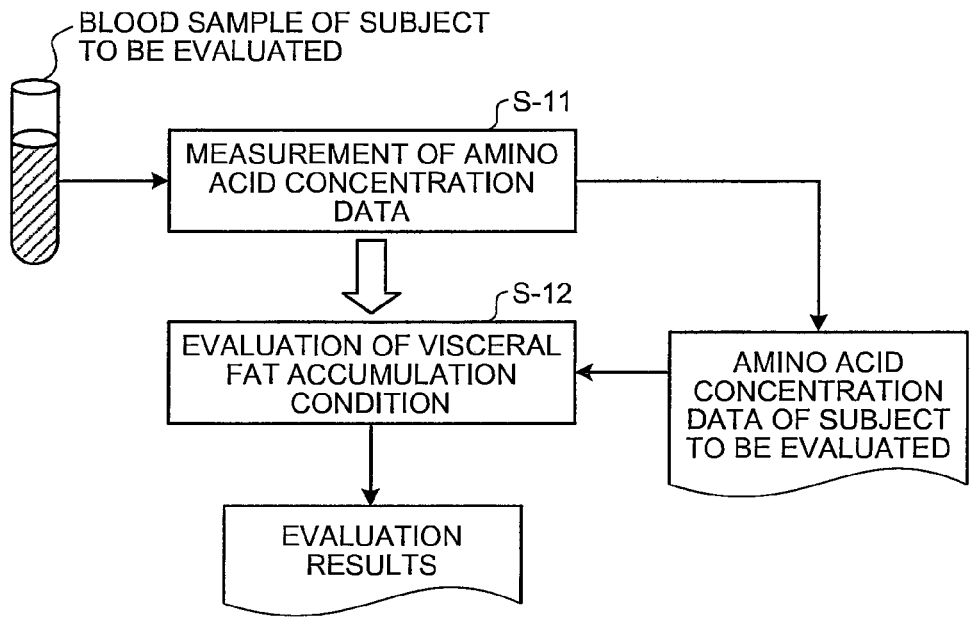
FIG. 1 is a principle configurational diagram showing a basic principle of the present invention.

Here, an outline of the method of evaluating visceral fat accumulation of the present invention will be described with reference to FIG. 1. FIG. 1 is a principle configurational diagram showing a basic principle of the present invention.

In the present invention, amino acid concentration data on a concentration value of an amino acid in blood collected from a subject (for example, an individual such as animal or human) to be evaluated are first measured (step S-11). Concentrations of amino acids in blood are analyzed in the following manner. A blood sample is collected in a heparin-treated tube, and then the blood plasma is separated by centrifugation of the collected blood sample. All blood plasma samples separated are frozen and stored at −70° C. before a measurement of amino acid concentrations. Before the measurement of amino acid concentrations, the blood plasma samples are deproteinized by adding sulfosalicylic acid to a concentration of 3%. An amino acid analyzer by high-performance liquid chromatography (HPLC) by using ninhydrin reaction in post column is used for the measurement of amino acid concentrations. The unit of the amino acid concentration may be for example molar concentration, weight concentration, or these concentrations which are subjected to addition, subtraction, multiplication and division by an arbitrary constant.

In the present invention, a visceral fat accumulation condition in the subject is evaluated based on the amino acid concentration data of the subject measured in the step S-11 (step S-12).

According to the present invention described above, the amino acid concentration data on the concentration value of the amino acid in blood collected from the subject is measured, and the visceral fat accumulation condition in the subject is evaluated based on the measured amino acid concentration data of the subject. Thus, the concentrations of the amino acids in blood can be utilized to bring about an effect of enabling an accurate evaluation of the visceral fat accumulation condition.

Before the step S-12 is executed, data such as defective and outliers may be removed from the amino acid concentration data of the subject measured in the step S-11. Thus, the visceral fat accumulation condition can be more accurately evaluated.

In the step S-12, the visceral fat accumulation condition in the subject may be evaluated based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured in the step S-11. Thus, the concentrations of the amino acids which among amino acids in blood, are associated with the visceral fat accumulation condition can be utilized to bring about an effect of enabling an accurate evaluation of the visceral fat accumulation condition.

In the step S-12, a discrimination between a visceral fat accumulation group and a visceral fat accumulation-free group in the subject may be conducted based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured in the step S-11. Specifically, the concentration value of at least one of Val, Leu, Ile, Tyr, Phe, Trp, Glu, Ala, Pro, Orn, Lys, Gly, Ser, Met, Arg, Cys, and Gln may be compared with a previously established threshold (cutoff value), thereby discriminating between the visceral fat accumulation group and the visceral fat accumulation-free group in the subject. Thus, the concentrations of the amino acids which among amino acids in blood, are useful for discriminating between 2 groups of the visceral fat accumulation group and the visceral fat accumulation-free group can be utilized to bring about an effect of enabling an accurate discrimination between the 2 groups of the visceral fat accumulation group and the visceral fat accumulation-free group.

In the step S-12, a visceral fat area stete in the subject that reflects the visceral fat accumulation may be evaluated based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured in the step S-11. Specifically, the concentration value of at least one of Val, Leu, Ile, Tyr, Phe, Trp, Glu, Ala, Pro, Orn, Lys, Gly, Ser, Met, Arg, Cys, and Gln may be compared with a previously established threshold (cutoff value), thereby evaluating the visceral fat area state in the subject that reflects the visceral fat accumulation. Thus, the concentrations of the amino acids which among amino acids in blood, are useful for evaluating the visceral fat area state can be utilized to bring about an effect of enabling an accurate evaluation of the visceral fat area state.

In the step S-12, a discriminant value that is a value of a multivariate discriminant with a concentration of the amino acid as an explanatory variable may be calculated based on both the amino acid concentration data of the subject measured in the step S-11 and the previously established multivariate discriminant, and the visceral fat accumulation condition in the subject may be evaluated based on the calculated discriminant value. Thus, the discriminant values obtained in the multivariate discriminants with the concentrations of the amino acids as the explanatory variables can be utilized to bring about an effect of enabling an accurate evaluation of the visceral fat accumulation condition.

In the step S-12, the discriminant value may be calculated based on both the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured in the step S-11 and the multivariate discriminant containing at least one of Val, Leu, Ile, Tyr, Phe, Trp, Glu, Ala, Pro, Orn, Lys, Gly, Ser, Met, Arg, Cys, and Gln as the explanatory variable, and the visceral fat accumulation condition in the subject may be evaluated based on the calculated discriminant value. Thus, the discriminant values obtained in the multivariate discriminants which are correlated with the visceral fat accumulation condition significantly can be utilized to bring about an effect of enabling an accurate evaluation of the visceral fat accumulation condition.

In the step S-12, the discrimination between the visceral fat accumulation group and the visceral fat accumulation-free group in the subject may be conducted based on the calculated discriminant value. Specifically, the discriminant value may be compared with a previously established threshold (cutoff value), thereby discriminating between the visceral fat accumulation group and the visceral fat accumulation-free group in the subject. Thus, the discriminant values obtained in the multivariate discriminants useful for discriminating between 2 groups of the visceral fat accumulation group and the visceral fat accumulation-free group can be utilized to bring about an effect of enabling an accurate discrimination between the 2 groups of the visceral fat accumulation group and the visceral fat accumulation-free group. The multivariate discriminant may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be formula 1, formula 2, the logistic regression equation with Ser, Glu, Ile, Tyr, and Arg as the explanatory variables, or the logistic regression equation with Ser, Glu, Leu, and Trp as the explanatory variables. Thus, the discriminant values obtained in the multivariate discriminants useful particularly for discriminating between the 2 groups of the visceral fat accumulation group and the visceral fat accumulation-free group can be utilized to bring about an effect of enabling a more accurate discrimination between the 2 groups of the visceral fat accumulation group and the visceral fat accumulation-free group.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

In the step S-12, the visceral fat area state in the subject that reflects the visceral fat accumulation may be evaluated based on the calculated discriminant value. Specifically, the discriminant value may be compared with a previously established threshold (cutoff value), thereby evaluating the visceral fat area state in the subject that reflects the visceral fat accumulation. Thus, the discriminant values obtained in the multivariate discriminants useful for evaluating the visceral fat area state can be utilized to bring about an effect of enabling an accurate evaluation of the visceral fat area state. The multivariate discriminant may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be formula 3 or formula 4. Thus, the discriminant values obtained in the multivariate discriminants useful particularly for evaluating the visceral fat area state can be utilized to bring about an effect of enabling a more accurate evaluation of the visceral fat area state.

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

The multivariate discriminants described above can be prepared by a method described in International Publication WO 2004/052191 that is an international application filed by the present applicant or by a method (multivariate discriminant-preparing processing described in the second embodiment described later) described in International Publication WO 2006/098192 that is an international application filed by the present applicant. Any multivariate discriminants obtained by these methods can be preferably used in the evaluation of the visceral fat accumulation condition, regardless of the unit of the amino acid concentration in the amino acid concentration data as input data.

In the fractional expression, the numerator of the fractional expression is expressed by the sum of the amino acids A, B, C etc. and the denominator of the fractional expression is expressed by the sum of the amino acids a, b, c etc. The fractional expression also includes the sum of the fractional expressions α, β, γ etc. (for example, α+β) having such constitution. The fractional expression also includes divided fractional expressions. The amino acids used in the numerator or denominator may have suitable coefficients respectively. The amino acids used in the numerator or denominator may appear repeatedly. Each fractional expression may have a suitable coefficient. A value of a coefficient for each explanatory variable and a value for a constant term may be any real numbers.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each explanatory variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

When the visceral fat accumulation condition is evaluated (specifically, the discrimination between the visceral fat accumulation group and the visceral fat accumulation-free group is conducted, the visceral fat area state is evaluated) in the present invention, concentrations of other metabolites (biological metabolites), protein expression level, age and sex of the subject, biological indices or the like may be used in addition to the concentrations of the amino acids. When the visceral fat accumulation condition is evaluated (specifically, the discrimination between the visceral fat accumulation group and the visceral fat accumulation-free group is conducted, the visceral fat area state is evaluated) in the present invention, concentrations of other metabolites (biological metabolites), protein expression level, age and sex of the subject, biological indices or the like may be used as the explanatory variables in the multivariate discriminants in addition to the concentrations of the amino acids.

Figure 2:
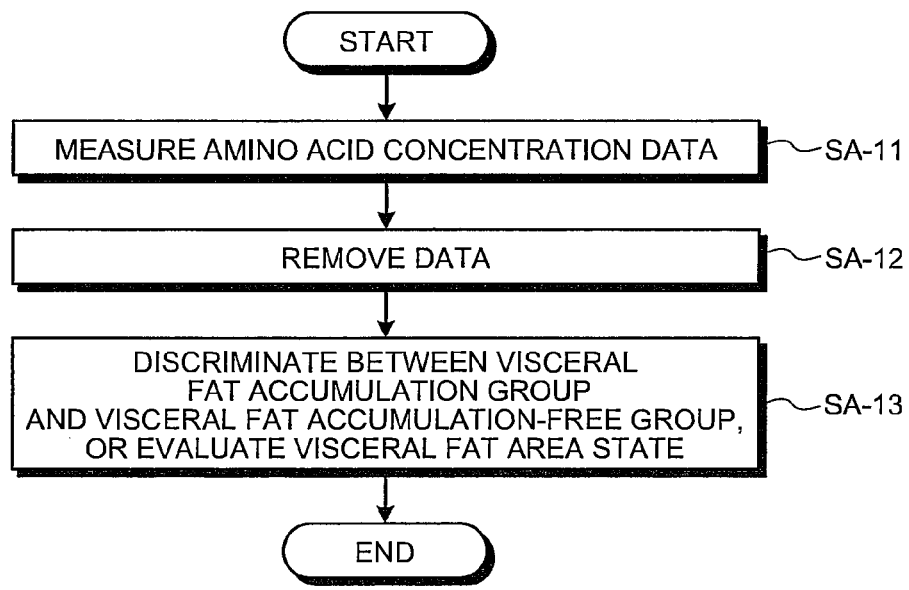
FIG. 2 is a flowchart showing one example of a method of evaluating visceral fat accumulation according to a first embodiment.

1-2. Method of Evaluating Visceral Fat Accumulation in Accordance with the First Embodiment Herein, the method of evaluating visceral fat accumulation according to the first embodiment is described with reference to FIG. 2. FIG. 2 is a flowchart showing one example of the method of evaluating visceral fat accumulation according to the first embodiment.

The amino acid concentration data on the concentration values of the amino acids is measured from blood collected from an individual such as animal or human (step SA-11). The measurement of the concentration values of the amino acids is conducted by the method described above.

Data such as defective and outliers is then removed from the amino acid concentration data of the individual measured in the step SA-11 (step SA-12).

Then, the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the individual from which the defective and outliers have been removed in the step SA-12 is compared with a previously established threshold (cutoff value), thereby discriminating between the visceral fat accumulation group and the visceral fat accumulation-free group in the individual or evaluating the visceral fat area state in the individual (step SA-13).

1-3. Summary of the First Embodiment and Other Embodiments

In the method of evaluating visceral fat accumulation as described above in detail, (1) the amino acid concentration data is measured from blood collected from the individual, (2) the data such as the defective and the outliers is removed from the measured amino acid concentration data of the individual, and (3) the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the individual from which the defective and the outliers have been removed is compared with the previously established threshold (cutoff value), thereby discriminating between the visceral fat accumulation group and the visceral fat accumulation-free group in the individual or evaluating the visceral fat area state in the individual. Thus, the concentrations of the amino acids which among amino acids in blood, are useful for discriminating between the 2 groups of the visceral fat accumulation group and the visceral fat accumulation-free group or for evaluating the visceral fat area state can be utilized to bring about an effect of enabling an accurate discrimination between the 2 groups of the visceral fat accumulation group and the visceral fat accumulation-free group or an accurate evaluation of the visceral fat area state.

In the step SA-13, (a) the discriminant value may be calculated based on both (i) the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the individual from which the defective and the outliers have been removed in the step SA-12 and (ii) the multivariate discriminant containing at least one of Val, Leu, Ile, Tyr, Phe, Trp, Glu, Ala, Pro, Orn, Lys, Gly, Ser, Met, Arg, Cys, and Gln as the explanatory variable, and (b) the calculated discriminant value may be compared with the previously established threshold (cutoff value), thereby discriminating between the visceral fat accumulation group and the visceral fat accumulation-free group in the individual or evaluating the visceral fat area state in the individual. Thus, the discriminant values obtained in the multivariate discriminants useful for discriminating between the 2 groups of the visceral fat accumulation group and the visceral fat accumulation-free group or evaluating the visceral fat area state can be utilized to bring about an effect of enabling an accurate discrimination between the 2 groups of the visceral fat accumulation group and the visceral fat accumulation-free group or an accurate evaluation of the visceral fat area state.

In the step SA-13, the multivariate discriminant may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Specifically, the multivariate discriminant may be formula 1, formula 2, the logistic regression equation with Ser, Glu, Ile, Tyr, and Arg as the explanatory variables, or the logistic regression equation with Ser, Glu, Leu, and Trp as the explanatory variables. Thus, the discriminant values obtained in the multivariate discriminants useful particularly for discriminating between the 2 groups of the visceral fat accumulation group and the visceral fat accumulation-free group can be utilized to bring about an effect of enabling a more accurate discrimination between the 2 groups of the visceral fat accumulation group and the visceral fat accumulation-free group.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

Specifically, the multivariate discriminant may be formula 3 or formula 4. Thus, the discriminant values obtained in the multivariate discriminants useful particularly for evaluating the visceral fat area state can be utilized to bring about an effect of enabling a more accurate evaluation of the visceral fat area state.

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

The multivariate discriminants described above can be prepared by a method described in International Publication WO 2004/052191 that is an international application filed by the present applicant or by a method (multivariate discriminant-preparing processing described in the second embodiment described later) described in International Publication WO 2006/098192 that is an international application filed by the present applicant. Any multivariate discriminants obtained by these methods can be preferably used in the evaluation of the visceral fat accumulation condition, regardless of the unit of the amino acid concentration in the amino acid concentration data as input data.

Second Embodiment 2-1. Outline of the Invention

Figure 3:
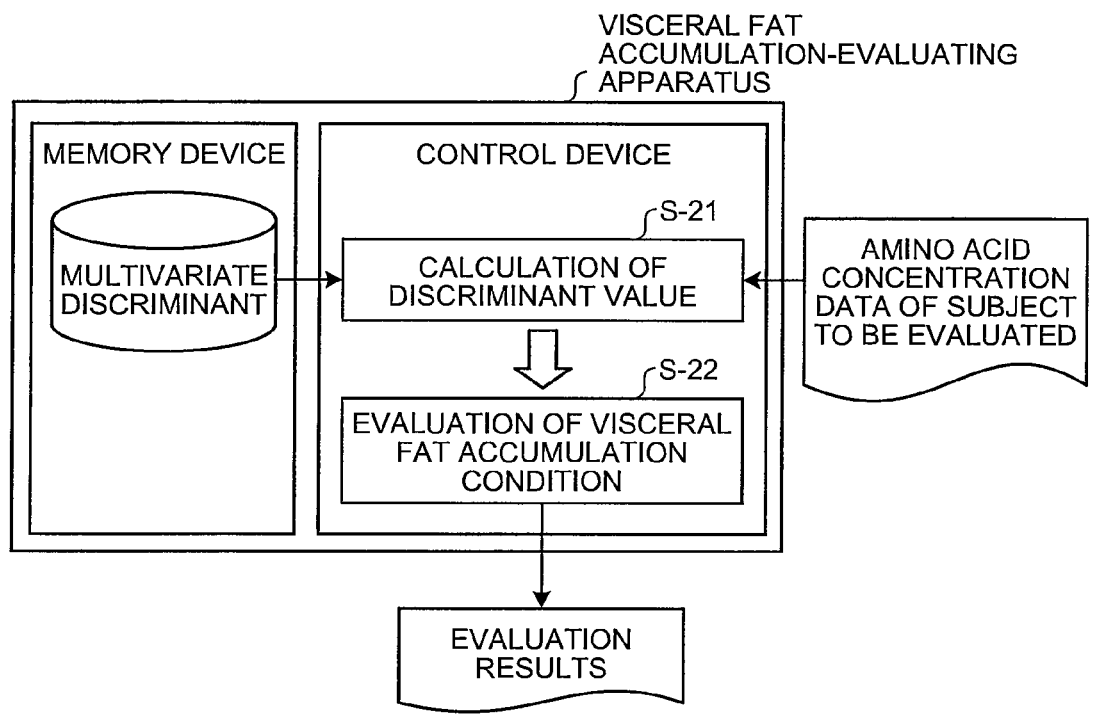
FIG. 3 is a principle configurational diagram showing a basic principle of the present invention.

Herein, an outline of the visceral fat accumulation-evaluating apparatus, the visceral fat accumulation-evaluating method, the visceral fat accumulation-evaluating system, the visceral fat accumulation-evaluating program and the recording medium of the present invention are described in detail with reference to FIG. 3. FIG. 3 is a principle configurational diagram showing a basic principle of the present invention.

In the present invention, a discriminant value that is a value of a multivalent discriminant with a concentration of an amino acid as an explanatory variable is calculated in a control device based on both previously obtained amino acid concentration data of a subject to be evaluated (for example, an individual such as animal or human) and the multivariate discriminant stored in a memory device (step S-21).

In the present invention, a visceral fat accumulation condition in the subject is evaluated in the control device based on the discriminant value calculated in the step S-21 (step S-22).

According to the present invention described above, the discriminant value is calculated based on both the previously obtained amino acid concentration data of the subject on the concentration value of the amino acid and the multivariate discriminant with the concentration of the amino acid as the explanatory variable stored in the memory device, and the visceral fat accumulation condition in the subject is evaluated based on the calculated discriminant value. Thus, the discriminant values obtained in the multivariate discriminants with the concentrations of the amino acids as the explanatory variables can be utilized to bring about an effect of enabling an accurate evaluation of the visceral fat accumulation condition.

In the step S-21, the discriminant value may be calculated based on both the concentration value of at least one of Val, Leu, Ile, Tyr, Phe, Trp, Glu, Ala, Pro, Orn, Lys, Gly, Ser, Met, Arg, Cys, and Gln contained in the previously obtained amino acid concentration data of the subject and the multivariate discriminant containing at least one of Val, Leu, Ile, Tyr, Phe, Trp, Glu, Ala, Pro, Orn, Lys, Gly, Ser, Met, Arg, Cys, and Gln as the explanatory variable. Thus, the discriminant values obtained in the multivariate discriminants which are correlated with the visceral fat accumulation condition significantly can be utilized to bring about an effect of enabling an accurate evaluation of the visceral fat accumulation condition.

In the step S-22, a discrimination between a visceral fat accumulation group and a visceral fat accumulation-free group in the subject may be conducted based on the discriminant value calculated in the step S-21. Specifically, the discriminant value may be compared with a previously established threshold (cutoff value), thereby discriminating between the visceral fat accumulation group and the visceral fat accumulation-free group in the subject. Thus, the discriminant values obtained in the multivariate discriminants useful for discriminating between the 2 groups of the visceral fat accumulation group and the visceral fat accumulation-free group can be utilized to bring about an effect of enabling an accurate discrimination between the 2 groups of the visceral fat accumulation group and the visceral fat accumulation-free group. The multivariate discriminant may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be formula 1, formula 2, the logistic regression equation with Ser, Glu, Ile, Tyr, and Arg as the explanatory variables, or the logistic regression equation with Ser, Glu, Leu, and Trp as the explanatory variables. Thus, the discriminant values obtained in the multivariate discriminants useful particularly for discriminating between the 2 groups of the visceral fat accumulation group and the visceral fat accumulation-free group can be utilized to bring about an effect of enabling a more accurate discrimination between the 2 groups of the visceral fat accumulation group and the visceral fat accumulation-free group.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

In the step S-22, a visceral fat area stete in the subject that reflects the visceral fat accumulation is evaluated based on the discriminant value calculated in the step S-21. Specifically, the discriminant value may be compared with a previously established threshold (cutoff value), thereby evaluating the visceral fat area state in the subject that reflects the visceral fat accumulation. Thus, the discriminant values obtained in the multivariate discriminants useful for evaluating the visceral fat area state can be utilized to bring about an effect of enabling an accurate evaluation of the visceral fat area state. The multivariate discriminant may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. The multivariate discriminant may be formula 3 or formula 4. Thus, the discriminant values obtained in the multivariate discriminants useful particularly for evaluating the visceral fat area state can be utilized to bring about an effect of enabling a more accurate evaluation of the visceral fat area state.

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

The multivariate discriminants described above can be prepared by a method described in International Publication WO 2004/052191 that is an international application filed by the present applicant or by a method (multivariate discriminant-preparing processing described later) described in International Publication WO 2006/098192 that is an international application filed by the present applicant. Any multivariate discriminants obtained by these methods can be preferably used in the evaluation of the visceral fat accumulation condition, regardless of the unit of the amino acid concentration in the amino acid concentration data as input data.

In the fractional expression, the numerator of the fractional expression is expressed by the sum of the amino acids A, B, C etc. and the denominator of the fractional expression is expressed by the sum of the amino acids a, b, c etc. The fractional expression also includes the sum of the fractional expressions α, β, γ etc. (for example, α+β) having such constitution. The fractional expression also includes divided fractional expressions. The amino acids used in the numerator or denominator may have suitable coefficients respectively. The amino acids used in the numerator or denominator may appear repeatedly. Each fractional expression may have a suitable coefficient. A value of a coefficient for each explanatory variable and a value for a constant term may be any real numbers.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by sum of different forms of the multivariate discriminants. In the multiple regression equation, multiple logistic regression equation and canonical discriminant function, a coefficient and constant term are added to each explanatory variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

When the visceral fat accumulation condition is evaluated (specifically, the discrimination between the visceral fat accumulation group and the visceral fat accumulation-free group is conducted, the visceral fat area state is evaluated) in the present invention, concentrations of other metabolites (biological metabolites), protein expression level, age and sex of the subject, biological indices or the like may be used in addition to the concentrations of the amino acids. When the visceral fat accumulation condition is evaluated (specifically, the discrimination between the visceral fat accumulation group and the visceral fat accumulation-free group is conducted, the visceral fat area state is evaluated) in the present invention, concentrations of other metabolites (biological metabolites), protein expression level, age and sex of the subject, biological indices or the like may be used as the explanatory variables in the multivariate discriminants in addition to the concentrations of the amino acids.

Here, the summary of the multivariate discriminant-preparing processing (steps 1 to 4) is described in detail.

First, a candidate multivariate discriminant (e.g., $y=a1\times1+a2\times2+\ldots+an\times n$, y: visceral fat accumulation condition index data, xi: amino acid concentration data, ai: constant, i=1, 2, . . . , n) that is a candidate of the multivariate discriminant is prepared in the control device based on a predetermined discriminant-preparing method from visceral fat accumulation condition information stored in the memory device containing the amino acid concentration data and visceral fat accumulation condition index data on an index for indicating the visceral fat accumulation condition (step 1). Data containing defective and outliers may be removed in advance from the visceral fat accumulation condition information.

In the step 1, a plurality of the candidate multivariate discriminants may be prepared from the visceral fat accumulation condition information by using a plurality of the different discriminant-preparing methods (including those for multivariate analysis such as principal component analysis, discriminant analysis, support vector machine, multiple regression analysis, logistic regression analysis, k-means method, cluster analysis, and decision tree). Specifically, a plurality of the candidate multivariate discriminant groups may be prepared simultaneously and concurrently by using a plurality of different algorithms with the visceral fat accumulation condition information which is multivariate data composed of the amino acid concentration data and the visceral fat accumulation condition index data obtained by analyzing blood samples from a large number of healthy subjects and visceral fat accumulation groups. For example, the two different candidate multivariate discriminants may be formed by performing discriminant analysis and logistic regression analysis simultaneously with the different algorithms. Alternatively, the candidate multivariate discriminant may be formed by converting the visceral fat accumulation condition information with the candidate multivariate discriminant prepared by performing principal component analysis and then performing discriminant analysis of the converted visceral fat accumulation condition information. In this way, it is possible to finally prepare the multivariate discriminant suitable for diagnostic condition.

The candidate multivariate discriminant prepared by principal component analysis is a linear expression consisting of amino acid explanatory variables maximizing the variance of all amino acid concentration data. The candidate multivariate discriminant prepared by discriminant analysis is a high-powered expression (including exponential and logarithmic expressions) consisting of amino acid explanatory variables minimizing the ratio of the sum of the variances in respective groups to the variance of all amino acid concentration data. The candidate multivariate discriminant prepared by using support vector machine is a high-powered expression (including kernel function) consisting of amino acid explanatory variables maximizing the boundary between groups. The candidate multivariate discriminant prepared by multiple regression analysis is a high-powered expression consisting of amino acid explanatory variables minimizing the sum of the distances from all amino acid concentration data. The candidate multivariate discriminant prepared by logistic regression analysis is a fraction expression having, as a component, the natural logarithm having a linear expression consisting of amino acid explanatory variables maximizing the likelihood as the exponent. The k-means method is a method of searching k pieces of neighboring amino acid concentration data in various groups, designating the group containing the greatest number of the neighboring points as its data-belonging group, and selecting the amino acid explanatory variable that makes the group to which input amino acid concentration data belong agree well with the designated group. The cluster analysis is a method of clustering (grouping) the points closest in entire amino acid concentration data. The decision tree is a method of ordering amino acid explanatory variables and predicting the group of amino acid concentration data from the pattern possibly held by the higher-ordered amino acid explanatory variable.

Returning to the description of the multivariate discriminant-preparing processing, the candidate multivariate discriminant prepared in the step 1 is verified (mutually verified) in the control device based on a predetermined verifying method (step 2). The verification of the candidate multivariate discriminant is performed on each other to each candidate multivariate discriminant prepared in the step 1.

In the step 2, at least one of discrimination rate, sensitivity, specificity, information criterion, and the like of the candidate multivariate discriminant may be verified by at least one of the bootstrap method, holdout method, leave-one-out method, and the like. In this way, it is possible to prepare the candidate multivariate discriminant higher in predictability or reliability, by taking the visceral fat accumulation condition information and the diagnostic condition into consideration.

The discrimination rate is the rate of the visceral fat accumulation conditions judged correct according to the present invention in all input data. The sensitivity is the rate of the visceral fat accumulation conditions judged correct according to the present invention in the visceral fat accumulation conditions declared overabundance in the input data. The specificity is the rate of the visceral fat accumulation conditions judged correct according to the present invention in the visceral fat accumulation conditions described healthy in the input data. The information criterion is the sum of the number of the amino acid explanatory variables in the candidate multivariate discriminant prepared in the step 1 and the difference in number between the visceral fat accumulation conditions evaluated according to the present invention and those declared in input data. The predictability is the average of the discrimination rate, sensitivity, or specificity obtained by repeating verification of the candidate multivariate discriminant. Alternatively, the reliability is the variance of the discrimination rate, sensitivity, or specificity obtained by repeating verification of the candidate multivariate discriminant.

Returning to the description of the multivariate discriminant-preparing processing, a combination of the amino acid concentration data contained in the visceral fat accumulation condition information used in preparing the candidate multivariate discriminant is selected by selecting the explanatory variable of the candidate multivariate discriminant in the control device based on a predetermined explanatory variable-selecting method from the verification result obtained in the step 2 (step 3). The selection of the amino acid explanatory variable is performed on each candidate multivariate discriminant prepared in the step 1. In this way, it is possible to select the amino acid explanatory variable of the candidate multivariate discriminant properly. The step 1 is executed once again by using the visceral fat accumulation condition information including the amino acid concentration data selected in the step 3.

In the step 3, the amino acid explanatory variable of the candidate multivariate discriminant may be selected based on at least one of the stepwise method, best path method, local search method, and genetic algorithm from the verification result obtained in the step 2.

The best path method is a method of selecting an amino acid explanatory variable by optimizing an evaluation index of the candidate multivariate discriminant while eliminating the amino acid explanatory variables contained in the candidate multivariate discriminant one by one.

Returning to the description of the multivariate discriminant-preparing processing, the steps 1, 2 and 3 are repeatedly performed in the control device, and based on verification results thus accumulated, the candidate multivariate discriminant used as the multivariate discriminant is selected from a plurality of the candidate multivariate discriminants, thereby preparing the multivariate discriminant (step 4). In the selection of the candidate multivariate discriminants, there are cases where the optimum multivariate discriminant is selected from the candidate multivariate discriminants prepared in the same discriminant-preparing method or the optimum multivariate discriminant is selected from all candidate multivariate discriminants.

As described above, in the multivariate discriminant-preparing processing, the processing for the preparation of the candidate multivariate discriminants, the verification of the candidate multivariate discriminants, and the selection of the explanatory variables in the candidate multivariate discriminants are performed based on the visceral fat accumulation condition information in a series of operations in a systematized manner, whereby the optimum multivariate discriminant for the evaluation of the visceral fat accumulation condition can be prepared. In other words, in the multivariate discriminant-preparing processing, the amino acid concentration is used in multivariate statistical analysis, and for selecting the optimum and robust combination of the explanatory variables, the explanatory variable-selecting method is combined with cross-validation to extract the multivariate discriminant having high diagnosis performance. Logistic regression equation, linear discriminant, discriminant prepared by support vector machine, discriminant prepared by Mahalanobis' generalized distance method, equation prepared by multiple regression analysis, discriminant prepared by cluster analysis, and the like can be used in the multivariate discriminant.

2-2. System Configuration

Hereinafter, a configuration of the visceral fat accumulation-evaluating system according to the second embodiment (hereinafter referred to sometimes as the present system) will be described with reference to FIGS. 4 to 20. This system is merely one example, and the present invention is not limited thereto.

Figure 4:
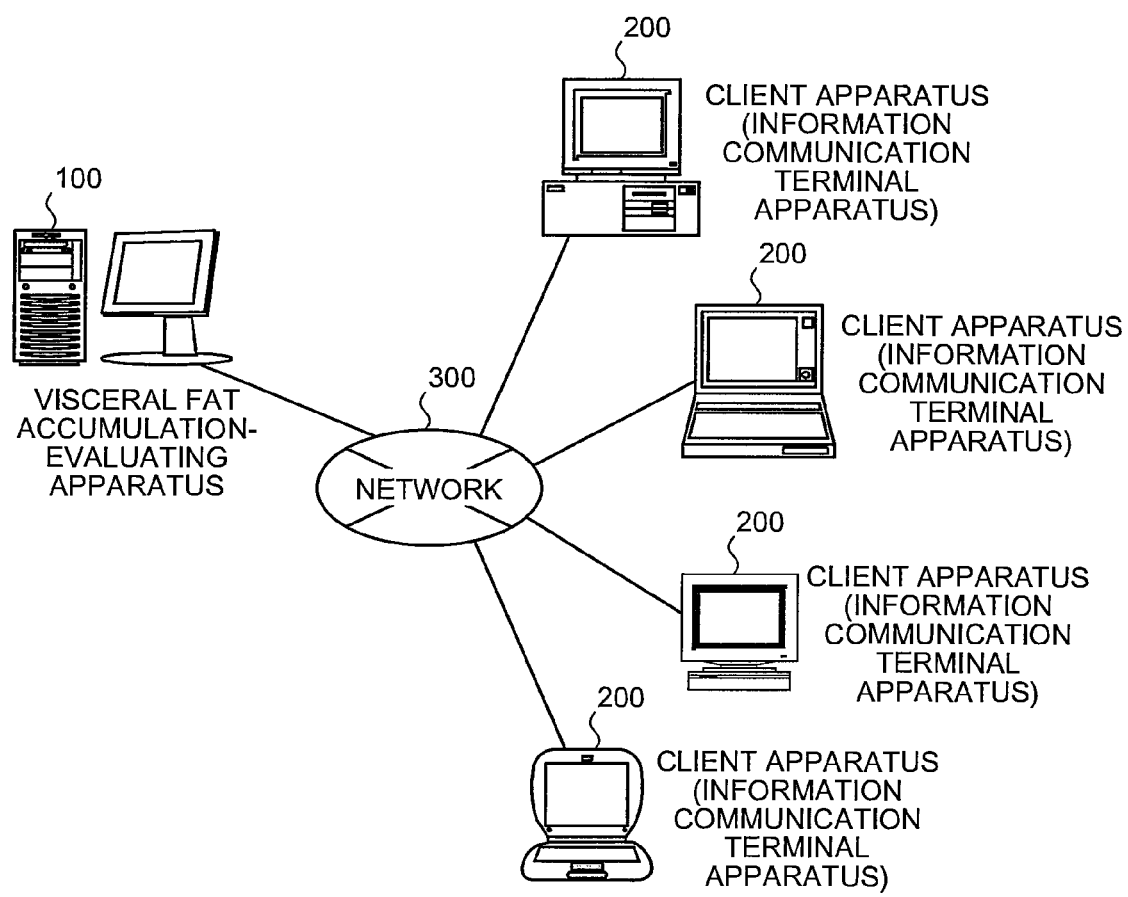
FIG. 4 is a diagram showing an example of an entire configuration of a present system.
Figure 5:
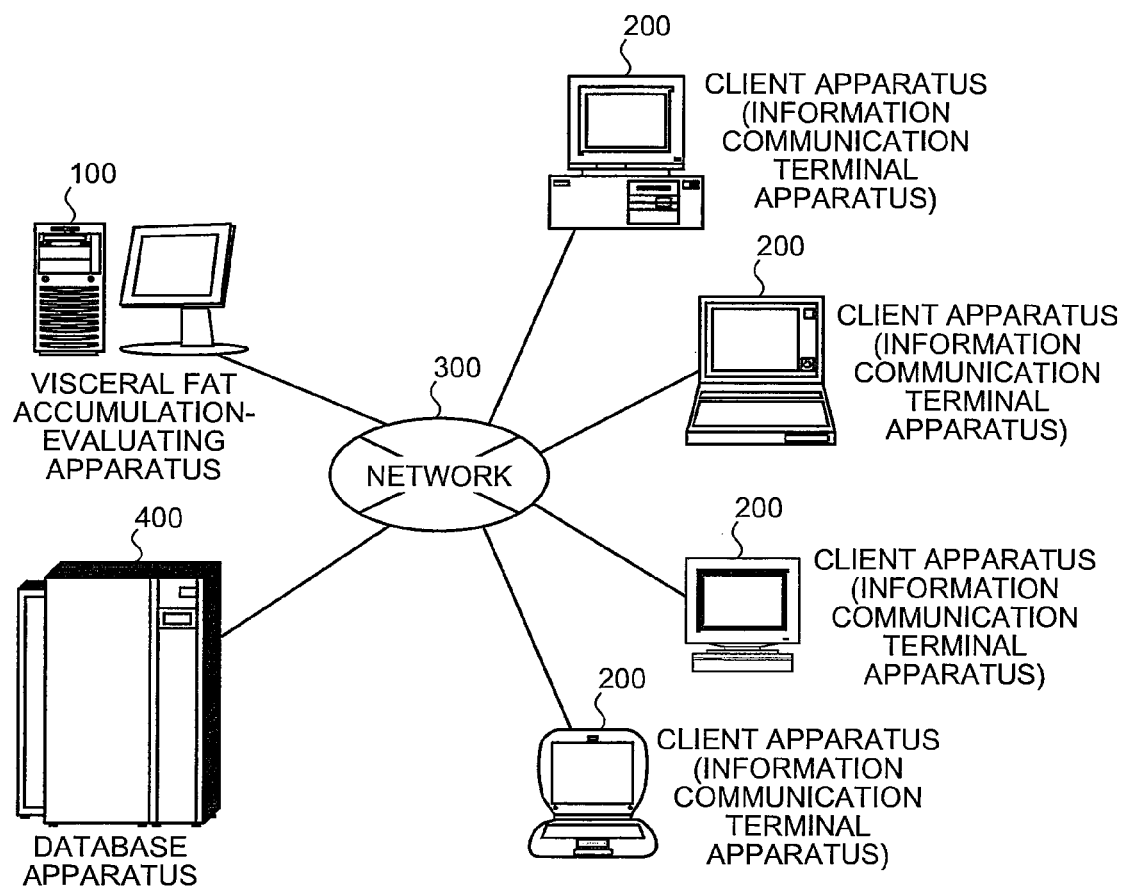
FIG. 5 is a diagram showing another example of an entire configuration of the present system.

First, an entire configuration of the present system will be described with reference to FIGS. 4 and 5. FIG. 4 is a diagram showing an example of the entire configuration of the present system. FIG. 5 is a diagram showing another example of the entire configuration of the present system. As shown in FIG. 4, the present system is constituted in which the visceral fat accumulation-evaluating apparatus 100 that evaluates the visceral fat accumulation condition in the subject, and the client apparatus 200 (corresponding to the information communication terminal apparatus of the present invention) that provides the amino acid concentration data of the subject on the concentration values of the amino acids, are communicatively connected to each other via a network 300.

In the present system as shown in FIG. 5, in addition to the visceral fat accumulation-evaluating apparatus 100 and the client apparatus 200, the database apparatus 400 storing, for example, the visceral fat accumulation condition information used in preparing the multivariate discriminant and the multivariate discriminant used in evaluating the visceral fat accumulation condition in the visceral fat accumulation-evaluating apparatus 100, may be communicatively connected via the network 300. In this configuration, the information on the visceral fat accumulation condition etc. are provided via the network 300 from the visceral fat accumulation-evaluating apparatus 100 to the client apparatuses 200 and the database apparatus 400, or from the client apparatuses 200 and the database apparatus 400 to the visceral fat accumulation-evaluating apparatus 100. The "information on the visceral fat accumulation condition" is information on measured values of particular items of the visceral fat accumulation condition of organisms including human. The information on the visceral fat accumulation condition is generated in the visceral fat accumulation-evaluating apparatus 100, client apparatus 200, and other apparatuses (e.g., various measuring apparatuses) and stored mainly in the database apparatus 400.

Figure 6:
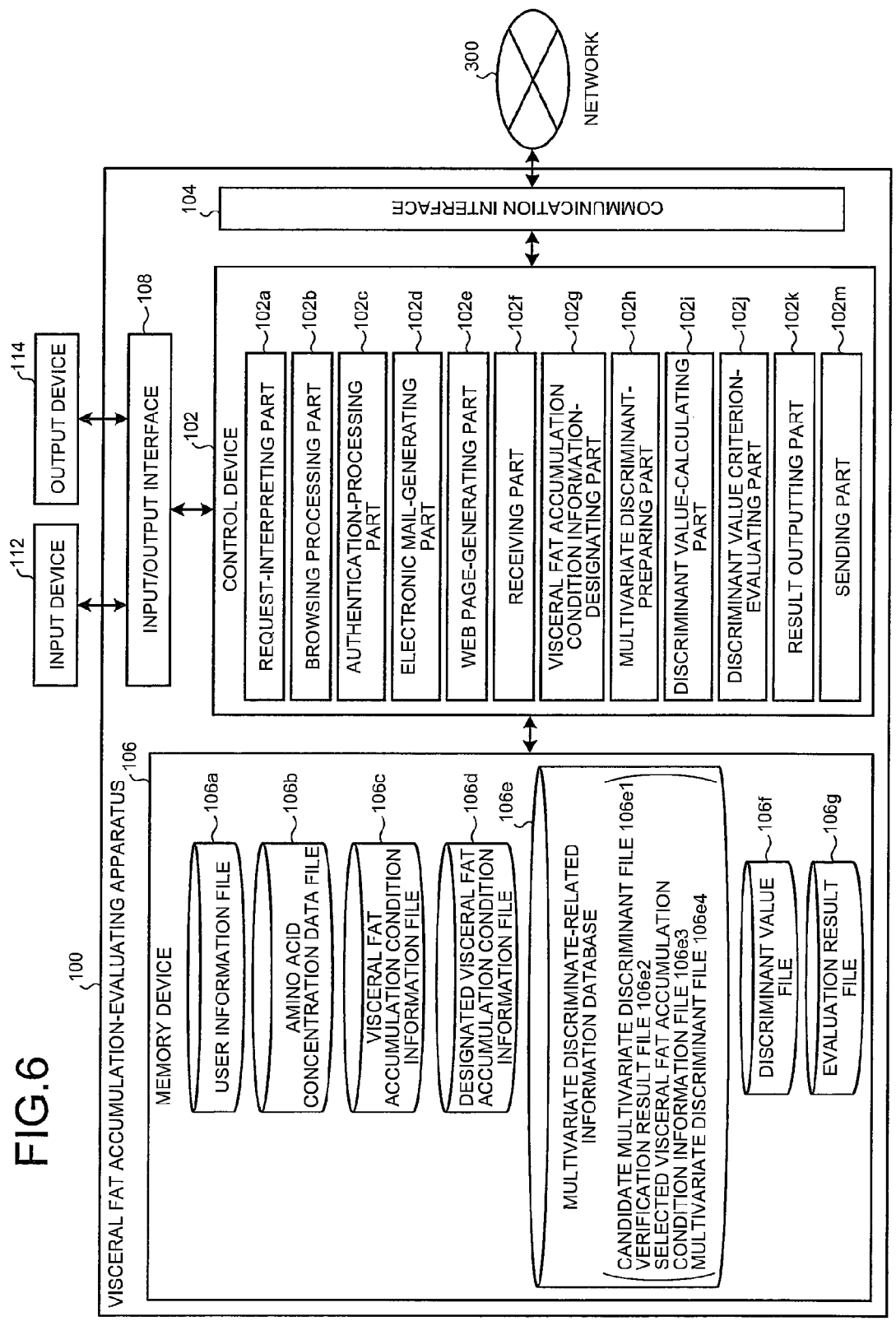
FIG. 6 is a block diagram showing an example of a configuration of a visceral fat accumulation-evaluating apparatus 100 in the present system.

Now, a configuration of the visceral fat accumulation-evaluating apparatus 100 in the present system will be described with reference to FIGS. 6 to 18. FIG. 6 is a block diagram showing an example of the configuration of the visceral fat accumulation-evaluating apparatus 100 in the present system, showing conceptually only the region relevant to the present invention.

The visceral fat accumulation-evaluating apparatus 100 includes (a) a control device 102, such as CPU (Central Processing Unit), that integrally controls the visceral fat accumulation-evaluating apparatus 100, (b) a communication interface 104 that connects the visceral fat accumulation-evaluating apparatus 100 to the network 300 communicatively via communication apparatuses such as a router and wired or wireless communication lines such as a private line, (c) a memory device 106 that stores various databases, tables, files and others, and (d) an input/output interface 108 connected to an input device 112 and an output device 114, and these parts are connected to each other communicatively via any communication channel. The visceral fat accumulation-evaluating apparatus 100 may be present together with various analyzers (e.g., an amino acid analyzer) in a same housing. A typical configuration of disintegration/integration of the visceral fat accumulation-evaluating apparatus 100 is not limited to that shown in the figure, and all or a part of it may be disintegrated or integrated functionally or physically in any unit, for example, according to various loads applied. For example, a part of the processing may be performed via CGI (Common Gateway Interface).

The memory device 106 is a storage means, and examples thereof include memory apparatus such as RAM (Random Access Memory) and ROM (Read Only Memory), a fixed disk drive such as a hard disk, a flexible disk, an optical disk, and the like. The memory device 106 stores computer programs giving instructions to the CPU for various processings, together with OS (Operating System). As shown in the figure, the memory device 106 stores the user information file 106a, the amino acid concentration data file 106b, the visceral fat accumulation condition information file 106c, the designated visceral fat accumulation condition information file 106d, a multivariate discriminant-related information database 106e, the discriminant value file 106f, and the evaluation result file 106g.

The user information file 106a stores user information on users. FIG. 7 is a chart showing an example of information stored in the user information file 106a. As shown in FIG. 7, the information stored in the user information file 106a includes user ID (identification) for identifying a user uniquely, user password for authentication of the user, user name, organization ID for uniquely identifying an organization of the user, department ID for uniquely identifying a department of the user organization, department name, and electronic mail address of the user that are correlated to one another.

Returning to FIG. 6, the amino acid concentration data file 106b stores the amino acid concentration data on the concentration values of the amino acids. FIG. 8 is a chart showing an example of information stored in the amino acid concentration data file 106b. As shown in FIG. 8, the information stored in the amino acid concentration data file 106b includes individual number for uniquely identifying an individual (sample) as a subject to be evaluated and amino acid concentration data that are correlated to one another. In FIG. 8, the amino acid concentration data are assumed to be numerical values, i.e., on a continuous scale, but the amino acid concentration data may be expressed on a nominal scale or an ordinal scale. In the case of the nominal or ordinal scale, any number may be allocated to each state for analysis. The amino acid concentration data may be combined with other biological information (e.g., sex difference, age, height, weight, BMI index, abdominal circumference, insulin resistance index, uric acid level, blood glucose level, triglyceride, body fat percentage, total cholesterol, HDL cholesterol, LDL cholesterol, systolic pressure, diastolic pressure, hemoglobin A1c, arteriosclerosis index, smoking, digitalized electrocardiogram waveform, enzyme concentration, gene expression level, and concentrations of metabolites other than the amino acids).

Returning to FIG. 6, the visceral fat accumulation condition information file 106c stores the visceral fat accumulation condition information used in preparing the multivariate discriminant. FIG. 9 is a chart showing an example of information stored in the visceral fat accumulation condition information file 106c. As shown in FIG. 9, the information stored in the visceral fat accumulation condition information file 106c includes individual number, visceral fat accumulation condition index data (T) corresponding to a visceral fat accumulation condition index (index T1, index T2, index T3 . . . ), and amino acid concentration data that are correlated to one another. In FIG. 9, the visceral fat accumulation condition index data and the amino acid concentration data are assumed to be numerical values, i.e., on a continuous scale, but the visceral fat accumulation condition index data and the amino acid concentration data may be expressed on a nominal scale or an ordinal scale. In the case of nominal or ordinal scale, any number may be allocated to each state for analysis. The visceral fat accumulation condition index data is a single known condition index serving as a marker of the visceral fat accumulation condition, and numerical data may be used.

Returning to FIG. 6, the designated visceral fat accumulation condition information file 106d stores the visceral fat accumulation condition information designated in a visceral fat accumulation condition information-designating part 102g described below. FIG. 10 is a chart showing an example of information stored in the designated visceral fat accumulation condition information file 106d. As shown in FIG. 10, the information stored in the designated visceral fat accumulation condition information file 106d includes individual number, designated visceral fat accumulation condition index data, and designated amino acid concentration data that are correlated to one another.

Returning to FIG. 6, the multivariate discriminant-related information database 106e is composed of the candidate multivariate discriminant file 106e1 storing the candidate multivariate discriminants prepared in a candidate multivariate discriminant-preparing part 102h1 described below; the verification result file 106e2 storing the verification results obtained in a candidate multivariate discriminant-verifying part 102h2 described below; the selected visceral fat accumulation condition information file 106e3 storing the visceral fat accumulation condition information containing the combination of the amino acid concentration data selected in an explanatory variable-selecting part 102h3 described below; and the multivariate discriminant file 106e4 storing the multivariate discriminants prepared in the multivariate discriminant-preparing part 102h described below.

The candidate multivariate discriminant file 106e1 stores the candidate multivariate discriminants prepared in the candidate multivariate discriminant-preparing part 102h1 described below. FIG. 11 is a chart showing an example of information stored in the candidate multivariate discriminant file 106e1. As shown in FIG. 11, the information stored in the candidate multivariate discriminant file 106e1 includes rank, and candidate multivariate discriminant (e.g., F1 (Gly, Leu, Phe, . . . ), F2 (Gly, Leu, Phe, . . . ), or F3 (Gly, Leu, Phe, . . . ) in FIG. 11) that are correlated to each other.

Returning to FIG. 6, the verification result file 106e2 stores the verification results obtained in the candidate multivariate discriminant-verifying part 102h2 described below. FIG. 12 is a chart showing an example of information stored in the verification result file 106e2. As shown in FIG. 12, the information stored in the verification result file 106e2 includes rank, candidate multivariate discriminant (e.g., Fk (Gly, Leu, Phe, . . . ), Fm (Gly, Leu, Phe, . . . ), Fl (Gly, Leu, Phe, . . . ) in FIG. 12), and verification result of each candidate multivariate discriminant (e.g., evaluation value of each candidate multivariate discriminant) that are correlated to one another.

Returning to FIG. 6, the selected visceral fat accumulation condition information file 106e3 stores the visceral fat accumulation condition information including the combination of the amino acid concentration data corresponding to the explanatory variables selected in the explanatory variable-selecting part 102h3 described below. FIG. 13 is a chart showing an example of information stored in the selected visceral fat accumulation condition information file 106e3. As shown in FIG. 13, the information stored in the selected visceral fat accumulation condition information file 106e3 includes individual number, visceral fat accumulation condition index data designated in the visceral fat accumulation condition information-designating part 102g described below, and amino acid concentration data selected in the explanatory variable-selecting part 102h3 described below that are correlated to one another.

Returning to FIG. 6, the multivariate discriminant file 106e4 stores the multivariate discriminants prepared in the multivariate discriminant-preparing part 102h described below. FIG. 14 is a chart showing an example of information stored in the multivariate discriminant file 106e4. As shown in FIG. 14, the information stored in the multivariate discriminant file 106e4 includes rank, multivariate discriminant (e.g., Fp (Phe, . . . ), Fp (Gly, Leu, Phe), Fk (Gly, Leu, Phe, . . . ) in FIG. 14), threshold corresponding to each discriminant-preparing method, and verification result of each multivariate discriminant (e.g., evaluation value of each multivariate discriminant) that are correlated to one another.

Returning to FIG. 6, the discriminant value file 106f stores the discriminant values calculated in a discriminant value-calculating part 102i described below. FIG. 15 is a chart showing an example of information stored in the discriminant value file 106f. As shown in FIG. 15, the information stored in the discriminant value file 106f includes individual number for uniquely identifying the individual (sample) as the subject, rank (number for uniquely identifying the multivariate discriminant), and discriminant value that are correlated to one another.

Figures 16, 17:
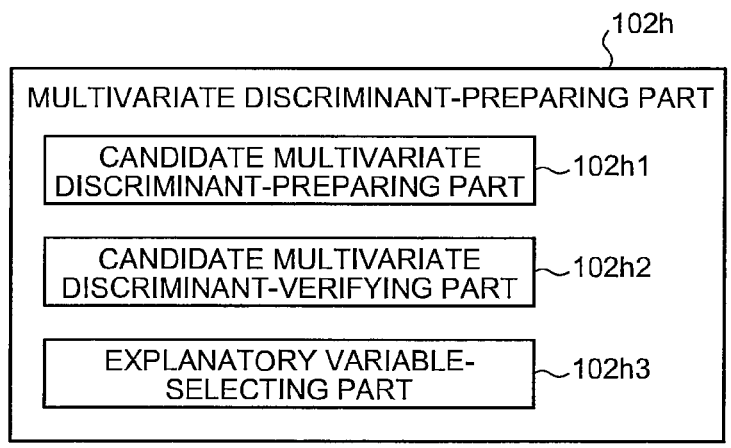
FIG. 16 is a chart showing an example of information stored in an evaluation result file 106g.
FIG. 17 is a block diagram showing a configuration of a multivariate discriminant-preparing part 102h.

Returning to FIG. 6, the evaluation result file 106g stores the evaluation results obtained in the discriminant value criterion-evaluating part 102j described below (specifically the discrimination results obtained in the discriminant value criterion-discriminating part 102j1 described below). FIG. 16 is a chart showing an example of information stored in the evaluation result file 106g. The information stored in the evaluation result file 106g includes individual number for uniquely identifying the individual (sample) as the subject, previously obtained amino acid concentration data of the subject, discriminant value calculated in the multivariate discriminant, and evaluation result on the visceral fat accumulation condition (specifically, discrimination result on the discrimination between the visceral fat accumulation group and the visceral fat accumulation-free group, evaluation result on the visceral fat area state) that are correlated to one another.

Returning to FIG. 6, the memory device 106 stores various Web data for providing the client apparatuses 200 with web site information, CGI programs, and others as information other than the information described above. The Web data include data for displaying various Web pages described below and others, and the data are generated as, for example, HTML (HyperText Markup Language) or XML (Extensible Markup Language) text files. Files for components and files for operation for generation of the Web data, other temporary files, and the like are also stored in the memory device 106. In addition, the memory device 106 may store as needed sound files of sounds for transmission to the client apparatuses 200 in WAVE format or AIFF (Audio Interchange File Format) format and image files of still images or motion pictures in JPEG (Joint Photographic Experts Group) format or MPEG2 (Moving Picture Experts Group phase 2) format.

The communication interface 104 allows communication between the visceral fat accumulation-evaluating apparatus 100 and the network 300 (or a communication apparatus such as a router). Thus, the communication interface 104 has a function to communicate data via a communication line with other terminals.

The input/output interface 108 is connected to the input device 112 and the output device 114. A monitor (including a home television), a speaker, or a printer may be used as the output device 114 (hereinafter, the output device 114 may be described as a monitor 114). A keyboard, a mouse, a microphone, or a monitor functioning as a pointing device together with a mouse may be used as the input device 112.

The control device 102 has an internal memory storing control programs such as OS (Operating System), programs for various processing procedures, and other needed data, and performs various information processings according to these programs. As shown in the figure, the control device 102 includes mainly a request-interpreting part 102a, a browsing processing part 102b, an authentication-processing part 102c, an electronic mail-generating part 102d, a Web page-generating part 102e, a receiving part 102f, the visceral fat accumulation condition information-designating part 102g, the multivariate discriminant-preparing part 102h, the discriminant value-calculating part 102i, the discriminant value criterion-evaluating part 102j, a result outputting part 102k, and a sending part 102m. The control device 102 performs data processings such as removal of data including defective, removal of data including many outliers, and removal of explanatory variables for the defective-including data in the visceral fat accumulation condition information transmitted from the database apparatus 400 and in the amino acid concentration data transmitted from the client apparatus 200.

The request-interpreting part 102a interprets requests transmitted from the client apparatus 200 or the database apparatus 400 and sends the requests to other parts in the control device 102 according to results of interpreting the requests. Upon receiving browsing requests for various screens transmitted from the client apparatus 200, the browsing processing part 102b generates and transmits Web data for these screens. Upon receiving authentication requests transmitted from the client apparatus 200 or the database apparatus 400, the authentication-processing part 102c performs authentication. The electronic mail-generating part 102d generates electronic mails including various kinds of information. The Web page-generating part 102e generates Web pages for users to browse with the client apparatus 200.

The receiving part 102f receives, via the network 300, information (specifically, the amino acid concentration data, the visceral fat accumulation condition information, the multivariate discriminant etc.) transmitted from the client apparatus 200 or the database apparatus 400. The visceral fat accumulation condition information-designating part 102g designates objective visceral fat accumulation condition index data and objective amino acid concentration data in preparing the multivariate discriminant.

The multivariate discriminant-preparing part 102h generates the multivariate discriminants based on the visceral fat accumulation condition information received in the receiving part 102f and the visceral fat accumulation condition information designated in the visceral fat accumulation condition information-designating part 102g. Specifically, the multivariate discriminant-preparing part 102h prepares the multivariate discriminant by selecting the candidate multivariate discriminant to be used as the multivariate discriminant from a plurality of the candidate multivariate discriminants, based on verification results accumulated by repeating processings in the candidate multivariate discriminant-preparing part 102h1, the candidate multivariate discriminant-verifying part 102h2, and the explanatory variable-selecting part 102h3 from the visceral fat accumulation condition information.

If the multivariate discriminant is stored previously in a predetermined region of the memory device 106, the multivariate discriminant-preparing part 102h may prepares the multivariate discriminant by selecting the desired multivariate discriminant out of the memory device 106. Alternatively, the multivariate discriminant-preparing part 102h may prepare the multivariate discriminant by selecting and downloading the desired multivariate discriminant from the multivariate discriminants previously stored in another computer apparatus (e.g., the database apparatus 400).

Hereinafter, a configuration of the multivariate discriminant-preparing part 102h will be described with reference to FIG. 17. FIG. 17 is a block diagram showing the configuration of the multivariate discriminant-preparing part 102h, and only a part in the configuration related to the present invention is shown conceptually. The multivariate discriminant-preparing part 102h has the candidate multivariate discriminant-preparing part 102h1, the candidate multivariate discriminant-verifying part 102h2, and the explanatory variable-selecting part 102h3, additionally. The candidate multivariate discriminant-preparing part 102h1 prepares the candidate multivariate discriminant that is a candidate of the multivariate discriminant, from the visceral fat accumulation condition information based on a predetermined discriminant-preparing method. The candidate multivariate discriminant-preparing part 102h1 may prepare a plurality of the candidate multivariate discriminants from the visceral fat accumulation condition information, by using a plurality of the different discriminant-preparing methods. The candidate multivariate discriminant-verifying part 102h2 verifies the candidate multivariate discriminants prepared in the candidate multivariate discriminant-preparing part 102h1 based on a predetermined verifying method. The candidate multivariate discriminant-verifying part 102h2 may verify at least one of the discrimination rate, sensitivity, specificity, and information criterion of the candidate multivariate discriminants based on at least one of the bootstrap method, holdout method, and leave-one-out method. The explanatory variable-selecting part 102h3 selects the combination of the amino acid concentration data contained in the visceral fat accumulation condition information used in preparing the candidate multivariate discriminant, by selecting the explanatory variables of the candidate multivariate discriminant based on a predetermined explanatory variable-selecting method from the verification results obtained in the candidate multivariate discriminant-verifying part 102h2. The explanatory variable-selecting part 102h3 may select the explanatory variables of the candidate multivariate discriminant based on at least one of the stepwise method, best path method, local search method, and genetic algorithm from the verification results.

Returning to FIG. 6, the discriminant value-calculating part 102i calculates the discriminant value that is a value of the multivariate discriminant, based on the amino acid concentration data (for example, the concentration value of at least one of Val, Leu, Ile, Tyr, Phe, Trp, Glu, Ala, Pro, Orn, Lys, Gly, Ser, Met, Arg, Cys, and Gln) of the subject received in the receiving part 102f and the multivariate discriminant (for example, the multivariate discriminant containing at least one of Val, Leu, Ile, Tyr, Phe, Trp, Glu, Ala, Pro, Orn, Lys, Gly, Ser, Met, Arg, Cys, and Gln as the explanatory variable) prepared in the multivariate discriminant-preparing part 102h.

The multivariate discriminant may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be formula 1, formula 2, the logistic regression equation with Ser, Glu, Ile, Tyr, and Arg as the explanatory variables, the logistic regression equation with Ser, Glu, Leu, and Trp as the explanatory variables, formula 3, or formula 4.

$$(Glu+Tyr+Orn)/(Asn+Ser) \qquad \text{(formula 1)}$$

$$(Glu+Leu)/(Ser+Tau)+(Pro+Orn)/(Gln) \qquad \text{(formula 2)}$$

$$(Glu+Gly)+(-0.2)\times(Ser/Tyr)+(-0.1)\times(His/Trp) \qquad \text{(formula 3)}$$

$$(Glu/Gly)+(-0.54)\times(Ser/Leu)+(0.15)\times(Pro/Trp)+(-0.05)\times(Gln/Tyr) \qquad \text{(formula 4)}$$

Figure 18:
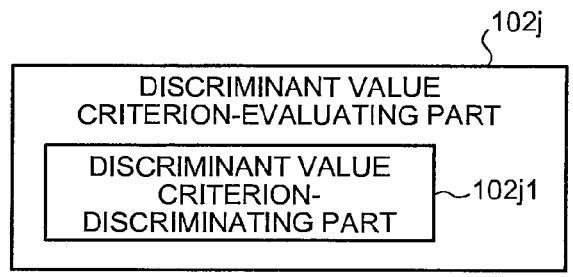
FIG. 18 is a block diagram showing a configuration of a discriminant value criterion-evaluating part 102j.

The discriminant value criterion-evaluating part 102j evaluates the visceral fat accumulation condition in the subject based on the discriminant value calculated in the discriminant value-calculating part 102i. The discriminant value criterion-evaluating part 102j may evaluate the visceral fat area state in the subject based on the discriminant value calculated in the discriminant value-calculating part 102*i*. Specifically, the discriminant value criterion-evaluating part 102*j* compares the discriminant value with a previously established threshold (cutoff value), thereby evaluating the visceral fat area state in the subject. The discriminant value criterion-evaluating part 102*j* further includes the discriminant value criterion-discriminating part 102*j*1. Now, a configuration of the discriminant value criterion-evaluating part 102*j* will be described with reference to FIG. 18. FIG. 18 is a block diagram showing the configuration of the discriminant value criterion-evaluating part 102*j*, and only a part in the configuration related to the present invention is shown conceptually. The discriminant value criterion-discriminating part 102*j*1 discriminates between the visceral fat accumulation group and the visceral fat accumulation-free group in the subject based on the discriminant value. Specifically, the discriminant value criterion-discriminating part 102*j*1 compares the discriminant value with a previously established threshold (cutoff value), thereby discriminating between the visceral fat accumulation group and the visceral fat accumulation-free group in the subject.

Returning to FIG. 6, the result outputting part 102*k* outputs, into the output device 114, the processing results in each processing part in the control device 102 (the evaluation results obtained in the discriminant value criterion-evaluating part 102*j* (specifically the discrimination results obtained in the discriminant value criterion-discriminating part 102*j*1)) etc.

The sending part 102*m* transmits the evaluation results to the client apparatus 200 that is a sender of the amino acid concentration data of the subject, and transmits the multivariate discriminants prepared in the visceral fat accumulation-evaluating apparatus 100 and the evaluation results to the database apparatus 400.

Figure 19:
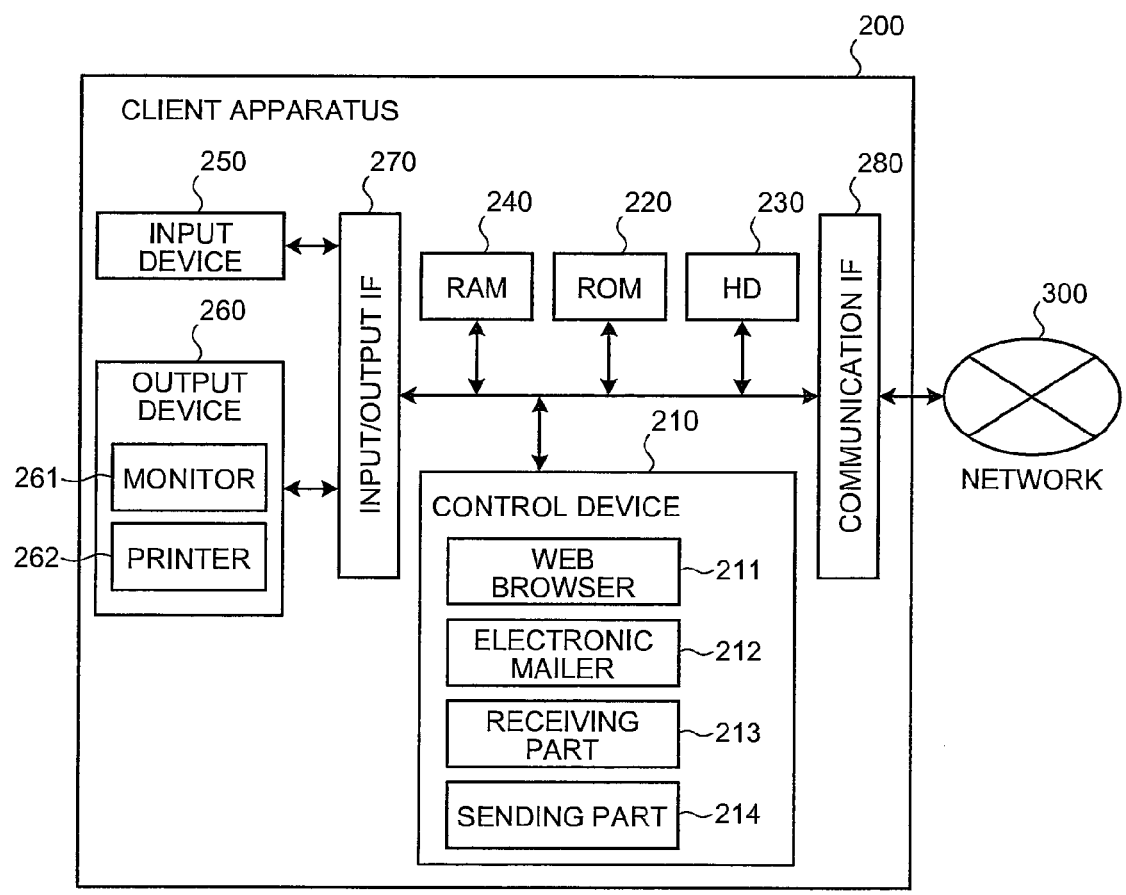
FIG. 19 is a block diagram showing an example of a configuration of a client apparatus 200 in the present system.

Hereinafter, a configuration of the client apparatus 200 in the present system will be described with reference to FIG. 19. FIG. 19 is a block diagram showing an example of the configuration of the client apparatus 200 in the present system, and only the part in the configuration relevant to the present invention is shown conceptually.

The client apparatus 200 includes a control device 210, ROM 220, HD (Hard Disk) 230, RAM 240, an input device 250, an output device 260, an input/output IF 270, and a communication IF 280 that are connected communicatively to one another through a communication channel.

The control device 210 has a Web browser 211, an electronic mailer 212, a receiving part 213, and a sending part 214. The Web browser 211 performs browsing processings of interpreting Web data and displaying the interpreted Web data on a monitor 261 described below. The Web browser 211 may have various plug-in softwares such as stream player having functions to receive, display and feedback streaming screen images. The electronic mailer 212 sends and receives electronic mails using a particular protocol (e.g., SMTP (Simple Mail Transfer Protocol) or POP3 (Post Office Protocol version 3)). The receiving part 213 receives various kinds of information such as the evaluation results transmitted from the visceral fat accumulation-evaluating apparatus 100, via the communication IF 280. The sending part 214 sends various kinds of information such as the amino acid concentration data of the subject, via the communication IF 280 to the visceral fat accumulation-evaluating apparatus 100.

The input device 250 is for example a keyboard, a mouse, or a microphone. The monitor 261 described below also functions as a pointing device together with a mouse. The output device 260 is an output means for outputting information received via the communication IF 280, and includes the monitor 261 (including a home television) and a printer 262. In addition, the output device 260 may have a speaker or the like additionally. The input/output IF 270 is connected to the input device 250 and the output device 260.

The communication IF 280 connects the client apparatus 200 to the network 300 (or communication apparatus such as router) communicatively. In other words, the client apparatuses 200 are connected to the network 300 via a communication apparatus such as a modem, TA (Terminal Adapter) or a router, and a telephone line, or a private line. In this way, the client apparatuses 200 can access to the visceral fat accumulation-evaluating apparatus 100 by using a particular protocol.

The client apparatus 200 may be realized by installing softwares (including programs, data and others) for a Web data-browsing function and an electronic mail-processing function to an information processing apparatus (for example, an information processing terminal such as a known personal computer, a workstation, a family computer, Internet TV (Television), PHS (Personal Handyphone System) terminal, a mobile phone terminal, a mobile unit communication terminal or PDA (Personal Digital Assistants)) connected as needed with peripheral devices such as a printer, a monitor, and a image scanner.

All or a part of processings of the control device 210 in the client apparatus 200 may be performed by CPU and programs read and executed by the CPU. Computer programs for giving instructions to the CPU and executing various processings together with OS (Operating System) are recorded in the ROM 220 or HD 230. The computer programs, which are executed as they are loaded in the RAM 240, constitute the control device 210 with the CPU. The computer programs may be stored in application program servers connected via any network to the client apparatus 200, and the client apparatus 200 may download all or a part of them as needed. All or any part of processings of the control device 210 may be realized by hardwares such as wired-logic.

Hereinafter, the network 300 in the present system will be described with reference to FIGS. 4 and 5. The network 300 has a function to connect the visceral fat accumulation-evaluating apparatus 100, the client apparatuses 200, and the database apparatus 400 mutually, communicatively to one another, and is for example the Internet, an intranet, or LAN (Local Area Network (including both wired/wireless)). The network 300 may be VAN (Value Added Network), a personal computer communication network, a public telephone network (including both analog and digital), a leased line network (including both analog and digital), CATV (Community Antenna Television) network, a portable switched network or a portable packet-switched network (including IMT2000 (International Mobile Telecommunication 2000) system, GSM (Global System for Mobile Communications) system, PDC (Personal Digital Cellular)/PDC-P system, and the like), a wireless calling network, a local wireless network such as Bluetooth (registered trademark), PHS network, a satellite communication network (including CS (Communication Satellite), BS (Broadcasting Satellite), ISDB (Integrated Services Digital Broadcasting), and the like), or the like.

Figure 20:
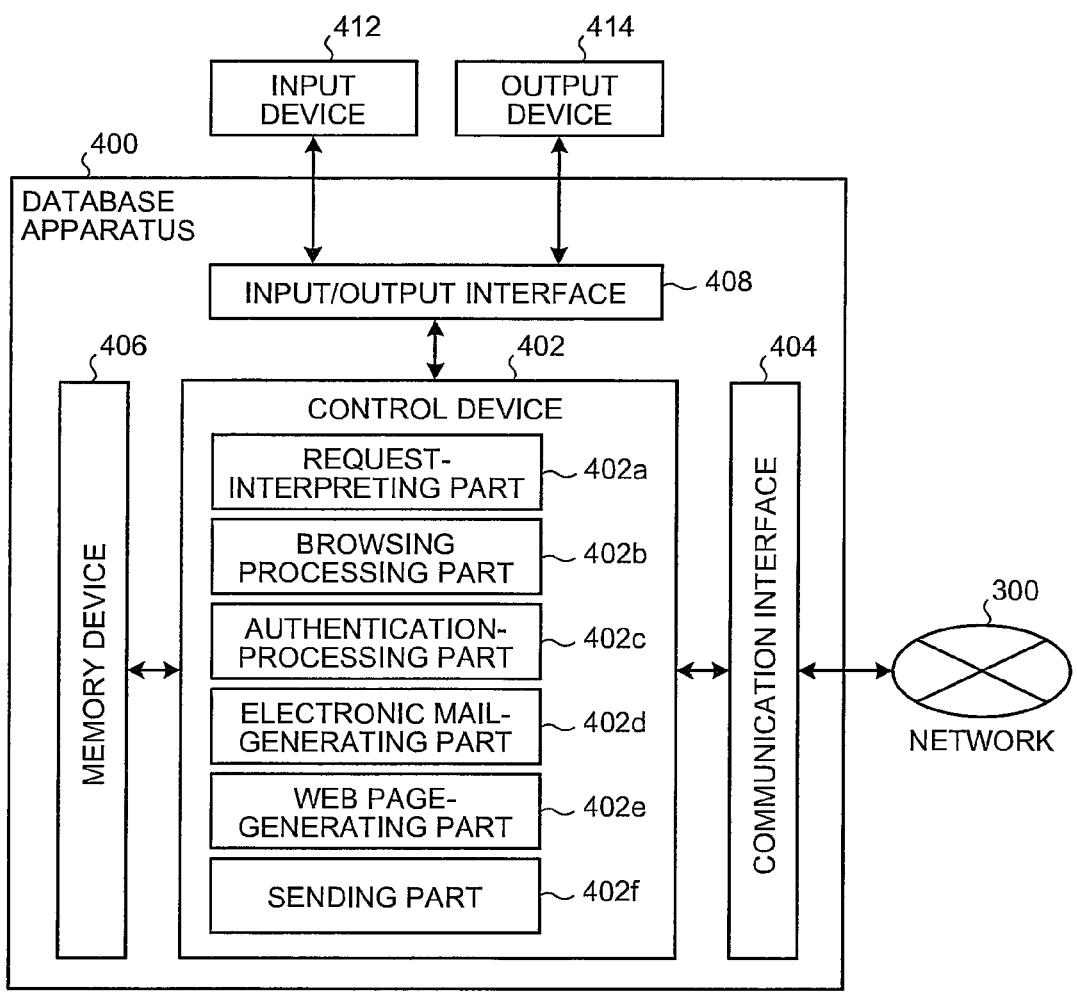
FIG. 20 is a block diagram showing an example of a configuration of a database apparatus 400 in the present system.

Hereinafter, a configuration of the database apparatus 400 in the present system will be described with reference to FIG. 20. FIG. 20 is a block diagram showing an example of the configuration of the database apparatus 400 in the present system, showing conceptually only the region relevant to the present invention.

The database apparatus 400 has functions to store, for example, the visceral fat accumulation condition information used in preparing the multivariate discriminants in the visceral fat accumulation-evaluating apparatus 100 or in the database apparatus 400, the multivariate discriminants prepared in the visceral fat accumulation-evaluating apparatus 100, and the evaluation results obtained in the visceral fat accumulation-evaluating apparatus 100. As shown in FIG. 20, the database apparatus 400 includes (a) a control device 402, such as CPU, which integrally controls the entire database apparatus 400, (b) a communication interface 404 connecting the database apparatus 400 to the network 300 communicatively via communication apparatuses such as a router and via wired or wireless communication circuits such as a private line, (c) a memory device 406 storing various databases, tables and files (for example, files for Web pages), and (d) an input/output interface 408 connected to an input device 412 and an output device 414, and these parts are connected communicatively to each other via any communication channel.

The memory device 406 is a storage means, and may be, for example, memory apparatus such as RAM and ROM, a fixed disk drive such as a hard disk, a flexible disk, an optical disk, and the like. The memory device 406 stores various programs used in various processings. The communication interface 404 allows communication between the database apparatus 400 and the network 300 (or a communication apparatus such as a router). Thus, the communication interface 404 has a function to communicate data via a communication line with other terminals. The input/output interface 408 is connected to the input device 412 and the output device 414. A monitor (including a home television), a speaker, or a printer may be used as the output device 414 (hereinafter, the output device 414 may be described as a monitor 414). A keyboard, a mouse, a microphone, or a monitor functioning as a pointing device together with a mouse may be used as the input device 412.

The control device 402 has an internal memory storing control programs such as OS (Operating System), programs for various processing procedures, and other needed data, and performs various information processings according to these programs. As shown in the figure, the control device 402 includes mainly a request-interpreting part 402*a*, a browsing processing part 402*b*, an authentication-processing part 402*c*, an electronic mail-generating part 402*d*, a Web page-generating part 402*e*, and a sending part 402*f*.

The request-interpreting part 402*a* interprets requests transmitted from the visceral fat accumulation-evaluating apparatus 100 and sends the requests to other parts in the control device 402 according to results of interpreting the requests. Upon receiving browsing requests for various screens transmitted from the visceral fat accumulation-evaluating apparatus 100, the browsing processing part 402*b* generates and transmits Web data for these screens. Upon receiving authentication requests transmitted from the visceral fat accumulation-evaluating apparatus 100, the authentication-processing part 402*c* performs authentication. The electronic mail-generating part 402*d* generates electronic mails including various kinds of information. The Web page-generating part 402*e* generates Web pages for users to browse with the client apparatus 200. The sending part 402*f* transmits various kinds of information such as the visceral fat accumulation condition information and the multivariate discriminants to the visceral fat accumulation-evaluating apparatus 100.

2-3. Processing in the Present System

Figure 21:
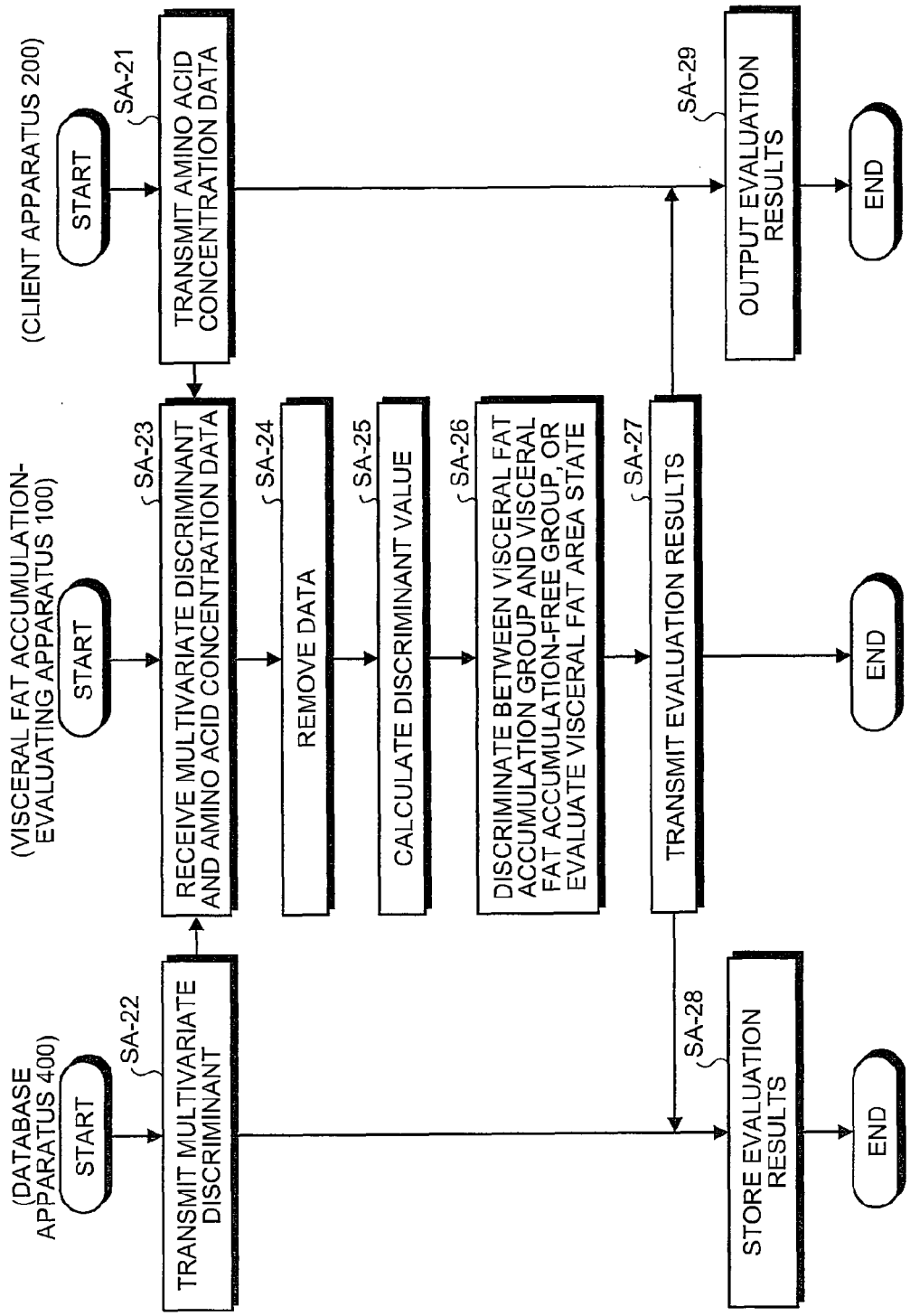
FIG. 21 is a flowchart showing an example of a visceral fat accumulation evaluation service processing performed in the present system.

Here, an example of a visceral fat accumulation evaluation service processing performed in the present system constituted as described above will be described with reference to FIG. 21. FIG. 21 is a flowchart showing the example of the visceral fat accumulation evaluation service processing.

The amino acid concentration data used in the present processing is data concerning the concentration values of the amino acids obtained by analyzing blood previously collected from an individual. Hereinafter, the method of analyzing blood amino acid will be described briefly. First, a blood sample is collected in a heparin-treated tube, and then the blood plasma is separated by centrifugation of the tube. All blood plasma samples separated are frozen and stored at $-70°$ C. before a measurement of an amino acid concentration. Before the measurement of the amino acid concentration, the blood plasma samples are deproteinized by adding sulfosalicylic acid to a concentration of 3%. An amino acid analyzer by high-performance liquid chromatography (HPLC) by using ninhydrin reaction in post column is used for the measurement of the amino acid concentration.

First, the client apparatus 200 accesses the visceral fat accumulation-evaluating apparatus 100 when the user specifies the Web site address (such as URL) provided from the visceral fat accumulation-evaluating apparatus 100, via the input device 250 on the screen displaying the Web browser 211. Specifically, when the user instructs an update of the Web browser 211 screen on the client apparatus 200, the Web browser 211 sends the Web site address provided from the visceral fat accumulation-evaluating apparatus 100 by a particular protocol to the visceral fat accumulation-evaluating apparatus 100, thereby transmitting requests demanding a transmission of Web page corresponding to an amino acid concentration data transmission screen to the visceral fat accumulation-evaluating apparatus 100 based on a routing of the address.

Then, upon receiving the requests transmitted from the client apparatus 200, the request-interpreting part 102*a* in the visceral fat accumulation-evaluating apparatus 100 analyzes the transmitted requests and sends the requests to other parts in the control device 102 according to analysis results. Specifically, when the transmitted requests are requests to send the Web page corresponding to the amino acid concentration data transmission screen, mainly the browsing processing part 102*b* in the visceral fat accumulation-evaluating apparatus 100 obtains the Web data for displaying the Web page stored in a predetermined region of the memory device 106 and sends the obtained Web data to the client apparatus 200. More specifically, upon receiving the requests to transmit the Web page corresponding to the amino acid concentration data transmission screen by the user, the control device 102 in the visceral fat accumulation-evaluating apparatus 100 demands inputs of user ID and user password from the user. If the user ID and password are input, the authentication-processing part 102*c* in the visceral fat accumulation-evaluating apparatus 100 examines the input user ID and password by comparing them with the user ID and user password stored in the user information file 106*a* for authentication. Only when the user is authenticated, the browsing processing part 102*b* in the visceral fat accumulation-evaluating apparatus 100 sends the Web data for displaying the Web page corresponding to the amino acid concentration data transmission screen to the client apparatus 200. The client apparatus 200 is identified with the IP (Internet Protocol) address transmitted from the client apparatus 200 together with the transmission requests.

Then, the client apparatus 200 receives, in the receiving part 213, the Web data (for displaying the Web page corresponding to the amino acid concentration data transmission screen) transmitted from the visceral fat accumulation-evaluating apparatus 100, interprets the received Web data with the Web browser 211, and displays the amino acid concentration data transmission screen on the monitor 261.

When the user inputs and selects, via the input device 250, for example the amino acid concentration data of the individual on the amino acid concentration data transmission screen displayed on the monitor 261, the sending part 214 in the client apparatus 200 transmits an identifier for identifying input information and selected items to the visceral fat accumulation-evaluating apparatus 100, thereby transmitting the amino acid concentration data of the individual as the subject to the visceral fat accumulation-evaluating apparatus 100 (step SA-21). In the step SA-21, the transmission of the amino acid concentration data may be realized for example by using an existing file transfer technology such as FTP (File Transfer Protocol).

Then, the request-interpreting part 102*a* in the visceral fat accumulation-evaluating apparatus 100 interprets the identifier transmitted from the client apparatus 200 thereby interpreting the requests from the client apparatus 200, and requests the database apparatus 400 to send the multivariate discriminants for an evaluation of the visceral fat accumulation (specifically, for a discrimination between the 2 groups of the visceral fat accumulation group and the visceral fat accumulation-free group, for an evaluation of the visceral fat area state) containing at least one of Val, Leu, Ile, Tyr, Phe, Trp, Glu, Ala, Pro, Orn, Lys, Gly, Ser, Met, Arg, Cys, and Gln as the explanatory variable.

Then, the request-interpreting part 402*a* in the database apparatus 400 interprets the transmission requests from the visceral fat accumulation-evaluating apparatus 100 and transmits, to the visceral fat accumulation-evaluating apparatus 100, the multivariate discriminant (for example, the updated newest multivariate discriminant) stored in a predetermined memory region of the memory device 406 containing at least one of Val, Leu, Ile, Tyr, Phe, Trp, Glu, Ala, Pro, Orn, Lys, Gly, Ser, Met, Arg, Cys, and Gln as the explanatory variable (step SA-22).

In the step SA-22, the multivariate discriminant transmitted to the visceral fat accumulation-evaluating apparatus 100 may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant transmitted to the visceral fat accumulation-evaluating apparatus 100 may be formula 1, formula 2, the logistic regression equation with Ser, Glu, Ile, Tyr, and Arg as the explanatory variables, the logistic regression equation with Ser, Glu, Leu, and Trp as the explanatory variables, formula 3, or formula 4.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

The visceral fat accumulation-evaluating apparatus 100 receives, in the receiving part 102*f*, the amino acid concentration data of the individual transmitted from the client apparatuses 200 and the multivariate discriminant transmitted from the database apparatus 400, and stores the received amino acid concentration data in a predetermined memory region of the amino acid concentration data file 106*b* and the received multivariate discriminant in a predetermined memory region of the multivariate discriminant file 106*e*4 (step SA-23).

Then, the control device 102 in the visceral fat accumulation-evaluating apparatus 100 removes data such as defective and outliers from the amino acid concentration data of the individual received in the step SA-23 (step SA-24).

Then, the discriminant value-calculating part 102*i* in the visceral fat accumulation-evaluating apparatus 100 calculates the discriminant value based on both the multivariate discriminant received in the step SA-23 and the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the individual from which the data such as the defective and outliers have been removed in the step SA-24 (step SA-25).

Then, the discriminant value criterion-discriminating part 102*j*1 in the visceral fat accumulation-evaluating apparatus 100 compares the discriminant value calculated in the step SA-25 with a previously established threshold (cutoff value), thereby discriminating between the visceral fat accumulation group and the visceral fat accumulation-free group or evaluating the visceral fat area state in the individual, and stores the discrimination results or evaluation results in a predetermined memory region of the evaluation result file 106*g* (step SA-26).

Then, the sending part 102*m* in the visceral fat accumulation-evaluating apparatus 100 sends, to the client apparatus 200 that has sent the amino acid concentration data and to the database apparatus 400, the discrimination results (the discrimination results on the discrimination between the visceral fat accumulation group and the visceral fat accumulation-free group) or the evaluation results (the evaluation results on the visceral fat area state) obtained in the step SA-26 (step SA-27). Specifically, the visceral fat accumulation-evaluating apparatus 100 first generates a Web page for displaying the discrimination results or evaluation results in the Web page-generating part 102*e* and stores the Web data corresponding to the generated Web page in a predetermined memory region of the memory device 106. Then, the user is authenticated as described above by inputting a predetermined URL (Uniform Resource Locator) into the Web browser 211 of the client apparatus 200 via the input device 250, and the client apparatus 200 sends a Web page browsing request to the visceral fat accumulation-evaluating apparatus 100. The visceral fat accumulation-evaluating apparatus 100 then interprets the browsing request transmitted from the client apparatus 200 in the browsing processing part 102*b* and reads the Web data corresponding to the Web page for displaying the discrimination results or evaluation results, out of the predetermined memory region of the memory device 106. The sending part 102*m* in the visceral fat accumulation-evaluating apparatus 100 then sends the read-out Web data to the client apparatus 200 and simultaneously sends the Web data or the discrimination results or evaluation results to the database apparatus 400.

In the step SA-27, the control device 102 in the visceral fat accumulation-evaluating apparatus 100 may notify the discrimination results or evaluation results to the user client apparatus 200 by electronic mail. Specifically, the electronic mail-generating part 102*d* in the visceral fat accumulation-evaluating apparatus 100 first acquires the user electronic mail address by referencing the user information stored in the user information file 106*a* based on the user ID and the like at the transmission timing. The electronic mail-generating part 102d in the visceral fat accumulation-evaluating apparatus 100 then generates electronic mail data with the acquired electronic mail address as its mail address, including the user name and the discrimination results or evaluation results. The sending part 102m in the visceral fat accumulation-evaluating apparatus 100 then transmits the generated electronic mail data to the user client apparatus 200.

Also in the step SA-27, the visceral fat accumulation-evaluating apparatus 100 may send the discrimination results or evaluation results to the user client apparatus 200 by using, for example, an existing file transfer technology such as FTP.

Returning to FIG. 21, the control device 402 in the database apparatus 400 receives the discrimination results or evaluation results or the Web data transmitted from the visceral fat accumulation-evaluating apparatus 100 and stores (accumulates) the received discrimination results or evaluation results or the received Web data in a predetermined memory region of the memory device 406 (step SA-28).

The receiving part 213 in the client apparatus 200 receives the Web data transmitted from the visceral fat accumulation-evaluating apparatus 100, and the received Web data is interpreted with the Web browser 211, to display on the monitor 261 the Web page screen displaying the discrimination results or evaluation results of the individual (step SA-29). When the discrimination results or evaluation results are sent from the visceral fat accumulation-evaluating apparatus 100 by electronic mail, the electronic mail transmitted from the visceral fat accumulation-evaluating apparatus 100 is received at any timing, and the received electronic mail is displayed on the monitor 261 with the known function of the electronic mailer 212 in the client apparatus 200.

In this way, the user can confirm the discrimination results on the discrimination of the 2 groups of the visceral fat accumulation group and the visceral fat accumulation-free group in the individual or the evaluation results on the visceral fat area state in the individual, by browsing the Web page displayed on the monitor 261. The user can print out the contents of the Web page displayed on the monitor 261 by the printer 262.

When the discrimination results or evaluation results are transmitted by electronic mail from the visceral fat accumulation-evaluating apparatus 100, the user reads the electronic mail displayed on the monitor 261, whereby the user can confirm the discrimination results on the discrimination of the 2 groups of the visceral fat accumulation group and the visceral fat accumulation-free group in the individual or the evaluation results on the visceral fat area state in the individual. The user may print out the contents of the electronic mail displayed on the monitor 261 by the printer 262.

Given the foregoing description, the explanation of the visceral fat accumulation evaluation service processing is finished.

2-4. Summary of the Second Embodiment and Other Embodiments

According to the visceral fat accumulation-evaluating system described above in detail, the client apparatus 200 sends the amino acid concentration data of the individual to the visceral fat accumulation-evaluating apparatus 100. Upon receiving the requests from the visceral fat accumulation-evaluating apparatus 100, the database apparatus 400 transmits the multivariate discriminant for the discrimination of the 2 groups of the visceral fat accumulation group and the visceral fat accumulation-free group or the multivariate discriminant for the evaluation of the visceral fat area state, to the visceral fat accumulation-evaluating apparatus 100. By the visceral fat accumulation-evaluating apparatus 100, (1) the amino acid concentration data transmitted from the client apparatus 200 is received and the multivariate discriminant transmitted from the database apparatus 400 is received simultaneously, (2) the discriminant value are calculated based on the received amino acid concentration data and the received multivariate discriminant, (3) the calculated discriminant value are compared with the previously established threshold, thereby discriminating between the visceral fat accumulation group and the visceral fat accumulation-free group or evaluating the visceral fat area state in the individual, and (4) the discrimination results or evaluation results are transmitted to the client apparatus 200 and database apparatus 400. Then, the client apparatus 200 receives and displays the discrimination results or evaluation results transmitted from the visceral fat accumulation-evaluating apparatus 100, and the database apparatus 400 receives and stores the discrimination results or evaluation results transmitted from the visceral fat accumulation-evaluating apparatus 100. Thus, the discriminant values obtained in the multivariate discriminants useful for discriminating between the 2 groups of the visceral fat accumulation group and the visceral fat accumulation-free group or evaluating the visceral fat area state can be utilized to bring about an effect of enabling an accurate discrimination between the 2 groups of the visceral fat accumulation group and the visceral fat accumulation-free group or an accurate evaluation of the visceral fat area state.

According to the visceral fat accumulation-evaluating system, the multivariate discriminant may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be formula 1, formula 2, the logistic regression equation with Ser, Glu, Ile, Tyr, and Arg as the explanatory variables, the logistic regression equation with Ser, Glu, Leu, and Trp as the explanatory variables, formula 3, or formula 4. Thus, the discriminant values obtained in the multivariate discriminants useful particularly for discriminating between the 2 groups of the visceral fat accumulation group and the visceral fat accumulation-free group or evaluating the visceral fat area state can be utilized to bring about an effect of enabling a more accurate discrimination between the 2 groups of the visceral fat accumulation group and the visceral fat accumulation-free group or a more accurate evaluation of the visceral fat area state.

$$(\text{Glu}+\text{Tyr}+\text{Orn})/(\text{Asn}+\text{Ser}) \qquad (\text{formula 1})$$

$$(\text{Glu}+\text{Leu})/(\text{Ser}+\text{Tau})+(\text{Pro}+\text{Orn})/(\text{Gln}) \qquad (\text{formula 2})$$

$$(\text{Glu}+\text{Gly})+(-0.2)\times(\text{Ser}/\text{Tyr})+(-0.1)\times(\text{His}/\text{Trp}) \qquad (\text{formula 3})$$

$$(\text{Glu}/\text{Gly})+(-0.54)\times(\text{Ser}/\text{Leu})+(0.15)\times(\text{Pro}/\text{Trp})+(-0.05)\times(\text{Gln}/\text{Tyr}) \qquad (\text{formula 4})$$

The multivariate discriminants described above can be prepared by a method described in International Publication WO 2004/052191 that is an international application filed by the present applicant or by a method (multivariate discriminant-preparing processing described later) described in International Publication WO 2006/098192 that is an international application filed by the present applicant. Any multivariate discriminants obtained by these methods can be preferably used in the evaluation of the visceral fat accumulation, regardless of the unit of the amino acid concentration in the amino acid concentration data as input data.

In addition to the second embodiment described above, the visceral fat accumulation-evaluating apparatus, the visceral fat accumulation-evaluating method, the visceral fat accumulation-evaluating system, the visceral fat accumulation-evaluating program product and the recording medium according to the present invention can be practiced in various different embodiments within the technological scope of the claims. For example, among the processings described in the second embodiment above, all or a part of the processings described above as performed automatically may be performed manually, and all or a part of the manually conducted processings may be performed automatically by known methods. In addition, the processing procedure, control procedure, specific name, various registered data, information including parameters such as retrieval condition, screen, and database configuration shown in the description above or drawings may be modified arbitrarily, unless specified otherwise. For example, the components of the visceral fat accumulation-evaluating apparatus 100 shown in the figures are conceptual and functional and may not be the same physically as those shown in the figure. In addition, all or an arbitrary part of the operational function of each component and each device in the visceral fat accumulation-evaluating apparatus 100 (in particular, the operational functions executed in the control device 102) may be executed by the CPU (Central Processing Unit) or the programs executed by the CPU, and may be realized as wired-logic hardware.

The "program" is a data processing method written in any language or by any description method and may be of any format such as source code or binary code. The "program" may be not limited to a program configured singly, and may include a program configured decentrally as a plurality of modules or libraries, and a program to achieve the function together with a different program such as OS (Operating System). The program is stored on a recording medium and read mechanically as needed by the visceral fat accumulation-evaluating apparatus 100. Any well-known configuration or procedure may be used as specific configuration, reading procedure, installation procedure after reading, and the like for reading the programs recorded on the recording medium in each apparatus.

The "recording media" includes any "portable physical media", "fixed physical media", and "communication media". Examples of the "portable physical media" include flexible disk, magnetic optical disk, ROM, EPROM (Erasable Programmable Read Only Memory), EEPROM (Electronically Erasable and Programmable Read Only Memory), CD-ROM (Compact Disk Read Only Memory), MO (Magneto-Optical disk), DVD (Digital Versatile Disk), and the like. Examples of the "fixed physical media" include ROM, RAM, HD, and the like which are installed in various computer systems. The "communication media" for example stores the program for a short period of time such as communication line and carrier wave when the program is transmitted via a network such as LAN (Local Area Network), WAN (Wide Area Network), or the Internet.

Figure 22:
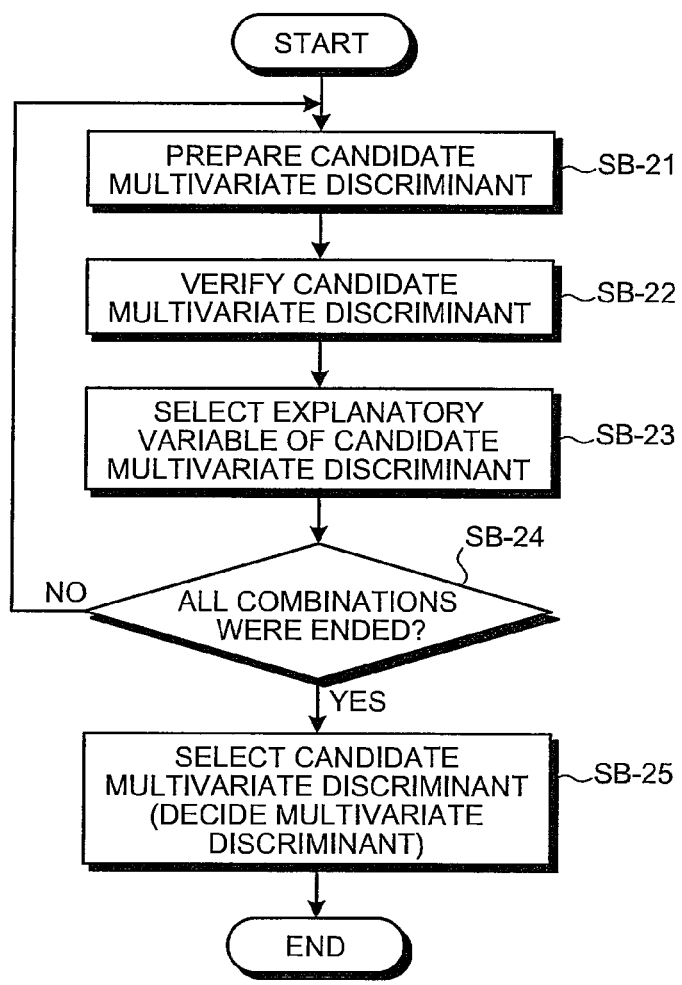
FIG. 22 is a flowchart showing an example of a multivariate discriminant-preparing processing performed in the visceral fat accumulation-evaluating apparatus 100 in the present system.

Finally, an example of the multivariate discriminant-preparing processing performed in the visceral fat accumulation-evaluating apparatus 100 is described in detail with reference to FIG. 22. FIG. 22 is a flowchart showing an example of the multivariate discriminant-preparing processing. The multivariate discriminant-preparing processing may be performed in the database apparatus 400 handling the visceral fat accumulation condition information.

In the present description, the visceral fat accumulation-evaluating apparatus 100 stores the visceral fat accumulation condition information previously obtained from the database apparatus 400 in a predetermined memory region of the visceral fat accumulation condition information file 106c. The visceral fat accumulation-evaluating apparatus 100 shall store, in a predetermined memory region of the designated visceral fat accumulation condition information file 106d, the visceral fat accumulation condition information including the visceral fat accumulation condition index data and amino acid concentration data designated previously in the visceral fat accumulation condition information-designating part 102g.

The candidate multivariate discriminant-preparing part 102h1 in the multivariate discriminant-preparing part 102h first prepares the candidate multivariate discriminant according to a predetermined discriminant-preparing method from the visceral fat accumulation condition information stored in a predetermine memory region of the designated visceral fat accumulation condition information file 106d, and stores the prepared candidate multivariate discriminate in a predetermined memory region of the candidate multivariate discriminant file 106e1 (step SB-21). Specifically, the candidate multivariate discriminant-preparing part 102h1 in the multivariate discriminant-preparing part 102h first selects a desired method out of a plurality of different discriminant-preparing methods (including those for multivariate analysis such as principal component analysis, discriminant analysis, support vector machine, multiple regression analysis, logistic regression analysis, k-means method, cluster analysis, and decision tree) and determines the form of the candidate multivariate discriminant to be prepared based on the selected discriminant-preparing method. The candidate multivariate discriminant-preparing part 102h1 in the multivariate discriminant-preparing part 102h then performs various calculation corresponding to the selected function-selecting method (e.g., average or variance), based on the visceral fat accumulation condition information. The candidate multivariate discriminant-preparing part 102h1 in the multivariate discriminant-preparing part 102h then determines the parameters for the calculation result and the determined candidate multivariate discriminant. In this way, the candidate multivariate discriminant is generated based on the selected discriminant-preparing method. When candidate multivariate discriminants are generated simultaneously and concurrently (in parallel) by using a plurality of different discriminant-preparing methods in combination, the processings described above may be executed concurrently for each selected discriminant-preparing method. Alternatively when candidate multivariate discriminants are generated in series by using a plurality of different discriminant-preparing methods in combination, for example, candidate multivariate discriminants may be generated by converting the visceral fat accumulation condition information with the candidate multivariate discriminant prepared by performing principal component analysis and performing discriminant analysis of the converted visceral fat accumulation condition information.

The candidate multivariate discriminant-verifying part 102h2 in the multivariate discriminant-preparing part 102h verifies (mutually verifies) the candidate multivariate discriminant prepared in the step SB-21 according to a predetermined verifying method and stores the verification result in a predetermined memory region of the verification result file 106e2 (step SB-22). Specifically, the candidate multivariate discriminant-verifying part 102h2 in the multivariate discriminant-preparing part 102h first generates the verification data to be used in verification of the candidate multivariate discriminant, based on the visceral fat accumulation condition information stored in a predetermined memory region of the designated visceral fat accumulation condition information file 106*d*, and verifies the candidate multivariate discriminant according to the generated verification data. If a plurality of candidate multivariate discriminants are generated by using a plurality of different discriminant-preparing methods in the step SB-21, the candidate multivariate discriminant-verifying part 102*h*2 in the multivariate discriminant-preparing part 102*h* verifies each candidate multivariate discriminant corresponding to each discriminant-preparing method according to a predetermined verifying method. Here in the step SB-22, at least one of the discrimination rate, sensitivity, specificity, information criterion, and the like of the candidate multivariate discriminant may be verified based on at least one of the bootstrap method, holdout method, leave-one-out method, and the like. Thus, it is possible to select the candidate multivariate discriminant higher in predictability or reliability, by taking the visceral fat accumulation condition information and the diagnostic condition into consideration.

Then, the explanatory variable-selecting part 102*h*3 in the multivariate discriminant-preparing part 102*h* selects the combination of the amino acid concentration data contained in the visceral fat accumulation condition information used in preparing the candidate multivariate discriminant by selecting the explanatory variable of the candidate multivariate discriminant from the verification result obtained in the step SB-22 according to a predetermined explanatory variable-selecting method, and stores the visceral fat accumulation condition information including the selected combination of the amino acid concentration data in a predetermined memory region of the selected visceral fat accumulation condition information file 106*e*3 (step SB-23). When a plurality of candidate multivariate discriminants are generated by using a plurality of different discriminant-preparing methods in the step SB-21 and each candidate multivariate discriminant corresponding to each discriminant-preparing method is verified according to a predetermined verifying method in the step SB-22, the explanatory variable-selecting part 102*h*3 in the multivariate discriminant-preparing part 102*h* selects the explanatory variable of the candidate multivariate discriminant for each candidate multivariate discriminant corresponding to the verification result obtained in the step SB-22, according to a predetermined explanatory variable-selecting method in the step SB-23. Here in the step SB-23, the explanatory variable of the candidate multivariate discriminant may be selected from the verification results according to at least one of the stepwise method, best path method, local search method, and genetic algorithm. The best path method is a method of selecting an explanatory variable by optimizing an evaluation index of the candidate multivariate discriminant while eliminating the explanatory variables contained in the candidate multivariate discriminant one by one. In the step SB-23, the explanatory variable-selecting part 102*h*3 in the multivariate discriminant-preparing part 102*h* may select the combination of the amino acid concentration data based on the visceral fat accumulation condition information stored in a predetermined memory region of the designated visceral fat accumulation condition information file 106*d*.

The multivariate discriminant-preparing part 102*h* then judges whether all combinations of the amino acid concentration data contained in the visceral fat accumulation condition information stored in a predetermined memory region of the designated visceral fat accumulation condition information file 106*d* are processed, and if the judgment result is "End" (Yes in step SB-24), the processing advances to the next step (step SB-25), and if the judgment result is not "End" (No in step SB-24), it returns to the step SB-21. The multivariate discriminant-preparing part 102*h* judges whether the processing is performed a predetermined number of times, and if the judgment result is "End" (Yes in step SB-24), the processing may advance to the next step (step SB-25), and if the judgment result is not "End" (No in step SB-24), it may return to the step SB-21. The multivariate discriminant-preparing part 102*h* may judge whether the combination of the amino acid concentration data selected in the step SB-23 is the same as the combination of the amino acid concentration data contained in the visceral fat accumulation condition information stored in a predetermined memory region of the designated visceral fat accumulation condition information file 106*d* or the combination of the amino acid concentration data selected in the previous step SB-23, and if the judgment result is "the same" (Yes in step SB-24), the processing may advance to the next step (step SB-25) and if the judgment result is not "the same" (No in step SB-24), it may return to step SB-21. If the verification result is specifically the evaluation value for each multivariate discriminant, the multivariate discriminant-preparing part 102*h* may advance to the step SB-25 or return to the step SB-21, based on the comparison of the evaluation value with a particular threshold corresponding to each discriminant-preparing method.

Then, the multivariate discriminant-preparing part 102*h* determines the multivariate discriminant by selecting the candidate multivariate discriminant used as the multivariate discriminant based on the verification results from a plurality of the candidate multivariate discriminants, and stores the determined multivariate discriminant (the selected candidate multivariate discriminant) in particular memory region of the multivariate discriminant file 106*e*4 (step SB-25). Here, in the step SB-25, for example, there are cases where the optimal multivariate discriminant is selected from the candidate multivariate discriminants prepared in the same discriminant-preparing method or the optimal multivariate discriminant is selected from all candidate multivariate discriminants.

Given the foregoing description, the explanation of the multivariate discriminant-preparing processing is finished.

Third Embodiment 3-1. Outline of the Invention

Figure 23:
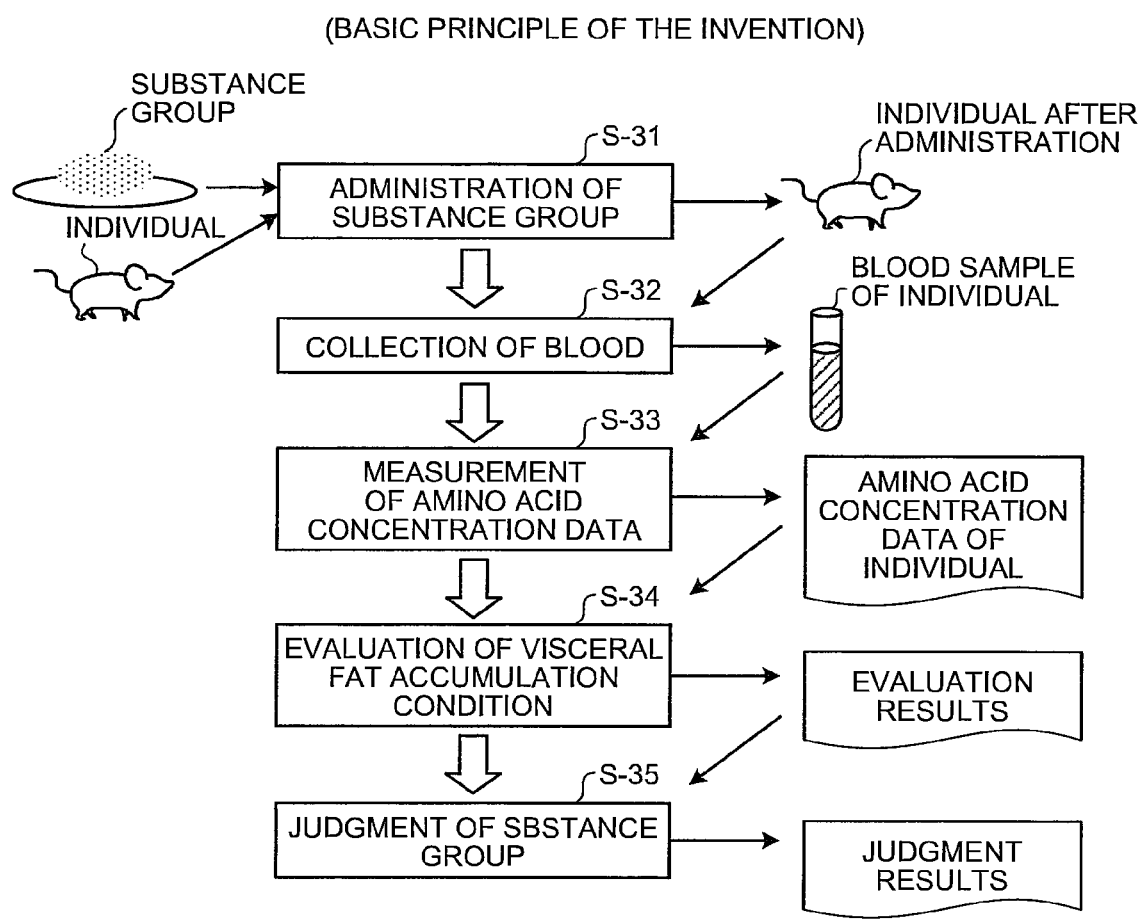
FIG. 23 is a principle configurational diagram showing a basic principle of the present invention.

Herein, the method of searching for prophylactic/ameliorating substance for visceral fat accumulation of the present invention is described in detail with reference to FIG. 23. FIG. 23 is a principle configurational diagram showing a basic principle of the present invention.

First, a desired substance group consisting of one or more substances is administered to a subject to be evaluated (for example, an individual such as an animal or a human) (step S-31). For example, a suitable combination of an existing drug, amino acid, food and supplement capable of administration to humans (for example, a suitable combination of a drug, supplement and anti-obesity drug that are known to be effective in amelioration of various symptoms of visceral fat accumulation) may be administered over a predetermined period (for example in the range of 1 day to 12 months) in a predetermined amount at predetermined frequency and timing (for example 3 times per day, after food) by a predetermined administration method (for example, oral administration). The administration method, dose, and dosage form may be suitably combined depending on the condition of a patient. The dosage form may be determined based on known techniques. The dose is not particularly limited, and for example, a drug containing 1 μg to 100 g active ingredient may be given.

From the subject administered with the substance group in the step S-31, blood is then collected (step S-32).

Amino acid concentration data on concentration values of amino acids are measured from the blood collected in the step S-32 (step S-33). The concentrations of amino acids in blood may be analyzed in the following manner. A blood sample is collected in a heparin-treated tube, and then the blood plasma is separated by centrifugation of the collected blood sample. All blood plasma samples separated are frozen and stored at −70° C. before a measurement of an amino acid concentration. Before the measurement of the amino acid concentration, the blood plasma samples are defrosted, and the defrosted blood plasma samples are deproteinized by adding sulfosalicylic acid to a concentration of 3%. The concentration values of various amino acids are measured by analyzing the deproteinized blood plasma samples by an amino acid analyzer by high-performance liquid chromatography (HPLC) by using ninhydrin reaction in post column.

Then, a visceral fat accumulation condition in the subject is evaluated based on the amino acid concentration data of the subject measured in the step S-33 (step S-34).

Then, whether or not the substance group administered in the step S-31 prevents the visceral fat accumulation or ameliorates the visceral fat accumulation condition is judged based on an evaluation result in the step S-34 (step S-35).

When a judgment result in the step S-35 is "preventive or ameliorative", the substance group administered in the step S-31 is searched as one preventing the visceral fat accumulation or ameliorating the visceral fat accumulation condition.

According to the present invention, (1) the desired substance group is administered to the subject, (2) blood is collected from the subject to which the desired substance group has been administered, (3) the amino acid concentration data on the concentration values of the amino acids is measured, (4) the visceral fat accumulation condition in the subject is evaluated based on the measured amino acid concentration data, and (5) it is judged whether or not the desired substance group prevents the visceral fat accumulation or ameliorates the visceral fat accumulation condition based on the evaluation results. Thus, the method of evaluating visceral fat accumulation capable of accurately evaluating the visceral fat accumulation condition by utilizing the concentrations of the amino acids in blood can be used to bring about an effect of enabling an accurate search for substances for preventing the visceral fat accumulation or ameliorating the visceral fat accumulation condition.

Before the step S-34 is executed, data such as defective and outliers may be removed from the amino acid concentration data. Thereby, the visceral fat accumulation condition can be more accurately evaluated.

In the step S-34, the visceral fat accumulation condition in the subject may be evaluated based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured in the step S-33. Thus, the concentrations of the amino acids which among amino acids in blood, are associated with the visceral fat accumulation condition can be utilized to bring about an effect of enabling an accurate evaluation of the visceral fat accumulation condition.

In the step S-34, a discrimination between a visceral fat accumulation group and a visceral fat accumulation-free group in the subject may be conducted based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured in the step S-33. Specifically, the concentration value of at least one of Val, Leu, Ile, Tyr, Phe, Trp, Glu, Ala, Pro, Orn, Lys, Gly, Ser, Met, Arg, Cys, and Gln may be compared with a previously established threshold (cutoff value), thereby discriminating between the visceral fat accumulation group and the visceral fat accumulation-free group in the subject. Thus, the concentrations of the amino acids which among amino acids in blood, are useful for discriminating between 2 groups of the visceral fat accumulation group and the visceral fat accumulation-free group can be utilized to bring about an effect of enabling an accurate discrimination between the 2 groups of the visceral fat accumulation group and the visceral fat accumulation-free group.

In the step S-34, a visceral fat area stete in the subject that reflects the visceral fat accumulation may be evaluated based on the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured in the step S-33. Specifically, the concentration value of at least one of Val, Leu, Ile, Tyr, Phe, Trp, Glu, Ala, Pro, Orn, Lys, Gly, Ser, Met, Arg, Cys, and Gln may be compared with a previously established threshold (cutoff value), thereby evaluating the visceral fat area state in the subject that reflects the visceral fat accumulation. Thus, the concentrations of the amino acids which among amino acids in blood, are useful for evaluating the visceral fat area state can be utilized to bring about an effect of enabling an accurate evaluation of the visceral fat area state.

In the step S-34, a discriminant value that is a value of a multivariate discriminant with a concentration of the amino acid as an explanatory variable may be calculated based on both the amino acid concentration data of the subject measured in the step S-33 and the previously established multivariate discriminant, and the visceral fat accumulation condition in the subject may be evaluated based on the calculated discriminant value. Thus, the discriminant values obtained in the multivariate discriminants with the concentrations of the amino acids as the explanatory variables can be utilized to bring about an effect of enabling an accurate evaluation of the visceral fat accumulation condition.

In the step S-34, the discriminant value may be calculated based on both the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the subject measured in the step S-33 and the multivariate discriminant containing at least one of Val, Leu, Ile, Tyr, Phe, Trp, Glu, Ala, Pro, Orn, Lys, Gly, Ser, Met, Arg, Cys, and Gln as the explanatory variable, and the visceral fat accumulation condition in the subject may be evaluated based on the calculated discriminant value. Thus, the discriminant values obtained in the multivariate discriminants which are correlated with the visceral fat accumulation condition significantly can be utilized to bring about an effect of enabling an accurate evaluation of the visceral fat accumulation condition.

In the step S-34, the discrimination between the visceral fat accumulation group and the visceral fat accumulation-free group in the subject may be conducted based on the calculated discriminant value. Specifically, the discriminant value may be compared with a previously established threshold (cutoff value), thereby discriminating between the visceral fat accumulation group and the visceral fat accumulation-free group in the subject. Thus, the discriminant values obtained in the multivariate discriminants useful for discriminating between 2 groups of the visceral fat accumulation group and the visceral fat accumulation-free group can be utilized to bring about an effect of enabling an accurate discrimination between the 2 groups of the visceral fat accumulation group and the visceral fat accumulation-free group. The multivariate discriminant may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be formula 1, formula 2, the logistic regression equation with Ser, Glu, Ile, Tyr, and Arg as the explanatory variables, or the logistic regression equation with Ser, Glu, Leu, and Trp as the explanatory variables. Thus, the discriminant values obtained in the multivariate discriminants useful particularly for discriminating between the 2 groups of the visceral fat accumulation group and the visceral fat accumulation-free group can be utilized to bring about an effect of enabling a more accurate discrimination between the 2 groups of the visceral fat accumulation group and the visceral fat accumulation-free group.

(Glu+Tyr+Orn)/(Asn+Ser)  (formula 1)

(Glu+Leu)/(Ser+Tau)+(Pro+Orn)/(Gln)  (formula 2)

In the step S-34, the visceral fat area stete in the subject that reflects the visceral fat accumulation may be evaluated based on the calculated discriminant value. Specifically, the discriminant value may be compared with a previously established threshold (cutoff value), thereby evaluating the visceral fat area state in the subject that reflects the visceral fat accumulation. Thus, the discriminant values obtained in the multivariate discriminants useful for evaluating the visceral fat area state can be utilized to bring about an effect of enabling an accurate evaluation of the visceral fat area state. The multivariate discriminant may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be formula 3 or formula 4. Thus, the discriminant values obtained in the multivariate discriminants useful particularly for evaluating the visceral fat area state can be utilized to bring about an effect of enabling a more accurate evaluation of the visceral fat area state.

(Glu+Gly)+(−0.2)×(Ser/Tyr)+(−0.1)×(His/Trp)  (formula 3)

(Glu/Gly)+(−0.54)×(Ser/Leu)+(0.15)×(Pro/Trp)+(−0.05)×(Gln/Tyr)  (formula 4)

The multivariate discriminants described above can be prepared by a method described in International Publication WO 2004/052191 that is an international application filed by the present applicant or by a method (multivariate discriminant-preparing processing described in the second embodiment described later) described in International Publication WO 2006/098192 that is an international application filed by the present applicant. Any multivariate discriminants obtained by these methods can be preferably used in the evaluation of the visceral fat accumulation condition, regardless of the unit of the amino acid concentration in the amino acid concentration data as input data.

In the fractional expression, the numerator of the fractional expression is expressed by the sum of the amino acids A, B, C etc. and the denominator of the fractional expression is expressed by the sum of the amino acids a, b, c etc. The fractional expression also includes the sum of the fractional expressions α, β, γ etc. (for example, α+β) having such constitution. The fractional expression also includes divided fractional expressions. The amino acids used in the numerator or denominator may have suitable coefficients respectively. The amino acids used in the numerator or denominator may appear repeatedly. Each fractional expression may have a suitable coefficient. A value of a coefficient for each explanatory variable and a value for a constant term may be any real numbers.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each explanatory variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

When the visceral fat accumulation condition is evaluated (specifically, the discrimination between the visceral fat accumulation group and the visceral fat accumulation-free group is conducted, the visceral fat area state is evaluated) in the present invention, concentrations of other metabolites (biological metabolites), protein expression level, age and sex of the subject, biological indices or the like may be used in addition to the concentrations of the amino acids. When the visceral fat accumulation condition is evaluated (specifically, the discrimination between the visceral fat accumulation group and the visceral fat accumulation-free group is conducted, the visceral fat area state is evaluated) in the present invention, concentrations of other metabolites (biological metabolites), protein expression level, age and sex of the subject, biological indices or the like may be used as the explanatory variables in the multivariate discriminants in addition to the concentrations of the amino acids.

Figure 24:
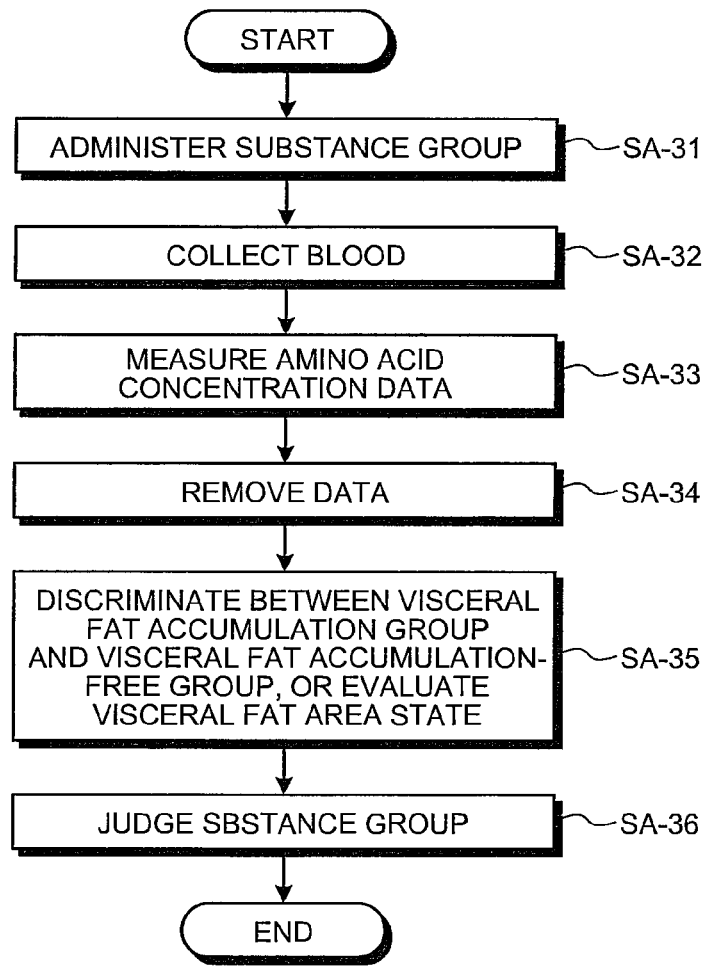
FIG. 24 is a flowchart showing one example of a method of searching for prophylactic/ameliorating substance for visceral fat accumulation according to a third embodiment.

3-2. An Example of the Method of Searching for Prophylactic/Ameliorating Substance for Visceral Fat Accumulation According to the Third Embodiment Here, an example of the method of searching for prophylactic/ameliorating substance for visceral fat accumulation according to the third embodiment is described with reference to FIG. 24. FIG. 24 is a flowchart showing an example of the method of searching for prophylactic/ameliorating substance for visceral fat accumulation according to the third embodiment.

First, a desired substance group consisting of one or more substances is administered to an individual such as an animal or a human with an excess of the visceral fat accumulation (step SA-31).

From the individual administered with the substance group in the step S-31, blood is then collected (step SA-32).

From the blood collected in the step S-32, the amino acid concentration data on the concentration values of the amino acids are measured (step SA-33). The measurement of the concentration values of the amino acids is conducted by the method described above.

From the amino acid concentration data of the individual measured in the step S-33, data such as defective and outliers is then removed (step SA-34).

Then, the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the individual from which the data such as the defective and outliers was removed in the step SA-34 is compared with a previously established threshold (cutoff value), thereby discriminating between the visceral fat accumulation group and the visceral fat accumulation-free group or evaluating the visceral fat area state in the individual (step SA-35).

Based on the discrimination results or evaluation results in the step SA-35, it is then judged whether or not the substance group administered in the step SA-31 prevents the visceral fat accumulation or ameliorates the visceral fat accumulation condition (step SA-36).

When the judgment result obtained in the step SA-36 is "preventive or ameliorative", the substance group administered in the step SA-31 is searched as one preventing the visceral fat accumulation or ameliorating the visceral fat accumulation condition. The substances searched by the searching method of the present embodiment include, for example, an amino acid group of Val, Leu, Ile, Tyr, Phe, Trp, Glu, Ala, Pro, Orn, Lys, Gly, Ser, Met, Arg, Cys, and Gln.

3-3. Summary of the Third Embodiment and Other Embodiments

According to the method of searching for prophylactic/ameliorating substance for visceral fat accumulation according to the third embodiment described in detail above, (1) the desired substance group is administered to the individual, (2) the blood is collected from the individual administered with the substance group in (1), (3) the amino acid concentration data are measured from the blood collected in (2), (4) the data such as the defective and outliers is removed from the measured amino acid concentration data of the individual, (5) the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the individual from which the data such as the defective and outliers was removed is compared with the previously established threshold (cutoff value), thereby discriminating between the visceral fat accumulation group and the visceral fat accumulation-free group or evaluating the visceral fat area state in the individual, and (6) based on the discrimination result or evaluation result in (5), it is judged whether or not the substance group administered in (1) prevents the visceral fat accumulation or ameliorates the visceral fat accumulation condition. Thus, the method of evaluating visceral fat accumulation of the first embodiment described above capable of accurately evaluating the visceral fat accumulation condition by utilizing the concentrations of the amino acids in blood can be used to bring about an effect of enabling an accurate search for the substance for preventing the visceral fat accumulation or ameliorating the visceral fat accumulation condition.

In the step SA-35, the discriminant value may be calculated based on both the concentration value of at least one of Val, Leu, Ile, Tyr, Phe, Trp, Glu, Ala, Pro, Orn, Lys, Gly, Ser, Met, Arg, Cys, and Gln contained in the amino acid concentration data of the individual from which the data such as the defective and outliers was removed in the step SA-34 and the multivariate discriminant containing at least one of Val, Leu, Ile, Tyr, Phe, Trp, Glu, Ala, Pro, Orn, Lys, Gly, Ser, Met, Arg, Cys, and Gln as the explanatory variable, and the calculated discriminant value may be compared with the previously established threshold (cutoff value), thereby discriminating between the visceral fat accumulation group and the visceral fat accumulation-free group or evaluating the visceral fat area state in the individual. Thus, the discriminant values obtained in the multivariate discriminants useful for discriminating between the 2 groups of the visceral fat accumulation group and the visceral fat accumulation-free group or for evaluating the visceral fat area state can be utilized to bring about an effect of enabling an accurate discrimination between the 2 groups of the visceral fat accumulation group and the visceral fat accumulation-free group or an accurate evaluation of the visceral fat area state.

In the step SA-35, the multivariate discriminant may be expressed by one fractional expression or the sum of a plurality of the fractional expressions and may contain at least one of Val, Leu, Ile, Tyr, Phe, Trp, Glu, Ala, Pro, Orn, Lys, Gly, Ser, Met, Arg, Cys, and Gln as the explanatory variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Specially, the multivariate discriminant may be formula 1, formula 2, the logistic regression equation with Ser, Glu, Ile, Tyr, and Arg as the explanatory variables, or the logistic regression equation with Ser, Glu, Leu, and Trp as the explanatory variables. Thus, the discriminant values obtained in the multivariate discriminants useful particularly for discriminating between the 2 groups of the visceral fat accumulation group and the visceral fat accumulation-free group can be utilized to bring about an effect of enabling a more accurate discrimination between the 2 groups of the visceral fat accumulation group and the visceral fat accumulation-free group.

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2)}$$

Specially, the multivariate discriminant may be formula 3 or formula 4. Thus, the discriminant values obtained in the multivariate discriminants useful particularly for evaluating the visceral fat area state can be utilized to bring about an effect of enabling a more accurate evaluation of the visceral fat area state.

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4)}$$

The multivariate discriminants described above can be prepared by a method described in International Publication WO 2004/052191 that is an international application filed by the present applicant or by a method (multivariate discriminant-preparing processing described in the second embodiment described above) described in International Publication WO 2006/098192 that is an international application filed by the present applicant. Any multivariate discriminants obtained by these methods can be preferably used in the evaluation of the visceral fat accumulation condition, regardless of the unit of the amino acid concentration in the amino acid concentration data as input data.

In the method of searching for prophylactic/ameliorating substance for visceral fat accumulation according to the third embodiment, a substance that restores normal values to the concentration values of the amino acid group containing at least one of Val, Leu, Ile, Tyr, Phe, Trp, Glu, Ala, Pro, Orn, Lys, Gly, Ser, Met, Arg, Cys, and Gln or the discriminant values of each of the multivariate discriminants, can be selected by the method of visceral fat accumulation in the first embodiment or by the visceral fat accumulation-evaluating apparatus in the second embodiment.

In the method of searching for prophylactic/ameliorating substance for visceral fat accumulation in the third embodiment, "searching for prophylactic/ameliorating substance" includes not only discovery of a novel substance effective in preventing and ameliorating the visceral fat accumulation, but also (1) new discovery of use of a known substance in preventing and ameliorating the visceral fat accumulation, (2) discovery of a novel composition consisting of a combination of existing drugs and supplements having efficacy expectable for prevention and amelioration of the visceral fat accumulation, (3) discovery of the suitable usage, dose and combination described above to form them into a kit, (4) presentation of a prophylactic and therapeutic menu including a diet, exercise etc., and (5) presentation of a necessary change in menu for each individual by monitoring the effect of the prophylactic and therapeutic menu.

EXAMPLE 1

Figure 25:
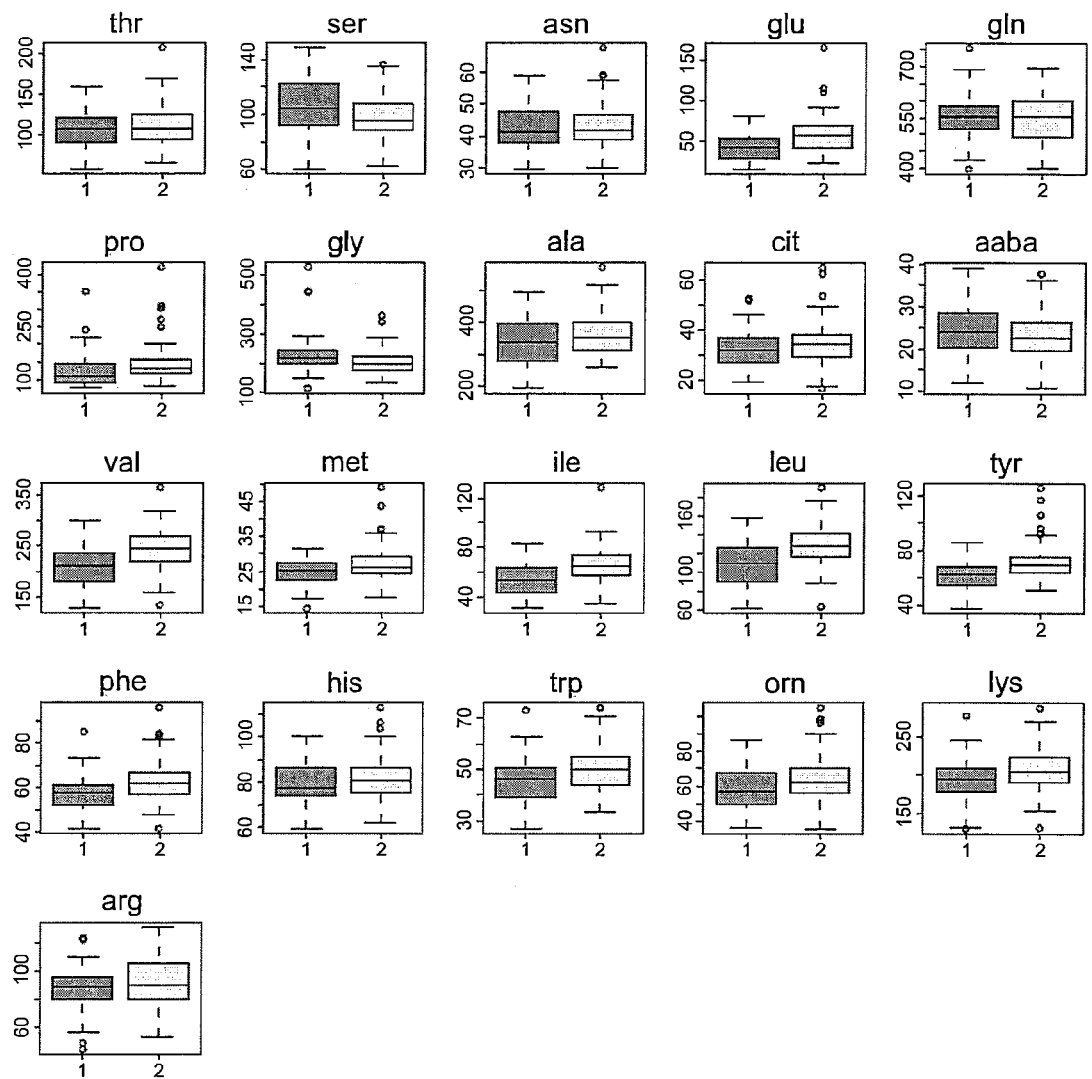
FIG. 25 is a boxplot showing a distribution of amino acid explanatory variables between 2 groups of a visceral fat accumulation group and a visceral fat accumulation-free group.

Based on the previously mentioned joint diagnostic criteria of the Japanese Society of Internal Medicine-associated eight academic societies, 154 examinees of a comprehensive medical examination were divided into the visceral fat accumulation-free group (59 examinees) and the visceral fat accumulation group (95 examinees). From each of the blood samples collected from the examinees, the blood amino acid concentrations were measured by the amino acid analysis method described above. In FIG. 25, boxplots showing a distribution of the amino acid explanatory variables between the 2 groups of the visceral fat accumulation group and the visceral fat accumulation-free group are represented. The numeral reference "1" indicated in the horizontal axis of the boxplot represents the visceral fat accumulation-free group, while the numeral reference "2" represents the visceral fat accumulation group. For the purpose of discrimination between the 2 groups, a Mann-Whitney test was carried out between the 2 groups. The abbreviation "aaba" in the figure represents α-ABA (aminobutyric acid)). The abbreviation "Cys" represents cystine.

In the visceral fat accumulation group as compared with the visceral fat accumulation-free group, Val, Leu, Ile, Tyr, Phe, Trp, Glu, Pro, Lys and Met (significant difference probability $P<0.01$), and Ala and Orn (significant difference probability $P<0.05$) were significantly increased, and Gly and Ser (significant difference probability $P<0.01$) were significantly decreased. It became clear that the amino acid explanatory variables Val, Leu, Ile, Tyr, Phe, Trp, Glu, Ala, Pro, Orn, Lys, Gly, Ser and Met have an ability for discrimination between the 2 groups of the visceral fat accumulation-free group and the visceral fat accumulation group.

EXAMPLE 2

The correlation coefficient (Pearson's correlation coefficient) between the visceral fat area value and each of the blood amino acid concentrations was determined for the 154 examinees of the comprehensive medical examination mentioned in Example 1.

The blood amino acids that exhibited a significant correlation with the visceral fat area value include Val ($r=0.41$), Leu ($r=0.37$), Ile ($r=0.42$), Tyr ($r=0.39$), Trp ($r=0.32$), Glu ($r=0.48$), Ala ($r=0.24$), Pro ($r=0.19$), Lys ($r=0.17$), Gly ($r$—$0.28$), Ser ($r=-0.20$), Met ($r=0.21$), and Arg ($r=0.16$). It became clear that the amino acid explanatory variables Val, Leu, Ile, Tyr, Trp, Glu, Ala, Pro, Lys, Gly, Ser, Met and Arg have a capability for diagnosis of the visceral fat area state.

EXAMPLE 3

The sample data used in Example 1 were used. An index formula that maximizes a performance of a discrimination between the 2 groups of the visceral fat accumulation group and the visceral fat accumulation-free group, was searched devotedly using a method described in International Publication WO 2004/052191 which is an international application filed by the present applicant. An index formula 1 was obtained among a plurality of index formulae having equivalent performances.

Index formula 1: $(Glu+Tyr+Orn)/(Asn+Ser)$

Figure 26:
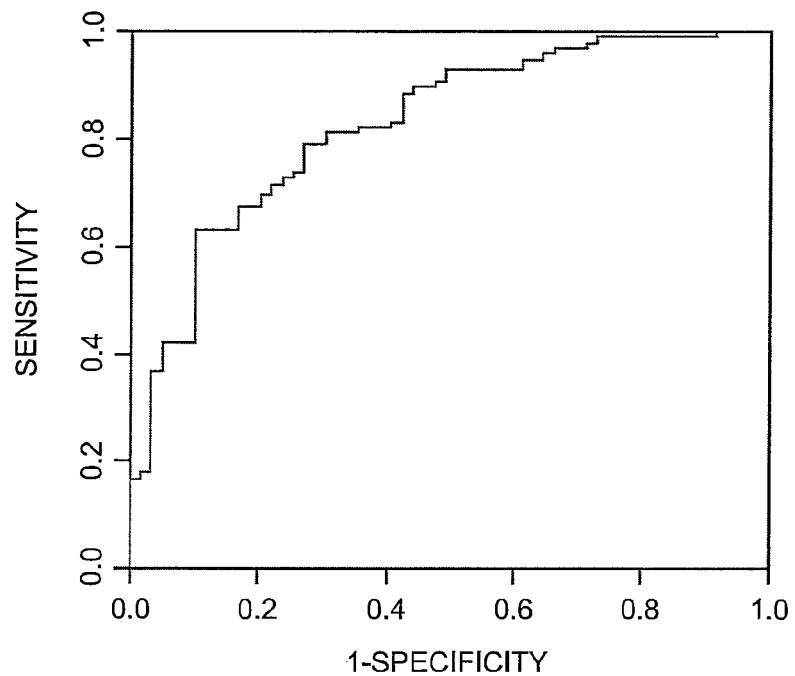
FIG. 26 is a graph showing an ROC curve for an evaluation of a discriminatory performance between 2 groups.

In regard to the performance of the index formula 1 on the discrimination between the 2 groups of the visceral fat accumulation group and the visceral fat accumulation-free group, an evaluation using the AUC (area under the curve) of the ROC (receiver operating characteristic) curve (FIG. 26) was performed to obtain an AUC of $0.832\pm0.036$ (95% confidence interval was 0.753 to 0.897). It became clear that the index formula 1 is a useful index having high diagnostic performance.

EXAMPLE 4

The sample data used in Example 1 were used. An index formula that maximizes a diagnostic performance of the visceral fat area state reflecting the visceral fat accumulation, was searched devotedly using a method described in International Publication WO 2004/052191 which is an international application filed by the present applicant. An index formula 2 was obtained among a plurality of index formulae having equivalent performances.

Index formula 2: $(Glu+Gly)+(-0.2)\times(Ser/Tyr)+(-0.1)\times(His/Trp)$

EXAMPLE 5

The sample data used in Example 1 were used. An index formula that maximizes a performance of a discrimination between the 2 groups of the visceral fat accumulation group and the visceral fat accumulation-free group, was searched devotedly using a method (method of searching for a multivariate discriminant) described in International Publication WO 2006/098192 which is an international application filed by the present applicant. An index formula 3 was obtained among a plurality of index formulae having equivalent performances. In the index formula 3, the numerical coefficients and constant terms of the amino acid explanatory variables Ser, Glu, Ile, Tyr and Arg are $-0.045\pm0.013$, $0.042\pm0.014$, $0.044\pm0.020$, $0.036\pm0.022$, $0.020\pm0.014$, and $-3.912\pm1.947$ in the same order. A multivariate discriminant can be prepared by using a linear discriminant, a support vector machine, a Mahalanobis' generalized distance method or the like, in addition to a logistic regression, as the method of searching the multivariate discriminant.

Figure 27:
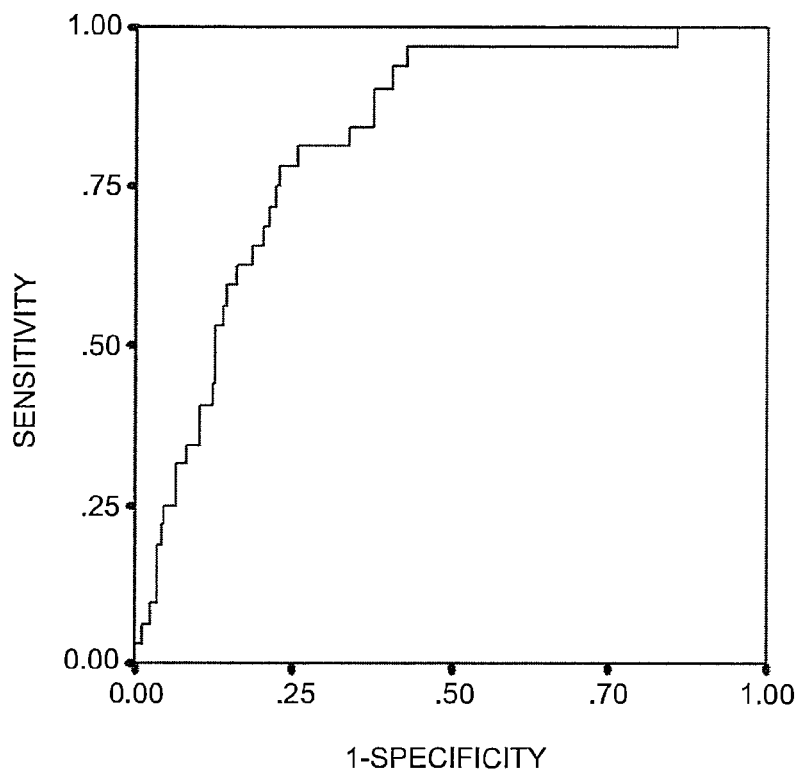
FIG. 27 is a graph showing an ROC curve for an evaluation of a discriminatory performance between 2 groups.

Index formula 3: A logistic regression equation composed of Ser, Glu, Ile, Tyr and Arg In regard to the performance of the index formula 3 on the discrimination between the 2 groups of the visceral fat accumulation group and the visceral fat accumulation-free group, an evaluation using the AUC of the ROC curve (FIG. 27) was performed to obtain an AUC of $0.839\pm0.034$ (95% confidence interval was 0.772 to 0.906). It became clear that the index formula 3 is a useful index having high diagnostic performance.

Using the same data mentioned above, multivariate discriminants prepared by a linear discriminant, a support vector machine method and a Mahalanobis' generalized distance method, were evaluated as other examples of the index formula 3 composed of Ser, Glu, Ile, Tyr and Arg. In the linear discriminant, an AUC of the ROC curve of $0.836\pm0.036$ (95% confidence interval was 0.766 to 0.906) was obtained; in the support vector machine method, an error rate of 17.9% was obtained; and in the Mahalanobis' generalized distance method, an error rate of 22.3% was obtained. It became clear that these multivariate discriminants are useful indices having high diagnostic performances, similarly to the index formula 3.

EXAMPLE 6

The sample data used in Example 1 were used. An index that maximizes a performance of a discrimination between the 2 groups of the visceral fat accumulation-free group and the visceral fat accumulation group, was searched devotedly using a method described in International Publication WO 2004/052191 which is an international application filed by the present applicant. A plurality of index formulae having performances that are equivalent to that of the index formula 1, were obtained (FIG. 28). In FIG. 28, a list of the AUCs of the ROC curves corresponding to the respective index formulae is represented. The abbreviation "aaba" in the figure represents α-ABA (aminobutyric acid). In FIG. 29, the sensitivity, specificity, positive predictive value, negative predictive value and discrimination rate for the respective cutoff values of the index formula 1 are represented.

EXAMPLE 7

Figure 30:
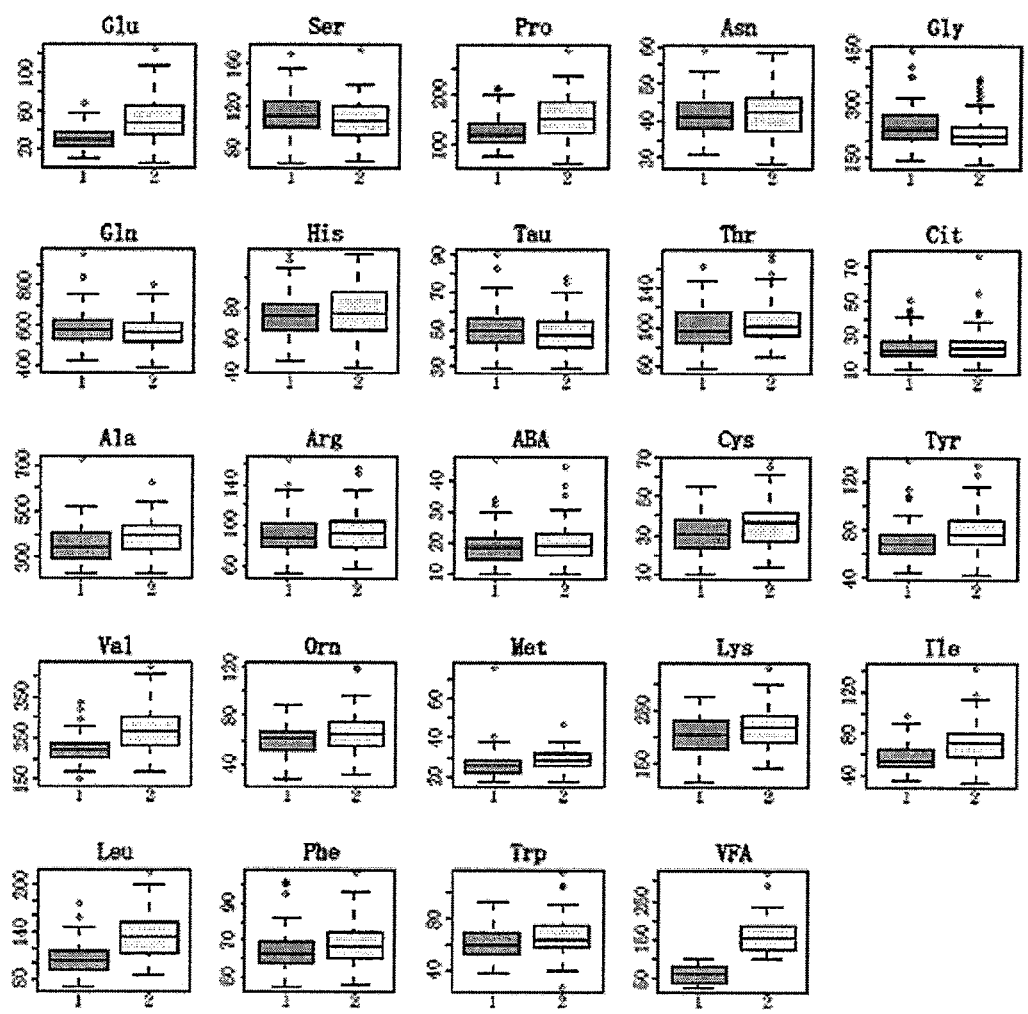
FIG. 30 is a boxplot showing a distribution of amino acid explanatory variables between 2 groups of a visceral fat accumulation group and a visceral fat accumulation-free group.

Based on the previously mentioned joint diagnostic criteria of the Japanese Society of Internal Medicine-associated eight academic societies, 201 examinees of a comprehensive medical examination were divided into the visceral fat accumulation-free group (72 examinees) and the visceral fat accumulation group (129 examinees). From each of the blood samples collected from the examinees, the blood amino acid concentrations were measured by the amino acid analysis method described above. In FIG. 30, boxplots showing a distribution of the amino acid explanatory variables between the 2 groups of the visceral fat accumulation-free group and the visceral fat accumulation group are represented. The numeral reference "1" indicated in the horizontal axis of the boxplot represents the visceral fat accumulation-free group, while the numeral reference "2" represents the visceral fat accumulation group. For the purpose of discrimination between the 2 groups, a Mann-Whitney test was carried out between the 2 groups. The abbreviation "ABA" represents α-ABA, and the abbreviation "Cys" represents cystine. The abbreviation "VFA" represents volatile fatty acid.

In the visceral fat accumulation group as compared with the visceral fat accumulation-free group, Glu, Pro, Ala, Tyr, Val, Ile and Leu (significant difference probability $P<0.001$), Orn, Met, Phe and Trp (significant difference probability $P<0.01$), and Cys and Lys (significant difference probability $P<0.05$) were significantly increased, and Gly (probability of significant difference $P<0.001$) was significantly decreased. It became clear that the amino acid explanatory variables Glu, Pro, Ala, Tyr, Val, Ile, Leu, Orn, Met, Phe, Trp, Cys, Lys and Gly have an ability for discrimination between the 2 groups of the visceral fat accumulation-free group and the visceral fat accumulation group.

EXAMPLE 8

The correlation coefficient (Pearson's correlation coefficient) between the visceral fat area value and each of the blood amino acid concentrations was determined for the 201 examinees of the comprehensive medical examination mentioned in Example 7.

The blood amino acids that exhibited a significant correlation with the visceral fat area value include Leu ($r=0.53$), Glu ($r=0.52$), Ile ($r=0.52$), Val ($r=0.49$), Pro ($r=0.41$), Gly ($r=-0.37$), Ala ($r=0.34$), Tyr ($r=0.34$), Phe ($r=0.28$), Cys ($r=0.25$), Orn ($r=0.21$), Lys ($r=0.20$), Trp ($r=0.19$), Gln ($r=-0.17$), Ser ($r=-0.17$), and Met ($r=0.17$). It became clear that the amino acid explanatory variables Leu, Glu, Ile, Val, Pro, Gly, Ala, Tyr, Phe, Cys, Orn, Lys, Trp, Gln, Ser and Met have an ability for diagnosis of the visceral fat area state.

EXAMPLE 9

The sample data used in Example 7 were used. An index formula that maximizes a performance of a discrimination between the 2 groups of the visceral fat accumulation group and the visceral fat accumulation-free group, was searched devotedly using a method described in International Publication WO 2004/052191 which is an international application filed by the present applicant. An index formula 4 was obtained among a plurality of index formulae having equivalent performances.

Index formula 4: (Glu+Leu)/(Ser+Tau)+(Pro+Orn)/(Gln)

Figure 31:
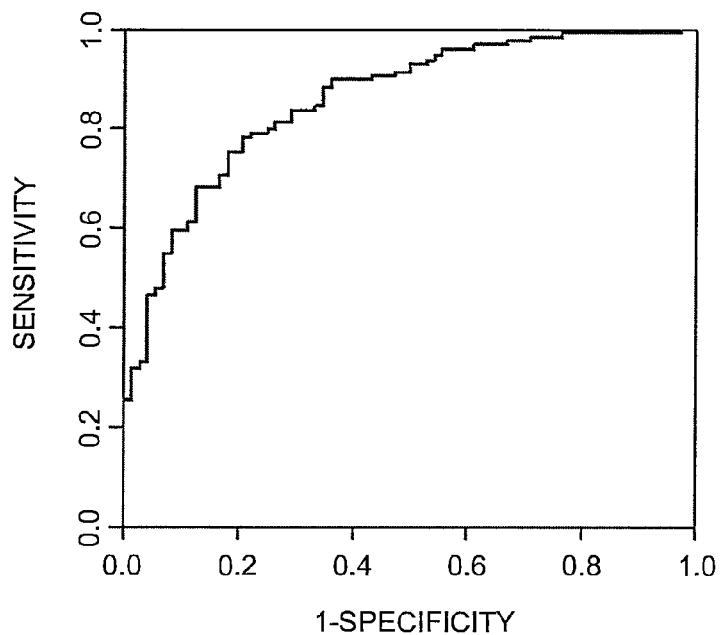
FIG. 31 is a graph showing an ROC curve for an evaluation of a discriminatory performance between 2 groups.

In regard to the performance of the index formula 4 on the discrimination between the 2 groups of the visceral fat accumulation group and the visceral fat accumulation-free group, an evaluation using the AUC of the ROC curve (FIG. 31) was performed to obtain an AUC of $0.858\pm0.030$ (95% confidence interval was 0.799 to 0.917). It became clear that the index formula 4 is a useful index having high diagnostic performance.

EXAMPLE 10

The sample data used in Example 7 were used. An index formula that maximizes a diagnostic performance of the visceral fat area state reflecting the visceral fat accumulation, was searched devotedly using a method described in International Publication WO 2004/052191 which is an international application filed by the present applicant. An index formula 5 was obtained among a plurality of index formulae having equivalent performances.

Index formula 5: (Glu/Gly)+(−0.54)×(Ser/Leu)+(0.15)×(Pro/Trp)+(−0.05)×(Gln/Tyr)

EXAMPLE 11

The sample data used in Example 7 were used. An index formula that maximizes a performance of a discrimination between the 2 groups of the visceral fat accumulation group and the visceral fat accumulation-free group, was searched devotedly using a method (method of searching for a multivariate discriminant) described in International Publication WO 2006/098192 which is an international application filed by the present applicant. An index formula 6 was obtained among a plurality of index formulae having equivalent performances. In the index formula 6, the numerical coefficients and constant terms of the amino acid explanatory variables Ser, Glu, Leu and Trp are −0.022±0.011, 0.064±0.013, 0.063±0.012, −0.059±0.021, and −3.177±1.607 in the same order. A multivariate discriminant can be prepared by using a linear discriminant, a support vector machine, a Mahalanobis' generalized distance method or the like, in addition to a logistic regression, as the method of searching the multivariate discriminant.

Figure 32:
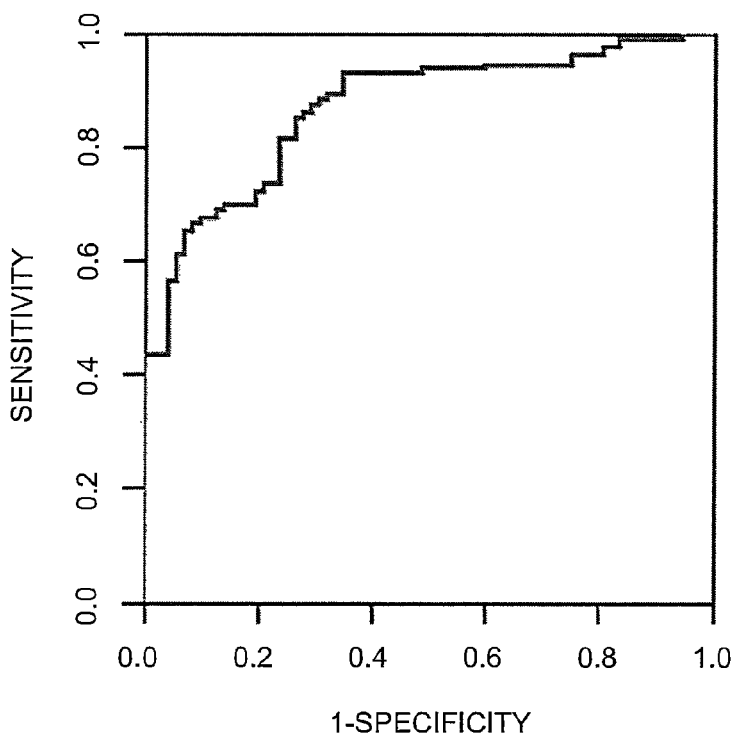
FIG. 32 is a graph showing an ROC curve for an evaluation of a discriminatory performance between 2 groups.

Index formula 6: A logistic regression equation composed of Ser, Glu, Leu and Trp In regard to the performance of the index formula 6 on the discrimination between the 2 groups of the visceral fat accumulation group and the visceral fat accumulation-free group, an evaluation using the AUC of the ROC curve (FIG. 32) was performed to obtain an AUC of 0.870±0.025 (95% confidence interval was 0.821 to 0.919). It became clear that the index formula 6 is a useful index having high diagnostic performance.

Using the same data mentioned above, multivariate discriminants prepared by a linear discriminant, a support vector machine method and a Mahalanobis' generalized distance method, were evaluated as other examples of the index formula 6 composed of Ser, Glu, Leu and Trp. In the linear discriminant, an AUC of the ROC curve of 0.885±0.027 (95% confidence interval was 0.831 to 0.939) was obtained; in the support vector machine method, an error rate of 23.1% was obtained; and in the Mahalanobis' generalized distance method, an error rate of 23.0% was obtained. It became clear that these multivariate discriminants are useful indices having high diagnostic performances, similarly to the index formula 6.

EXAMPLE 12

The sample data used in Example 7 were used. An index that maximizes a performance of a discrimination between the 2 groups of the visceral fat accumulation-free group and the visceral fat accumulation group, was searched devotedly using a method described in International Publication WO 2004/052191 which is an international application filed by the present applicant. A plurality of index formulae having performances that are equivalent to that of the index formula 4, were obtained (FIGS. 33 to 35). In FIGS. 33 to 35, lists of the AUCs of the ROC curves corresponding to the respective index formulae are represented. The abbreviation "ABA" represents α-ABA, and the abbreviation "Cys" represents cystine. In FIG. 36, the sensitivity, specificity, positive predictive value, negative predictive value and discrimination rate for the respective cutoff values of the index formula 4 are represented.

EXAMPLE 13

The sample data used in Example 7 were used. An index formula that maximizes a diagnostic performance of the visceral fat area state reflecting the visceral fat accumulation, was searched devotedly using a method (method of searching for a multivariate discriminant) described in International Publication WO 2006/098192 which is an international application filed by the present applicant. A plurality of linear regression equations having diagnostic performances that are equivalent to that of the index formula 5, were obtained. Those expressions are represented in FIGS. 37 and 38. The values of the respective coefficients in the equations shown in FIGS. 37 and 38 may be values multiplied by a real number, or values obtained by addition of an arbitrary real constant.

EXAMPLE 14

The sample data used in Example 7 were used. An index formula that maximizes the diagnostic performance of the visceral fat area state reflecting the visceral fat accumulation, was searched devotedly using a method described in International Publication WO 2004/052191 which is an international application filed by the present applicant. A plurality of multivariate analysis formulae having diagnostic performances that are equivalent to that of the index formula 5, were obtained. Those formulae are represented in FIGS. 39 and 40. The values of the respective coefficients in the formulae shown in FIGS. 39 and 40 may be values multiplied by a real number, or values obtained by addition of an arbitrary real constant.

EXAMPLE 15

The sample data used in Example 7 were used. An index formula that maximizes a performance of a discrimination between the 2 groups of the visceral fat accumulation group and the visceral fat accumulation-free group, was searched devotedly using a method described in International Publication WO 2004/052191 which is an international application filed by the present applicant. A plurality of multivariate discriminants having discriminatory performances that are equivalent to that of the index formula 4, were obtained. Those discriminants are represented in FIGS. 41 and 42. The values of the respective coefficients in the discriminants shown in FIGS. 41 and 42 may be values multiplied by a real number, or values obtained by addition of an arbitrary real constant.

EXAMPLE 16

The sample data used in Example 7 were used. An index formula that maximizes a performance of a discrimination between the 2 groups of the visceral fat accumulation group and the visceral fat accumulation-free group, was searched devotedly using a method (method of searching for a multivariate discriminant) described in International Publication WO 2006/098192 which is an international application filed by the present applicant. A plurality of logistic regression equations having discriminatory performances that are equivalent to that of the index formula 6, were obtained. Those discriminants are represented in FIGS. 43 and 44. The values of the respective coefficients in the equations shown in FIGS. 43 and 44 may be values multiplied by a real number, or values obtained by addition of an arbitrary real constant.

EXAMPLE 17

The sample data used in Example 7 were used. An index formula that maximizes a performance of a discrimination between the 2 groups of the visceral fat accumulation group and the visceral fat accumulation-free group, was searched devotedly using a method (method of searching for a multivariate discriminant) described in International Publication WO 2006/098192 which is an international application filed by the present applicant. A plurality of linear discriminants having discriminatory performances that are equivalent to that of the index formula 6, were obtained. Those discriminants are represented in FIGS. 45 and 46. The values of the respective coefficients in the discriminants shown in FIGS. 45 and 46 may be values multiplied by a real number, or values obtained by addition of an arbitrary real constant.

EXAMPLE 18

The sample data used in Example 7 were used. An index formula that maximizes the diagnostic performance of the visceral fat area state reflecting the visceral fat accumulation, was searched devotedly using a method described in International Publication WO 2004/052191 and a method described in International Publication WO 2006/098192 (method of searching for a multivariate discriminant), which are international applications filed by the present applicant. A plurality of multivariate analysis formulae having diagnostic performances that are equivalent to that of the index formula 5, were obtained. Those formulae are represented in FIG. 47. The values of the respective coefficients in the formulae shown in FIG. 47 may be values multiplied by a real number, or values obtained by addition of an arbitrary real constant.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A visceral fat accumulation-evaluating apparatus comprising at least one central processing unit (CPU) and at least one computer-readable recording medium storing a visceral fat accumulation-evaluating program, Wherein the CPU executing the visceral fat accumulation-evaluating program is configured to:
calculate a discriminant value that is a value of a multivariate discriminant containing a concentration of at least one amino acid as an explanatory variable and corresponds to an evaluation result on a visceral fat area state in a subject to be evaluated, using at least both amino acid concentration data of the subject on a concentration value of the amino acid in blood and the multivariate discriminant,
wherein the multivariate discriminant contains at least two of Asn, Cit, His, Thr, Val, Leu, Ile, Tyr, Phe, Trp, Glu, Ala, Pro, Orn, Lys, Gly, Ser, Met, Arg, Cys, and Gln as the explanatory variables; and
wherein the CPU is configured to calculate the discriminant value using at least both the concentration values of at least two of Asn, Cit, His, Thr, Val, Leu, Ile, Tyr, Phe, Trp, Glu, Ala, Pro, Orn, Lys, Gly, Ser, Met, Arg, Cys, and Gln contained in the amino acid concentration data of the subject and the multivariate discriminant;
wherein the CPU is further configured to evaluate visceral fat area state in the subject using at least the discriminant value calculated.

2. The visceral fat accumulation-evaluating apparatus according to claim 1, wherein the CPU is further configured to discriminate between a visceral fat accumulation group and a visceral fat accumulation-free group in the subject using at least the discriminant value calculated.

3. The visceral fat accumulation-evaluating apparatus according to claim 2, wherein the multivariate discriminant is expressed by one fractional expression or the sum of a plurality of the fractional expressions and contains at least two of Asn, Cit, His, Thr, Val, Leu, Ile, Tyr, Phe, Trp, Glu, Ala, Pro, Orn, Lys, Gly, Ser, Met, Arg, Cys, and Gln as the explanatory variables in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

4. The visceral fat accumulation-evaluating apparatus according to claim 3, wherein the multivariate discriminant is formula 1, formula 2, the logistic regression equation containing Ser, Glu, Ile, Tyr, and Arg as the explanatory variables, or the logistic regression equation containing Ser, Glu, Leu, and Trp as the explanatory variables:

$$(Glu+Tyr+Orn)/(Asn+Ser) \quad \text{(formula 1)}$$

$$(Glu+Leu)/(Ser+Tau)+(Pro+Orn)/(Gln) \quad \text{(formula 2).}$$

5. The visceral fat accumulation-evaluating apparatus according to claim 1, wherein the multivariate discriminant is expressed by one fractional expression or the sum of a plurality of the fractional expressions and contains at least two of Asn, Cit, His, Thr, Val, Leu, Ile, Tyr, Phe, Trp, Glu, Ala, Pro, Orn, Lys, Gly, Ser, Met, Arg, Cys, and Gln as the explanatory variables in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

6. The visceral fat accumulation-evaluating apparatus according to claim 5, wherein the multivariate discriminant is formula 3 or formula 4:

$$(Glu+Gly)+(-0.2)\times(Ser/Tyr)+(-0.1)\times(His/Trp) \quad \text{(formula 3)}$$

$$(Glu/Gly)+(-0.54)\times(Ser/Leu)+(0.15)\times(Pro/Trp)+(-0.05)\times(Gln/Tyr) \quad \text{(formula 4).}$$

7. The visceral fat accumulation-evaluating apparatus according to claim 1,

Wherein the CPU is configured to prepare the multivariate discriminant, using at least visceral fat area state information containing the amino acid concentration data and visceral fat area state index data on an index for indicating the visceral fat area state, wherein the CPU is further configured to:
prepare a candidate multivariate discriminant that is a candidate of the multivariate discriminant, using at least a predetermined discriminant-preparing method from the visceral fat area state information;
verify the candidate multivariate discriminant prepared, using at least a predetermined verifying method; and
select the explanatory variable of the candidate multivariate discriminant using at least a predetermined explanatory variable-selecting method, thereby selecting a combination of the amino acid concentration data contained in the visceral fat area state information used in preparing the candidate multivariate discriminant, and
wherein the CPU is further configured to prepare the multivariate discriminant by selecting the candidate multivariate discriminant used as the multivariate discriminant, from a plurality of the candidate multivariate discriminants, using at least the verification results accumulated by repeatedly executing the visceral fat accumulation-evaluating program by the CPU.

8. An information communication terminal apparatus comprising at least one CPU, wherein the CPU is configured to obtain a discriminant value that is a value of a multivariate discriminant containing a concentration of the at least one amino acid as an explanatory variable and corresponds to an evaluation result on a visceral fat area state in a subject to be evaluated,
wherein the discriminant value is calculated using at least both concentration values of at least two of Asn, Cit, His, Thr, Val, Leu, Ile, Tyr, Phe, Trp, Glu, Ala, Pro, Orn, Lys, Gly, Ser, Met, Arg, Cys, and Gln contained in amino acid concentration data on a concentration value of at least one amino acid in blood of the subject and the multivariate discriminant, where at least two of Asn, Cit, His, Thr, Val, Leu, Ile, Tyr, Phe, Trp, Glu, Ala, Pro, Orn, Lys, Gly, Ser, Met, Arg, Cys, and Gln are contained as the explanatory variables; and
wherein the information communication terminal apparatus is communicatively connected via a network to a visceral fat accumulation-evaluating apparatus comprising at least one CPU and at least one computer-readable recording medium storing a visceral fat accumulation-evaluating program, wherein the CPU is configured to calculate the discriminant value using at least the multivariate discriminant, and the CPU of the information communication terminal apparatus or the CPU of the visceral fat accumulation-evaluating apparatus is further configured to evaluate the visceral fat area state in the subject using at least the discriminant value.

9. A visceral fat accumulation-evaluating apparatus comprising at least one CPU and at least one computer-readable recording medium storing a visceral fat accumulation-evaluating program, communicatively connected via a network to an information communication terminal apparatus that provides amino acid concentration data on a concentration value of at least one amino acid in blood of a subject to be evaluated,
wherein the CPU executing the visceral fat accumulation-evaluating program is configured to:
receive the amino acid concentration data of the subject transmitted from the information communication terminal apparatus;
calculate a discriminant value that is a value of a multivariate discriminant containing a concentration of the at least one amino acid as an explanatory variable and corresponds to an evaluation result on a visceral fat area state in the subject, using at least both the amino acid concentration data of the subject and the multivariate discriminant; and
transmit the discriminant value calculated to the information communication terminal apparatus,
wherein the CPU is further configured to calculate the discriminant value using at least both concentration values of at least two of Asn, Cit, His, Thr, Val, Leu, Ile, Tyr, Phe, Trp, Glu, Ala, Pro, Orn, Lys, Gly, Ser, Met, Arg, Cys, and Gln contained in the amino acid concentration data of the subject and the multivariate discriminant where at least two of Asn, Cit, His, Thr, Val, Leu, Ile, Tyr, Phe, Trp, Glu, Ala, Pro, Orn, Lys, Gly, Ser, Met, Arg, Cys, and Gln are contained as the explanatory variables; and
the CPU of the visceral fat accumulation evaluating apparatus or the information communication terminal apparatus is further configured to evaluate the visceral fat area state in the subject using at least the discriminant value.

10. The visceral fat accumulation-evaluating method according to claim 7, wherein the method further includes (ii) a discriminant value criterion evaluating step of evaluating the visceral fat area state in the subject using at least the discriminant value calculated at the discriminant value calculating step, wherein the step (ii) is executed by the control unit of the at least one computer.

11. The visceral fat accumulation-evaluating system according to claim 7, wherein the control unit of the at least one computer of the visceral fat accumulation-evaluating apparatus further includes a discriminant value criterion-evaluating unit configured to evaluate the visceral fat area state in the subject using at least the discriminant value calculated by the discriminant value-calculating unit,
the result-sending unit is configured to transmit the evaluation result of the subject obtained by the discriminant value criterion-evaluating unit to the information communication terminal apparatus, and
the result-receiving unit is configured to receive the evaluation result of the subject transmitted from the visceral fat accumulation-evaluating apparatus.

12. The visceral fat accumulation-evaluating program product according to claim 7, wherein the method further includes (ii) a discriminant value criterion evaluating step of evaluating the visceral fat area state in the subject using at least the discriminant value calculated at the discriminant value calculating step, wherein the step (ii) is executed by the control unit of the at least one computer.

13. A non-transitory computer-readable recording medium, comprising the visceral fat accumulation-evaluating program product according to claim 12 recorded thereon.

14. The information communication terminal apparatus according to claim 8, wherein the CPU is further configured to:
transmit the amino acid concentration data of the subject to the visceral fat accumulation-evaluating apparatus, and
receive the discriminant value transmitted from the visceral fat accumulation-evaluating apparatus.

15. The information communication terminal apparatus according to claim 8, wherein the CPU is further configured to:
receive the evaluation result on the visceral fat area state of the subject transmitted from the visceral fat accumulation-evaluating apparatus instead of obtaining the discriminant value, wherein the evaluation result is the result of evaluating the visceral fat area state in the subject using at least the discriminant value.

16. The visceral fat accumulation-evaluating apparatus according to claim 9, wherein the CPU is further configured to:
transmit the evaluation result of the subject obtained to the information communication terminal apparatus instead of transmitting the discriminant value.

17. The information communication terminal apparatus according to claim 8, wherein the CPU is further configured to obtain the evaluation result on the visceral fat area state of the subject instead of transmitting the discriminant value,
wherein the evaluation result is the result of evaluating the visceral fat area state in the subject using at least the discriminant value.

18. The visceral fat accumulation-evaluating apparatus of claim 1, wherein the multivariate discriminant does not contain Val, Leu, or Ile and the discriminant value-calculating unit does not use the concentration values of Val, Leu, or Ile.

19. A visceral fat accumulation-evaluating apparatus comprising at least one CPU and at least one computer-readable recording medium storing a visceral fat accumulation-evaluating program,
wherein the CPU executing the visceral fat accumulation-evaluating program is configured to:
calculate a discriminant value that is a value of a multivariate discriminant containing a concentration of at least one amino acid as an explanatory variable and corresponds to an evaluation result on a visceral fat accumulation condition in a subject to be evaluated, using at least both amino acid concentration data of the subject on a concentration value of the amino acid in blood and the multivariate discriminant,
wherein the multivariate discriminant contains at least two of Asn, Cit, His, Thr, Tyr, Phe, Trp, Glu, Ala, Pro, Orn, Lys, Gly, Ser, Met, Arg, Cys, and Gln as the explanatory variables; and
wherein the CPU is further configured to calculate the discriminant value using at least both the concentration values of at least two of Asn, Cit, His, Thr, Tyr, Phe, Trp, Glu, Ala, Pro, Orn, Lys, Gly, Ser, Met, Arg, Cys, and Gln contained in the amino acid concentration data of the subject and the multivariate discriminant;
wherein the CPU is further configured to evaluate the visceral fat accumulation condition in the subject using at least the discriminant value calculated.

20. A visceral fat accumulation-evaluating apparatus comprising at least one CPU and at least one computer-readable recording medium storing a visceral fat accumulation-evaluating program,
wherein the CPU executing the visceral fat accumulation-evaluation program is configured to evaluate a visceral fat area state in a subject to be evaluated using at least a discriminant value that is a value of a multivariate discriminant containing a concentration of at least one amino acid as an explanatory variable and corresponds to an evaluation result on the visceral fat area state in the subject,
wherein the discriminant value is calculated using at least both concentration values of at least two of Asn, Cit, His, Thr, Val, Leu, Ile, Tyr, Phe, Trp, Glu, Ala, Pro, Orn, Lys, Gly Ser, Met, Arg, Cys, and Gln contained in amino acid concentration data of the subject on a concentration value of the amino acid in blood and the multivariate discriminant where at least two of Asn, Cit, His, Thr, Val, Leu, Ile, Tyr, Phe, Trp, Glu, Ala, Pro, Orn, Lys, Gly, Ser, Met, Arg, Cys, and Gln are contained as the explanatory variables.

* * * * *